United States Patent
Lundberg et al.

(10) Patent No.: US 11,459,587 B2
(45) Date of Patent: Oct. 4, 2022

(54) MATERIALS AND METHODS FOR TREATMENT OF PAIN RELATED DISORDERS

(71) Applicant: VERTEX PHARMACEUTICALS INCORPORATED, Boston, MA (US)

(72) Inventors: Ante Sven Lundberg, Cambridge, MA (US); Samarth Kulkarni, Cambridge, MA (US); Lawrence Klein, Cambridge, MA (US); Hari Kumar Padmanabhan, Cambridge, MA (US)

(73) Assignee: VERTEX PHARMACEUTICALS INCORPORATED, Boston, MA (US)

(*) Notice: Subject to any disclaimer, the term of this patent is extended or adjusted under 35 U.S.C. 154(b) by 699 days.

(21) Appl. No.: 16/315,547

(22) PCT Filed: Jul. 6, 2017

(86) PCT No.: PCT/IB2017/054086
§ 371 (c)(1),
(2) Date: Jan. 4, 2019

(87) PCT Pub. No.: WO2018/007980
PCT Pub. Date: Jan. 11, 2018

(65) Prior Publication Data
US 2019/0153477 A1 May 23, 2019

Related U.S. Application Data

(60) Provisional application No. 62/461,874, filed on Feb. 22, 2017, provisional application No. 62/358,763, filed on Jul. 6, 2016.

(51) Int. Cl.
*C12N 15/90* (2006.01)
*A61K 35/30* (2015.01)
*C07K 14/705* (2006.01)
*C12N 9/22* (2006.01)
*C12N 15/11* (2006.01)
*C12N 15/113* (2010.01)
*A61P 25/04* (2006.01)
*A61P 43/00* (2006.01)

(52) U.S. Cl.
CPC ............ *C12N 15/907* (2013.01); *A61K 35/30* (2013.01); *C07K 14/705* (2013.01); *C12N 9/22* (2013.01); *C12N 15/11* (2013.01); *C12N 15/1138* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |
| 5,173,414 A | 12/1992 | Lebkowski et al. |
| 5,175,273 A | 12/1992 | Bischofberger et al. |
| 5,177,196 A | 1/1993 | Meyer, Jr. et al. |

(Continued)

FOREIGN PATENT DOCUMENTS

| EP | 2 112 235 A1 | 10/2009 |
|---|---|---|
| EP | 2263705 A1 | 12/2010 |

(Continued)

OTHER PUBLICATIONS

Genbank Accession No. AY243025.1 (which was publically available since Apr. 10, 2003, retrieved from the Internet <<https://www.ncbi.nlm.nih.gov/nuccore/AY243025.1>>, retrieved on Aug. 25, 2021).*
Uniprot Accession No. Q99ZW2 (publically available since Jul. 2012, retrieved from the Internet << https://www.uniprot.org/uniprot/Q99ZW2 >>, retrieved on Aug. 26, 2021.*
Warren et al., "Highly Efficient Reprogramming to Pluripotency and Directed Differentiation of Human Cells with Synthetic Modified mRNA", Cell Stem Cell, 2010, pp. 618-630, vol. 7.
Weber et al., "Methylation of Human MicroRNA Genes in Normal and Neoplastic Cells", Cell Cycle, 2007, pp. 1001-1005, vol. 6, No. 9.

(Continued)

*Primary Examiner* — Suzanne M Noakes
*Assistant Examiner* — Jae W Lee
(74) *Attorney, Agent, or Firm* — Polsinelli PC

(57) ABSTRACT

The present application provides materials and methods for treating a patient with one or more conditions associated with SCN9A whether ex vivo or in vivo. In addition, the present application provides materials and methods for editing and/or modulating the expression of SCN9A gene in a cell by genome editing.

17 Claims, 11 Drawing Sheets

Specification includes a Sequence Listing.

(56) References Cited

U.S. PATENT DOCUMENTS

| | | |
|---|---|---|
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,367,066 A | 11/1994 | Urdea et al. |
| 5,371,241 A | 12/1994 | Brush |
| 5,391,723 A | 2/1995 | Priest |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer, Jr. et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bischofberger et al. |
| 5,658,776 A | 8/1997 | Flotte et al. |
| 5,663,312 A | 9/1997 | Chaturvedula |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,786,211 A | 7/1998 | Johnson |
| 5,830,653 A | 11/1998 | Froehler et al. |
| 5,871,982 A | 2/1999 | Wilson et al. |
| 6,005,096 A | 12/1999 | Matteucci et al. |
| 6,156,303 A | 12/2000 | Russell et al. |
| 6,258,595 B1 | 7/2001 | Gao et al. |
| 6,287,860 B1 | 9/2001 | Monia et al. |
| 7,427,396 B2 | 9/2008 | Arbetman et al. |
| 7,588,772 B2 | 9/2009 | Kay et al. |
| 8,252,538 B2 | 8/2012 | Croce et al. |
| 8,389,210 B2 | 3/2013 | Croce et al. |
| 8,415,096 B2 | 4/2013 | Mohapatra et al. |
| 9,193,769 B2 | 11/2015 | Chiorini et al. |
| 9,238,800 B2 | 1/2016 | Bossis et al. |
| 2003/0158403 A1 | 8/2003 | Manoharan et al. |
| 2005/0059005 A1 | 3/2005 | Tuschl et al. |
| 2005/0261218 A1 | 11/2005 | Esau et al. |
| 2009/0092974 A1 | 4/2009 | Davison et al. |
| 2009/0131348 A1 | 5/2009 | Labourier et al. |
| 2009/0263803 A1 | 10/2009 | Beaudenon et al. |
| 2010/0286232 A1 | 11/2010 | Schmittgen et al. |
| 2010/0323357 A1 | 12/2010 | Nana-Sinkam et al. |
| 2011/0016541 A1 | 1/2011 | Weinstein et al. |
| 2011/0023148 A1 | 1/2011 | Weinstein et al. |
| 2011/0171646 A1 | 7/2011 | Schmittgen et al. |
| 2011/0281756 A1 | 11/2011 | Wu et al. |
| 2012/0053224 A1 | 3/2012 | Meister et al. |
| 2012/0214699 A1 | 8/2012 | Croce et al. |
| 2012/0264626 A1 | 10/2012 | Nana-Sinkam et al. |
| 2012/0283310 A1 | 11/2012 | Croce et al. |
| 2012/0309645 A1 | 12/2012 | Keller et al. |
| 2012/0316081 A1 | 12/2012 | List et al. |
| 2012/0329672 A1 | 12/2012 | Croce et al. |
| 2013/0042333 A1 | 2/2013 | Judde et al. |
| 2013/0053263 A1 | 2/2013 | Keller et al. |
| 2013/0053264 A1 | 2/2013 | Keller et al. |
| 2013/0059015 A1 | 3/2013 | Lancaster et al. |
| 2014/0068797 A1 | 3/2014 | Doudna et al. |
| 2015/0291966 A1 | 10/2015 | Zhang et al. |
| 2016/0017005 A1 | 1/2016 | Asokan et al. |
| 2017/0121693 A1 | 5/2017 | Liu et al. |
| 2018/0258424 A1* | 9/2018 | Greenberg .......... C12N 5/0619 |

FOREIGN PATENT DOCUMENTS

| | | |
|---|---|---|
| JP | 2009215191 A | 9/2009 |
| JP | 2013500018 A | 1/2013 |
| WO | 93/07883 A1 | 4/1993 |
| WO | 95/13365 A1 | 5/1995 |
| WO | 95/13392 A1 | 5/1995 |
| WO | 96/17947 A1 | 6/1996 |
| WO | 97/06243 A1 | 2/1997 |
| WO | 97/08298 A1 | 3/1997 |
| WO | 97/09441 A2 | 3/1997 |
| WO | 97/21825 A1 | 6/1997 |
| WO | 99/11764 A2 | 3/1999 |
| WO | 01/83692 A2 | 11/2001 |

(56) References Cited

FOREIGN PATENT DOCUMENTS

| | | |
|---|---|---|
| WO | 2007/081740 A2 | 7/2007 |
| WO | 2008/054828 A2 | 5/2008 |
| WO | 2008/073915 A2 | 6/2008 |
| WO | 2008/154098 A2 | 12/2008 |
| WO | 2009/070653 A1 | 6/2009 |
| WO | 2009/100430 A2 | 8/2009 |
| WO | 2010/018563 A2 | 2/2010 |
| WO | 2010140698 A1 | 12/2010 |
| WO | 2011011767 A1 | 1/2011 |
| WO | 2011/076142 A1 | 6/2011 |
| WO | 2011/076143 A1 | 6/2011 |
| WO | 2011/095623 A2 | 8/2011 |
| WO | 2011/157294 A1 | 12/2011 |
| WO | 2012/151212 A1 | 11/2012 |
| WO | 2013/011378 A1 | 1/2013 |
| WO | 2013/033640 A1 | 3/2013 |
| WO | 2013/066678 A1 | 5/2013 |
| WO | 2013061205 A2 | 5/2013 |
| WO | 2013/176772 A1 | 11/2013 |
| WO | 2014/159595 A2 | 10/2014 |
| WO | 2015/048577 A2 | 4/2015 |
| WO | 2015/051216 A1 | 4/2015 |
| WO | 2015/070083 A1 | 5/2015 |
| WO | 2015/121501 A1 | 8/2015 |
| WO | 2015/175642 A2 | 11/2015 |
| WO | 2016/057800 A1 | 4/2016 |
| WO | 2016/191684 A1 | 12/2016 |
| WO | 2017/024319 A1 | 2/2017 |
| WO | 2017/075222 A1 | 5/2017 |
| WO | 2017/083722 A1 | 5/2017 |
| WO | 2018/007976 A1 | 1/2018 |
| WO | 2018/007980 A1 | 1/2018 |
| WO | 2018/022668 A2 | 2/2018 |
| WO | 2018/035503 A1 | 2/2018 |
| WO | 2018/049079 A1 | 3/2018 |
| WO | 2018/165503 A1 | 9/2018 |
| WO | 2018/165504 A1 | 9/2018 |

OTHER PUBLICATIONS

Weber et al., "A Modular Cloning System for Standardized Assembly of Multigene Constructs", PLoS One, 2011, e16765, pp. 1-11, vol. 6, No. 2.
Whitehead et al., "Silencing or Stimulation? siRNA Delivery and the Immune System", Annual Review of Chemical and Biomolecular Engineering, 2011, pp. 77-96, vol. 2.
Winkler, "Oligonucleotide conjugates for therapeutic applications", Ther. Deliv., 2013, pp. 791-809, vol. 4, No. 7.
Wolfs et al., "MegaTevs: single-chain dual nucleases for efficient gene disruption", Nucleic Acids Research, 2014, pp. 8816-8829, vol. 42, No. 13.
Zhao et al., "Sequence-specific inhibition of microRNA via CRISPR/CRISPRi system", Scientific Reports, 2014, pp. 1-5, vol. 4.
International Search Report and Written Opinion relating to International Application No. PCT/IB2017/054086, dated Nov. 8, 2017; 10 pgs.
Ma et al., "Pol III Promoters to Express Small RNAs: Delineation of Transcription Initiation", Molecular Therapy—Nucleic Acids, 2014, e161, pp. 1-11, vol. 3.
Maherali et al., "Guidelines and Techniques for the Generation of Induced Pluripotent Stem Cells", Cell Stem Cell, 2008, pp. 595-605, vol. 3.
Mak et al., "The crystal structure of TAL effector PthXo1 bound to its DNA target", Science, 2012, pp. 716-719, vol. 335, No. 6069.
Manoharan et al., "Introduction of a Lipophilic Thioether Tether in the Minor Groove of Nucleic Acids for Antisense Applications", Bioorganic & Medicinal Chemistry Letters, 1993, pp. 2765-2770, vol. 3, No. 12.
Manoharan et al., "Chemical Modifications to Improve Uptake and Bioavailability of Antisense Oligonucleotides", Annals New York Academy of Sciences, 1994, pp. 306-309, vol. 660.
Manoharan et al., "Cholic Acid-Oligonucleotide Conjugates for Antisense Applications", Bioorganic & Medicinal Chemistry Letters, 1994, pp. 1053-1060, vol. 4, No. 8.
Manoharan et al., "Oligonucleotide Conjugates: Alteration of the Pharmacokinetic Properties of Antisense Agents", Nucleosides & Nucleotides, 1995, pp. 969-973, vol. 14.
Manoharan et al., "Lipidic Nucleic Acids", Tetrahedron Letters, 1995, pp. 3651-3654, vol. 36, No. 21.
Maresca et al., "Obligate Ligation-Gated Recombination (ObLiGaRe): Custom-designed nuclease-mediated targeted integration through nonhomologous end joining", Genome Research, 2013, pp. 539-546, vol. 23.
Marson et al., "Wnt Signaling Promotes Reprogramming of Somatic Cells to Pluripotency", Cell Stem Cell, 2008, pp. 132-135, vol. 3.
Martin et al., "38. Ein neuer Zugang zu 2'-O-Alkylribonucleosiden und Eigenschaften deren Oligonucleotide". Helvetica Chimica Acta, 1995, pp. 486-504, vol. 78.—English abstract.
Mateos-Gomez et al., "Mammalian Polymerase Theta Promotes Alternative-NHEJ and Suppresses Recombination", Nature, 2015, pp. 254-257, vol. 518.
McLaughlin et al., "Adeno-Associated Virus General Transduction Vectors: Analysis of Proviral Structures", Journal of Virology, 1988, pp. 1963-1973, vol. 62, No. 6.
Mishra et al., "Improved leishmanicidal effect of phosphorotioate antisense oligonucleotides by LDL-mediated delivery", Biochimica et Biophysica Acta, 1995, pp. 229-237, vol. 1264.
Moscou et al., "A Simple Cipher Governs DNA Recognition by TAL Effectors", Science, 2009, p. 1501, vol. 326.
Muzyczka, "Use of Adeno-Associated Virus as a General Transduction Vector for Mammalian Cells", Current Topics in Microbiology and Immunology, 1992, pp. 97-129, vol. 158.
Nasevicius et al., "Effective targeted gene 'knockdown' in zebrafish", Nature Genetics, 2000, pp. 216-220, vol. 26.
Nielsen et al., "Sequence-Selective Recognition of DNA by Strand Displacement with a Thymine-Substituted Polyamide", Science, 1991, pp. 1497-1500, vol. 254.
Oberhauser et al., "Effective incorporation of 2'-O-methyl-oligoribonucleotides into liposomes and enhanced cell association through modification with thiocholesterol", Nucleic Acids Research, 1992, pp. 533-538, vol. 20, No. 3.
Paul et al., "Increased Viral Titer Through Concentration of Viral Harvests from Retroviral Packaging Lines", Human Gene Therapy, 1993, pp. 609-615, vol. 4.
Peer et al., "Special delivery: targeted therapy with small RNAs", Gene Therapy, 2011, pp. 1127-1133, vol. 18.
Perrin et al., "An experimental rabies vaccine produced with a new BHK-21 suspension cell culture process: use of serum-free medium and perfusion-reactor system", Vaccine, 1995, pp. 1244-1250, vol. 13, No. 13.
Pittenger et al., "Multilineage Potential of Adult Human Mesenchymal Stem Cells", Science, 1999, pp. 143-147, vol. 284.
Posadas et al., "MicroRNAs and their roles in developmental canalization", Curr Opin Genet Dev., 2014, pp. 1-6, vol. 27.
Pulicherla et al., "Engineering Liver-detargeted AAV9 Vectors for Cardiac and Musculoskeletal Gene Transfer", Molecular Therapy, 2011, pp. 1070-1078, vol. 19, No. 6.
Saj et al., "Control of microRNA biogenesis and transcription by cell signaling pathways", Curr Opin Genet Dev., 2011, pp. 504-510, vol. 21, No. 4.
Samulski et al., "Helper-Free Stocks of Recombinant Adeno-Associated Viruses: Normal Integration Does Not Require Viral Gene Expression", Journal of Virology, 1989, pp. 3822-3828, vol. 63, No. 9.
Sapranauskas et al., "The *Streptococcus thermophilus* CRISPR/Cas system provides immunity in *Escherichia coli*", Nucleic Acids Research, 2011, pp. 9275-9282, vol. 39, No. 21.
Segal et al., "Toward controlling gene expression at will: Selection and design of zinc finger domains recognizing each of the 5'-GNN-3' DNA target sequences", PNAS, 1999, pp. 2758-2763, vol. 96.
Shea et al., "Synthesis, hybridization properties and antiviral activity of lipid-oligodeoxynucleotide conjugates", Nucleic Acids Research, 1990, pp. 3777-3783, vol. 18, No. 13.

(56) References Cited

OTHER PUBLICATIONS

Shi et al., "A Combined Chemical and Genetic Approach for the Generation of Induced Pluripotent Stem Cells", Cell Stem Cell, 2008, pp. 525-528, vol. 2.
Soutschek et al., "Therapeutic silencing of an endogenous gene by systemic administration of modified siRNAs", Nature, 2004, pp. 173-178, vol. 432.
Steentoft et al., "Precision genome editing: A small revolution for glycobiology", Glycobiology, 2014, pp. 663-680, vol. 24, No. 8.
Stern-Ginossar et al., "Host Immune System Gene Targeting by a Viral miRNA", Science, 2007, pp. 376-381, vol. 317, with Supporting Material.
Suzuki et al., "In vivo genome editing via CRISPR/Cas9 mediated homology-independent targeted integration", Nature, 2016, pp. 144-149, vol. 540, and extended data.
Svinarchuk et al., "Inhibition of HIV proliferation in MT-4 cells by antisense oligonucleotide conjugated to lipophilic groups", Biochimie, 1993, pp. 49-54, vol. 75.
Takahashi et al., "Induction of Pluripotent Stem Cells from Mouse Embryonic and Adult Fibroblast Cultures by Defined Factors", Cell, 2006, pp. 663-676, vol. 126.
Takahashi et al., "Induction of Pluripotent Stem Cells from Adult Human Fibroblasts by Defined Factors", Cell, 2007, pp. 861-872, vol. 131.
Tratschin et al., "A Human Parvovirus, Adeno-Associated Virus, as a Eucaryotic Vector: Transient Expression and Encapsidation of the Procaryotic Gene for Chloramphenicol Acetyltransferase", Molecular and Cellular Biology, 1984, pp. 2072-2081, vol. 4, No. 10.
Tratschin et al., "Adeno-Associated Virus Vector for High-Frequency Integration, Expression, and Rescue of Genes in Mammalian Cells", Molecular and Cellular Biology, 1985, pp. 3251-3260, vol. 5, No. 11.
Tsai et al., "Dimeric CRISPR RNA-guided FokI nucleases for highly specific genome editing", Nature Biotechnology, 2014, pp. 569-576, vol. 32, No. 6.
Volkov et al., "Selective Protection of Nuclease-Sensitive Sites in siRNA Prolongs Silencing Effect", Oligonucleotides, 2009, pp. 191-202, vol. 19, No. 2.
Wang et al., "Cyclohexene Nucleic Acids (CeNA): Serum Stable Oligonucleotides that Activate RNase H and Increase Duplex Stability with Complementary RNA", Journal of the American Chemical Society, 2000, pp. 8595-8602, vol. 122, No. 36.
Wang et al., "Rapid and Efficient Assembly of Transcription Activator-Like Effector Genes by USER Cloning", Journal of Genetics and Genomics, 2014, pp. 339-347, vol. 41, No. 6.
Wang et al., "Induced Pluripotent Stem Cells for Neural Tissue Engineering", Biomaterials, 2011, pp. 5023-5032, vol. 32, No. 22.
Anand et al., "MicroRNA-mediated Regulation of the Angiogenic Switch", Curr Opin Hematol., 2011, pp. 171-176, vol. 18, No. 3.
Andersen et al., "A rapid and versatile method for the isolation, purification and cryogenic storage of Schwann cells from adult rodent nerves", Scientific Reports—Nature, 2016, 31781, pp. 1-17, vol. 6.
Angart et al., "Design of siRNA Therapeutics from the Molecular Scale", Pharmaceuticals, 2013, pp. 440-468, vol. 6.
Annoni et al., "In vivo delivery of a microRNA-regulated transgene induces antigen-specific regulatory T cells and promotes immunologic tolerance", Blood, 2009, pp. 5152-5161, vol. 114, No. 25.
Barrett et al., "Reliable Generation of Induced Pluripotent Stem Cells From Human Lymphoblastoid Cell Lines", Stem Cells Translational Medicine, 2014, pp. 1429-1434, vol. 3.
Bartel, "MicroRNAs: Target Recognition and Regulatory Functions", Cell, 2009, pp. 215-233, vol. 136.
Behlke, "Chemical Modification of siRNAs for In Vivo Use", Oligonucleotides, 2008, pp. 305-319, vol. 18.
Belfort et al., "Homing Endonucleases: From Genetic Anomalies to Programmable Genomic Clippers", Methods Mol Biol., 2014, pp. 1-26, vol. 1123.
Boch et al., "Breaking the Code of DNA Binding Specificity of TAL-Type III Effectors", Science, 2009, pp. 1509-1512, vol. 326.

Boissel et al., "megaTALs: a rare-cleaving nuclease architecture for therapeutic genome engineering", Nucleic Acids Research, 2014, pp. 2591-2601, vol. 42, No. 4.
Boissel et al., "Assembly and Characterization of megaTALs for Hyperspeci! c Genome Engineering Applications", Methods in Molecular Biology, 2015, pp. 171-196, vol. 1239.
Bonauer et al., "Vascular microRNAs", Current Drug Targets, 2010, pp. 943-949, vol. 11.
Braasch et al., "Novel Antisense and Peptide Nucleic Acid Strategies for Controlling Gene Expression", Biochemistry, 2002, pp. 4503-4510, vol. 41, No. 14.
Bramsen et al., "Development of therapeutic-grade small interfering RNAs by chemical engineering", Frontiers in Genetics, 2012, pp. 1-22, vol. 3, No. 154.
Budniatzky et al., "Concise Review: Reprogramming Strategies for Cardiovascular Regenerative Medicine: From Induced Pluripotent Stem Cells to Direct Reprogramming", Stem Cells Translational Medicine, 2014, pp. 448-457, vol. 3.
Burnett et al., "Current Progress of siRNA/shRNA Therapeutics in Clinical Trials", Biotechnol J., 2011, pp. 1130-1146, vol. 6, No. 9.
Canver et al., "BCL11A enhancer dissection by Cas9-mediated in situ saturating mutagenesis", Nature, 2015, pp. 192-197, vol. 527.
Carter, "Adeno-associated virus vectors", Current Opinion in Biotechnology, 1992, pp. 533-539, vol. 3.
Ceccaldi et al., "Homologous recombination-deficient tumors are hyper-dependent on POLQ-mediated repair", Nature, 2015, pp. 258-262, vol. 518.
Cekaite et al., "Gene Expression Analysis in Blood Cells in Response to Unmodified and 2'-Modified siRNAs Reveals TLR-dependent and Independent Effects", J. Mol. Biol., 2007, pp. 90-108, vol. 365.
Communication pursuant to Article 94(3) EPC relating to EP Application No. 17754196.8, dated Jun. 4, 2020; 5 pgs.
Communication pursuant to Article 94(3) EPC relating to EP Application No. 17754197.6, dated Aug. 6, 2020; 6 pgs.
Cermak et al., "Efficient design and assembly of custom TALEN and other TAL effector-based constructs for DNA targeting", Nucleic Acids Research, 2011, e82, pp. 1-11, vol. 39, No. 12.
Cermak et al., "Efficient Design and Assembly of Custom TALENs Using the Golden Gate Platform", Methods in Molecular Biology, 2015, pp. 133-159, vol. 1239.
Chen et al., "Global microRNA depletion suppresses tumor angiogenesis", Genes & Development, 2014, pp. 1054-1067, vol. 28.
Chernolovskaya et al., "Chemical modification of siRNA", Current Opinion in Molecular Therapeutics, 2010, pp. 1-10, vol. 12, No. 2.
Cho et al., "Familiar ends with alternative endings", Nature, 2015, pp. 174-176, vol. 518.
Chylinski et al., "The tracrRNA and Cas9 families of type II CRISPR-Cas immunity systems", RNA Biology, 2013, pp. 726-737, vol. 10, No. 5.
Contreras et al., "MicroRNAs in inflammation and immune responses", Leukemia, 2012, pp. 404-413, vol. 26.
Cox et al., "Therapeutic Genome Editing: Prospects and Challenges", Nature Medicine, 2015, pp. 121-131, vol. 21, No. 2.
Cristea et al., "In vivo Cleavage of Transgene Donors Promotes Nuclease-Mediated Targeted Integration", Biotechnology and Bioengineering, 2013, pp. 871-880, vol. 110, No. 3.
Crooke et al., "Pharmacokinetic properties of several novel oligonucletide analogs in mice", The Journal of Pharmacology and Experimental Therapeutics, 1996, pp. 923-937, vol. 277.
De Mesmaeker et al., "Antisense Oligonucleotides", Acc. Chem. Res., 1995, pp. 366-374, vol. 28, No. 9.
Deltcheva et al., "CRISPR RNA maturation by trans-encoded small RNA and host factor RNase III", Nature, 2011, pp. 602-607, vol. 471.
Deverman et al., "Cre-dependent selection yields AAV variants for widespread gene transfer to the adult brain", Nature Biotechnology, 2016, pp. 204-209, vol. 34, No. 2.
Dreier et al., "Insights into the Molecular Recognition of the 5'-GNN-3' Family of DNA Sequences by Zinc Finger Domains", Journal of Molecular Biology, 2000, pp. 489-502, vol. 303.
Dreier et al., "Development of Zinc Finger Domains for Recognition of the 5'-ANN-3' Family of DNA Sequences and Their Use in

(56) References Cited

OTHER PUBLICATIONS the Construction of Artificial Transcription Factors", The Journal of Biological Chemistry, 2001, pp. 29466-29478, vol. 276, No. 31.

Dreier et al., "Development of Zinc Finger Domains for Recognition of the 5'-CNN-3' Family DNA Sequences and Their Use in the Construction of Artificial Transcription Factors", The Journal of Biological Chemistry, 2005, pp. 35588-35597, vol. 280, No. 42.

Focosi et al., "Induced pluripotent stem cells in hematology: current and future applications", Blood Cancer Journal, 2014, e211, pp. 1-8, vol. 4.

Fonfara et al., "Phylogeny of Cas9 determines functional exchangeability of dual-RNA and Cas9 among orthologous type II CRISPR-Cas systems", Nucleic Acids Research, 2014, pp. 2577-2590, vol. 42, No. 4.

Fucini et al., "Adenosine Modification May Be Preferred for Reducing siRNA Immune Stimulation", Nucleic Acid Therapeutics, 2012, pp. 205-210, vol. 22, No. 3.

Gaglione et al., "Recent Progress in Chemically Modified siRNAs", Mini-Reviews in Medicinal Chemistry, 2010, pp. 578-595, vol. 10, No. 7.

Gebeyehu et al., "Novel biotinylated nucleotide—analogs for labeling and colorimetric detecton of DNA", Nucleic Acids Research, 1987, pp. 4513-4534, vol. 15, No. 11.

Gentner et al., "Exploiting microRNA regulation for genetic engineering", Tissue Antigens, 2012, pp. 393-403, vol. 80.

Grimm et al., "In Vitro and In Vivo Gene Therapy Vector Evolution via Multispecies Interbreeding and Retargeting of Adeno-Associated Viruses", Journal of Virology, 2008, pp. 5887-5911, vol. 82, No. 12.

Grimson et al., "MicroRNA Targeting Specificity in Mammals: Determinants beyond Seed Pairing", Molecular Cell, 2007, pp. 91-105, vol. 27.

Guilinger et al., "Fusion of catalytically inactive Cas9 to Fokl nuclease improves the specificity of genome modification", Nature Biotechnology, 2014, pp. 577-582, vol. 32, No. 6.

Hafez et al., "Homing endonucleases: DNA scissors on a mission", Genome, 2012, pp. 553-569, vol. 55.

Heasman, "Morpholino Oligos: Making Sense of Antisense?", Developmental Biology, 2002, pp. 209-214, vol. 243.

Hermonat et al., "Use of adeno-associated virus as a mammalian DNA cloning vector: Transduction of neomycin resistance into mammalian tissue culture cells", PNAS, 1984, pp. 6466-6470, vol. 81.

Herranz et al., "MicroRNAs and gene regulatory networks: managing the impact of noise in biological systems", Genes & Development, 2010, pp. 1339-1344, vol. 24.

Hoyng et al., "Gene therapy and peripheral nerve repair: a perspective", Frontiers in Molecular Neuroscience, 2015, pp. 1-9, vol. 8, No. 32.

Hu et al., "Physiological Roles of Asialoglycoprotein Receptors (ASGPRs) Variants and Recent Advances in Hepatic-Targeted Delivery of Therapeutic Molecules Via ASGPRs", Protein & Peptide Letters, 2014, pp. 1025-1030, vol. 21, No. 10.

Huangfu et al., "Induction of pluripotent stem cells by defined factors is greatly improved by small-molecule compounds", Nature Biotechnology, 2008, pp. 795-797, vol. 26, No. 7.

Jinek et al., "A Programmable Dual-RNA-Guided DNA Endonuclease in Adaptive Bacterial Immunity", Science, 2012, pp. 816-821, vol. 337.

Judge et al., "Design of Noninflammatory Synthetic siRNA Mediating Potent Gene Silencing in Vivo", Molecular Therapy, 2006, pp. 494-505, vol. 13, No. 3.

Judge et al., "Overcoming the Innate Immune Response to Small Interfering RNA", Human Gene Therapy, 2008, pp. 1-14, vol. 19.

Kabanov et al., "A new class of antivirals: antisense oligonucleotides combined with a hydrophobic substituent effectively inhibit influenza virus reproduction and systhesis of virus-specific proteins in MDCK cells", FEBS Letters, 1990, pp. 327-330, vol. 259, No. 2.

Kanasty et al., "Action and Reaction: The Biological Response to siRNA and Its Delivery Vehicles", Molecular Therapy, 2012, pp. 513-524, vol. 20, No. 3.

Kariko et al., "Suppression of RNA Recognition by Toll-like Receptors: The Impact of Nucleoside Modification and the Evolutionary Origin of RNA", Immunity, 2005, pp. 165-175, vol. 23.

Kent et al., "Mechanism of Microhomology-Mediated End-Joining Promoted by Human DNA Polymerase Theta", Mature Structural & Molecular Biology, 2015, pp. 230-237, vol. 22, No. 3.

Kleinstiver et al., "The I-Tevl Nuclease and Linker Domains Contribute to the Specificity of Monomeric TALENs", Genes/Genomes/Genetics, 2014, pp. 1155-1165, vol. 4.

Kole et al., "RNA therapeutics: beyond RNA interference and antisense oligonucleotides", Nature Reviews/Drug Discovery, 2012, pp. 125-140, vol. 11.

Kormann et al., "Expression of therapeutic proteins after delivery of chemically modified mRNA in mice", Nature Biotechnology, 2011, pp. 154-157, vol. 29.

Lacerra et al., "Restoration of hemoglobin A synthesis in erythroid cells from peripheral blood of thalassemic patients", PNAS, 2000, pp. 9591-9596, vol. 97, No. 17.

Ladak et al., "Differentiation of mesenchymal stem cells to support peripheral nerve regeneration in a rat model", Experimental Neurology, 2011, pp. 242-252, vol. 228.

Landgraf et al., "A Mammalian microRNA Expression Atlas Based on Small RNA Library Sequencing", Cell, 2007, pp. 1401-1414, vol. 129.

Lebkowski et al., "Adeno-Associated Virus: a Vector System for Efficient Introduction and Integration of DNA into a Variety of Mammalian Cell Types", Molecular and Cellular Biology, 1988, pp. 3988-3996, vol. 8, No. 10.

Letsinger et al., "Cholesteryl-conjugated oligonucleotides: Synthesis, properties, and activity as inhibitors of replication of human immunodeficiency virus in cell culture", PNAS, 1989, pp. 6553-6556, vol. 86.

Li et al., "Modularly assembled designer TAL effector nucleases for targeted gene knockout and gene replacement in eukaryotes", Nucleic Acids Research, 2011, pp. 6315-6325, vol. 39, No. 14.

Liu et al., "Validated Zinc Finger Protein Designs for All 16 GNN DNA Triplet Targets", The Journal of Biological Chemistry, 2002, pp. 3850-3856, vol. 277, No. 6.

Bennett D.L.H., et al., "Painful and painless channelopathies," Lancet Neurology, Jun. 2014, vol. 13, pp. 587-599.

Examination Report No. 1 for Australian Patent Application No. 2017292169, dated Aug. 23, 2021, 4 pages.

Examination Report No. 1 for Australian Patent Application No. 2017292173, dated Aug. 24, 2021, 4 pages.

Fertleman C.R., et al., "SCN9A Mutations in Paroxysmal Extreme Pain Disorder: Allelic Variants Underlie Distinct Channel Defects and Phenotypes," Neuron, 2006, vol. 52, pp. 767-774.

Hendel A., et al., "Chemically modified guide RNAs enhance CRISPR-Cas genome editing in human primary cells," Mature Biotechnology, vol. 33(9), Sep. 2015, 7 pages.

Huang J., et al., "Small-Fiber Neuropathy Nav1.8 Mutation Shifts Activation to Hyperpolarized Potentials and Increases Excitability of Dorsal Root Ganglion Neurons," The Journal of Neuroscience, Aug. 28, 2013, vol. 33(35), pp. 14087-14097.

International Search Report and Written Opinion for International Application No. PCT/IB2017/054081, dated Nov. 3, 2017, 10 pages.

International Preliminary Report on Patentability for International Application No. PCT/IB2017/054081, dated Jan. 17, 2019, 7 pages.

International Preliminary Report on Patentability for International Application No. PCT/IB2017/054086, dated Jan. 17, 2019, 7 pages.

Li H.L., et al., "Precise Correction of the Dystrophin Gene in Duchenne Muscular Dystrophy Patient Induced Pluripotent Stem Cells by TALEN and CRISPR-Cas9," Stem Cell Reports, Jan. 13, 2015, vol. 4, pp. 143-154.

Office Action for European Application No. 17754196.8, dated Feb. 9, 2021, 5 pages.

(56) References Cited

OTHER PUBLICATIONS

Office Action for European Application No. 17754197.6, dated Aug. 6, 2021, 5 pages.
Office Action for Japanese Patent Application No. 2019-500268, dated Jul. 27, 2021, 18 pages.
Office Action for Japanese Patent Application No. 2019-500283, dated Aug. 10, 2021, 7 pages.

Rannals M.D., et al., "Psychiatric Risk Gene Transcription Factor 4 Regulates Intrinsic Excitability of Prefrontal Neurons via Repression of SCN10a and KCNQ1," Neuron, Apr. 6, 2016, vol. 90, pp. 43-55.
Schroeder C.L., et al., "Rational Design and Synthesis of a Novel Membrane Binding NaV1.8 Selective Inhibitor with in vivo Activity in Pain Models," Biophysical Journal, Feb. 28, 2016, vol. 110(3), p. 33a.

* cited by examiner

FIGURE 2A

| SEQ ID NO. | Name | Sequence | Indel | R2 |
|---|---|---|---|---|
| 46832 | SCN9A_Int13_Int14_T4 | TGTGCAAATCTGTACCACCA | 98.5 | 0.9854 |
| 49122 | SCN9A_Int5_Int6_T10 | CAAATAGTTGGAGTTATGAG | 97.5 | 0.975 |
| 49431 | SCN9A_Int2_Int5_T31 | CAGCAGTTTACCTTTCTACA | 96.9 | 0.9844 |
| 47474 | SCN9A_Int10_Int11_T22 | CACCTATTAGCATAACAACA | 96.7 | 0.9848 |
| 47446 | SCN9A_Int10_Int11_T6 | TATGCCCTTCGACACCAAGG | 96.4 | 0.9869 |
| 28779 | SCN9A_Int8_Int9_T21 | GAGCTTTGACACTTCAGCT | 96.4 | 0.9861 |
| 29821 | SCN9A_Int6_Int7_T3 | CAGGCCTGAAGACAATTGTA | 96 | 0.9712 |
| 28146 | SCN9A_Int10_Int11_T17 | GTGAAAGATGTCCTGTCCTA | 95.9 | 0.9618 |
| 49436 | SCN9A_Int2_Int5_T35 | GCCATCAGACTCCAGCAATG | 95.9 | 0.9683 |
| 47224 | SCN9A_Int11_Int12_T26 | CTGGCAGAAGCTGTCCATTG | 95.6 | 0.9894 |
| 47462 | SCN9A_Int10_Int11_T12 | CCGCTGCCGCTGCAATTGCC | 95.6 | 0.974 |
| 47240 | SCN9A_Int11_Int12_T3 | CGTTCACCGGCAGCATTGGT | 95.5 | 0.9825 |
| 27323 | SCN9A_Int14_int15_T1 | AGTTCTGCGATCATTCAGAC | 95.1 | 0.9812 |
| 27522 | SCN9A_Int13_Int14_T2 | GGAACACCACCCAATGACTG | 95 | 0.9498 |
| 27893 | SCN9A_Int11_Int12_T20 | TAGGTCCCCACCAATGCTGC | 94.8 | 0.9897 |
| 47261 | SCN9A_Int11_Int12_T28 | AAGGAGCCACGAATGCTGAG | 94.6 | 0.9866 |
| 28137 | SCN9A_Int10_Int11_T21 | GCCCAACCAGGCAATTGCAG | 94.4 | 0.9559 |
| 49367 | SCN9A_Int2_Int5_T8 | CCAGTCCGGTGGGTTATTCA | 94.3 | 0.9456 |
| 47232 | SCN9A_Int11_Int12_T8 | GGCTGAGCGTCCATCAACCA | 94.1 | 0.9419 |
| 47445 | SCN9A_Int10_Int11_T7 | GCCTATGCCCTTCGACACCA | 93.9 | 0.9884 |
| 49313 | SCN9A_Int2_Int5_T38 | TATATTGGAGGATGGCTGTT | 93.9 | 0.9718 |
| 47267 | SCN9A_Int11_Int12_T24 | ATAAATACCACTGAACCCAC | 93.8 | 0.9543 |
| 30622 | SCN9A_Int1_Int2_T9 | CCATCCAGGCCTCTTATGTG | 93.8 | 0.9864 |
| 47231 | SCN9A_Int11_Int12_T5 | GGGCTGAGCGTCCATCAACC | 93.3 | 0.9599 |

FIGURE 2B

| | | | | |
|---|---|---|---|---|
| 26766 | SCN9A_Int16_Int17_T10 | TGACAGTGCCAATTGCACCT | 93 | 0.9654 |
| 28139 | SCN9A_Int10_Int11_T4 | GTTAACGTCTTGGCCCAACC | 92.4 | 0.989 |
| 46079 | SCN9A_Int16_Int17_T9 | TAGGTTTAGGACCTATATCA | 92 | 0.9684 |
| 48091 | SCN9A_Int8_Int9_T18 | CTCAAGGTTTCTTCTATAGG | 91.2 | 0.9861 |
| 46833 | SCN9A_Int13_Int14_T1 | GCAAATCTGTACCACCAAGG | 91.1 | 0.9634 |
| 26765 | SCN9A_Int16_Int17_T16 | GACAGTGCCAATTGCACCTG | 91 | 0.955 |
| 27876 | SCN9A_Int11_Int12_T27 | GCCAGAGGTGATAATAGATA | 90.8 | 0.9079 |
| 47241 | SCN9A_Int11_Int12_T18 | GTTCACCGGCAGCATTGGTG | 90.7 | 0.9566 |
| 47248 | SCN9A_Int11_Int12_T22 | GCGTCGCTCCTGGGGTCTGT | 90.7 | 0.9566 |
| 30051 | SCN9A_Int2_Int5_T34 | CCCAATGGAATCTTGTGTTT | 90.7 | 0.9414 |
| 30111 | SCN9A_Int2_Int5_T18 | TATGACCATGAATAACCCAC | 90.4 | 0.9198 |
| 28760 | SCN9A_Int8_Int9_T16 | TGTTAAGAGCCTGTATTAGG | 89.8 | 0.9789 |
| 28085 | SCN9A_Int10_Int11_T23 | ATAGGCGAGCACATGAAAAG | 89.6 | 0.9545 |
| 27254 | SCN9A_Int15_Int16_T19 | AAGATCATTGGTAACTCAGT | 89.4 | 0.9459 |
| 30163 | SCN9A_Int2_Int5_T9 | GATAGATGCGTTGATGACAT | 89.3 | 0.9015 |
| 49303 | SCN9A_Int2_Int5_T44 | CCTAAACACAAGATTCCATT | 89 | 0.9199 |
| 28083 | SCN9A_Int10_Int11_T2 | GAGGTTGTCTACCCCCAATC | 88.8 | 0.9471 |
| 49344 | SCN9A_Int2_Int5_T30 | GCAGGTTAATATCATAGAGG | 88.6 | 0.9133 |
| 47245 | SCN9A_Int11_Int12_T2 | GTTACTGCTGCGTCGCTCCT | 87.6 | 0.9615 |
| 48090 | SCN9A_Int8_Int9_T22 | ACTCAAGGTTTCTTCTATAG | 87.3 | 0.9635 |
| 28132 | SCN9A_Int10_Int11_T16 | CGGCTGAATATACAAGTATT | 87.1 | 0.9525 |
| 27328 | SCN9A_Int14_Int15_T2 | GGAGCTCTTTCTAGCAGATG | 86.7 | 0.8798 |
| 46078 | SCN9A_Int16_Int17_T8 | ATAGGTTTAGGACCTATATC | 86.5 | 0.9711 |
| 28773 | SCN9A_Int8_Int9_T7 | GCTAATGACCCAAGATTACT | 86.5 | 0.9112 |
| 46496 | SCN9A_Int15_Int16_T12 | ACATCTGGTTACATACCACC | 86.1 | 0.8996 |
| 27885 | SCN9A_Int11_Int12_T23 | GGTGTGGTCTCCCTGGTTGA | 86.1 | 0.9434 |

FIGURE 2C

| ID | Name | Sequence | Value1 | Value2 |
|---|---|---|---|---|
| 29928 | SCN9A_Int5_Int6_T2 | AATACCTTGACTAAAGGCTC | 86 | 0.8809 |
| 27933 | SCN9A_Int11_Int12_T7 | CAGTCACCACTCAGCATTCG | 85.9 | 0.9717 |
| 46039 | SCN9A_Int16_Int17_T2 | TTTTCCAAATCGGATTCCCC | 85.2 | 0.952 |
| 47439 | SCN9A_Int10_Int11_T10 | CAATTTGGGTGGTACCTGAT | 84 | 0.9863 |
| 28774 | SCN9A_Int8_Int9_T1 | GGCTAATGACCCAAGATTAC | 83.9 | 0.9273 |
| 47455 | SCN9A_Int10_Int11_T24 | AGCACTTTTAGAGCTCAGTT | 83.8 | 0.9811 |
| 30020 | SCN9A_Int2_Int5_T24 | TATGAAAGCTAGTCATTGAT | 83.5 | 0.8574 |
| 47236 | SCN9A_Int11_Int12_T15 | CTGTGCATTTTCCCGTTCAC | 83.1 | 0.9042 |
| 28089 | SCN9A_Int10_Int11_T3 | ACCTTGGTGTCGAAGGGCAT | 83.1 | 0.847 |
| 26813 | SCN9A_Int16_Int17_T14 | ATAGGTCCTAAACCTATTTC | 82.8 | 0.9369 |
| 47464 | SCN9A_Int10_Int11_T9 | GCCGCTGCAATTGCCTGGTT | 81.7 | 0.8389 |
| 28091 | SCN9A_Int10_Int11_T8 | GTTTCCACCTTGGTGTCGAA | 81.3 | 0.9816 |
| 29908 | SCN9A_Int5_Int6_T11 | AGTAATTGGTGTGAAGCATT | 81 | 0.8373 |
| 27892 | SCN9A_Int11_Int12_T12 | CCACCAATGCTGCCGGTGAA | 80.9 | 0.9922 |
| 28776 | SCN9A_Int8_Int9_T15 | GGGCCTTCTTAGCCTTGTTT | 80.9 | 0.827 |
| 28783 | SCN9A_Int8_Int9_T17 | ATTGGCAGAAACCCTGATTA | 80.9 | 0.934 |
| 27252 | SCN9A_Int15_Int16_T13 | GATCATTGGTAACTCAGTAG | 80.5 | 0.8174 |
| 29930 | SCN9A_Int5_Int6_T12 | GTAGAAAATACCTTGACTAA | 80.5 | 0.897 |
| 47625 | SCN9A_Int9_Int10_T1 | CCAGCAGCACGCAGCGTCTA | 80.2 | 0.9761 |
| 49945 | SCN9A_Int1_Int2_T16 | AGCAATGCGTTGTTCAATGA | 79.8 | 0.9753 |
| 30106 | SCN9A_Int2_Int5_T10 | ACCAAAAATGTCGAGTAAGT | 79.7 | 0.8658 |
| 48060 | SCN9A_Int8_Int9_T12 | TTGGGTCATTAGCCTAAACA | 79.6 | 0.9502 |
| 29831 | SCN9A_Int6_Int7_T8 | GATATAATGCATGACTTTCT | 79.5 | 0.8465 |
| 47239 | SCN9A_Int11_Int12_T10 | CCGTTCACCGGCAGCATTGG | 79.3 | 0.9666 |
| 49355 | SCN9A_Int2_Int5_T41 | TCATAAATGCAGTAACTTCC | 78.9 | 0.8446 |
| 26774 | SCN9A_Int16_Int17_T7 | CAGCGTGGACAAACACTTGA | 78.8 | 0.986 |

FIGURE 2D

| | | | | |
|---|---|---|---|---|
| 30050 | SCN9A_Int2_Int5_T15 | GTGTTTAGGTACACTTTTAC | 78.8 | 0.8501 |
| 47246 | SCN9A_Int11_Int12_T9 | TTACTGCTGCGTCGCTCCTG | 78.6 | 0.9339 |
| 27250 | SCN9A_Int15_Int16_T16 | GGTAACTCAGTAGGGGCTCT | 77.8 | 0.9081 |
| 49124 | SCN9A_Int5_Int6_T9 | ACACCAATTACTTCTTACCT | 77 | 0.7704 |
| 30053 | SCN9A_Int2_Int5_T22 | TTTCACATCTAGTATCCCAA | 76.9 | 0.8784 |
| 49362 | SCN9A_Int2_Int5_T11 | ACCCACTTACTCGACATTTT | 75.9 | 0.9543 |
| 47238 | SCN9A_Int11_Int12_T11 | TTCCCGTTCACCGGCAGCAT | 75.8 | 0.9612 |
| 49418 | SCN9A_Int2_Int5_T45 | AAGCAGGTGTGGCATTGAAA | 75.4 | 0.7977 |
| 27544 | SCN9A_Int13_Int14_T3 | ATGCCTGACTGATTTGTATC | 74.9 | 0.9498 |
| 46080 | SCN9A_Int16_Int17_T5 | GTTAGGACCTATATCAGGG | 74.8 | 0.982 |
| 26775 | SCN9A_Int16_Int17_T15 | CAGTGGTTTTGGAAGCAGCG | 73.7 | 0.9893 |
| 30079 | SCN9A_Int2_Int5_T4 | ATTTTTGATAGAAGCAATGT | 73.6 | 0.9499 |
| 48052 | SCN9A_Int8_Int9_T8 | TTCTCTTGGTACTCACCTGT | 73.1 | 0.8926 |
| 46081 | SCN9A_Int16_Int17_T6 | TTTAGGACCTATATCAGGGT | 72.6 | 0.8862 |
| 49424 | SCN9A_Int2_Int5_T40 | ATACTATGAAAGTCTGCAGG | 71.9 | 0.8943 |
| 47440 | SCN9A_Int10_Int11_T14 | AATTTGGGTGGTACCTGATT | 71.6 | 0.922 |
| 49331 | SCN9A_Int2_Int5_T36 | TGTGTAACATGTCTAAGAAC | 70.3 | 0.8103 |
| 30612 | SCN9A_Int1_Int2_T5 | ATGGCAATGTTGCCTCCCCC | 70.1 | 0.9169 |
| 47441 | SCN9A_Int10_Int11_T18 | ATTTGGGTGGTACCTGATTG | 69.9 | 0.9539 |
| 47626 | SCN9A_Int9_Int10_T7 | ACGCAGCGTCTAGGGAAAAA | 69.6 | 0.9564 |
| 49314 | SCN9A_Int2_Int5_T23 | GGAGGATGGCTGTTGGGTTA | 69.4 | 0.7808 |
| 27530 | SCN9A_Int13_Int14_T5 | TCTGGAATTGCTCTCCATAT | 67.9 | 0.8398 |
| 48081 | SCN9A_Int8_Int9_T14 | TTATAGGTGAGAGTGTCTTC | 67.9 | 0.7989 |
| 30065 | SCN9A_Int2_Int5_T42 | TAGACCTATTGTAGTTTAAT | 67.9 | 0.8691 |
| 46040 | SCN9A_Int16_Int17_T4 | TCGGATTCCCCAGGTGCAAT | 67.8 | 0.9378 |
| 49962 | SCN9A_Int1_Int2_T24 | AGCTCCTCACATAAGAGGCC | 67.2 | 0.9019 |

FIGURE 2E

| | | | | |
|---|---|---|---|---|
| 49976 | SCN9A_Int1_Int2_T14 | CTAGAATTATCAGCTTGTTA | 66.8 | 0.9416 |
| 27248 | SCN9A_Int15_Int16_T15 | AGGTAACCTCACCTTAGTGT | 64.9 | 0.9318 |
| 29814 | SCN9A_Int6_Int7_T2 | CTGAGTGTGTTTGCACTAAT | 64.6 | 0.9659 |
| 30162 | SCN9A_Int2_Int5_T25 | TGACATTGGAACCACATTGC | 64.1 | 0.6897 |
| 49302 | SCN9A_Int2_Int5_T33 | ACCTAAACACAAGATTCCAT | 62.5 | 0.7737 |
| 49366 | SCN9A_Int2_Int5_T1 | CATTTTTGGTCCAGTCCGGT | 62.5 | 0.8884 |
| 26764 | SCN9A_Int16_Int17_T1 | TGCACCTGGGGAATCCGATT | 62.2 | 0.8398 |
| 46082 | SCN9A_Int16_Int17_T11 | TTAGGACCTATATCAGGGTG | 60.9 | 0.9655 |
| 49048 | SCN9A_Int6_Int7_T1 | AAGCCCCTACAATTGTCTTC | 60.6 | 0.7797 |
| 28788 | SCN9A_Int8_Int9_T11 | CGTGTGTAGTCAGTGTCCAG | 60.3 | 0.663 |
| 47633 | SCN9A_Int9_Int10_T10 | CATGAGCAAATCTGACAGTT | 60.2 | 0.9542 |
| 49290 | SCN9A_Int2_Int5_T28 | CAAAATCCAGCCAGTTCCAC | 58 | 0.6231 |
| 27222 | SCN9A_Int15_Int16_T17 | TACATGATGGTCATGGTCAT | 57.5 | 0.859 |
| 30107 | SCN9A_Int2_Int5_T14 | GACCAAAAATGTCGAGTAAG | 57.3 | 0.8715 |
| 27336 | SCN9A_Int14_Int15_T3 | ATGAGTATTTCCAAGTAGGC | 56.2 | 0.9135 |
| 49142 | SCN9A_Int5_Int6_T3 | CTTACCTGAGCCTTTAGTCA | 55.5 | 0.8324 |
| 48073 | SCN9A_Int8_Int9_T4 | TTCACACAGGTGTACCCCTC | 55.3 | 0.8246 |
| 28305 | SCN9A_Int9_Int10_T9 | CTTTGTCGTAGTGATTTTCC | 55 | 0.9279 |
| 49145 | SCN9A_Int5_Int6_T4 | CAAGGTATTTTCTACGTTTG | 53.9 | 0.9381 |
| 30061 | SCN9A_Int2_Int5_T32 | CTCCAATATATGTCTTCCAG | 52.6 | 0.7103 |
| 47463 | SCN9A_Int10_Int11_T11 | TGCCGCTGCAATTGCCTGGT | 52.1 | 0.7771 |
| 48054 | SCN9A_Int8_Int9_T5 | TGGTACTCACCTGTTGGTAA | 52 | 0.9139 |
| 49365 | SCN9A_Int2_Int5_T6 | ACATTTTTGGTCCAGTCCGG | 51.6 | 0.664 |
| 27253 | SCN9A_Int15_Int16_T18 | AGATCATTGGTAACTCAGTA | 51.3 | 0.8976 |
| 49352 | SCN9A_Int2_Int5_T37 | AGCAAGCATATAACATGGGA | 51.2 | 0.6484 |
| 30110 | SCN9A_Int2_Int5_T2 | CCATGAATAACCCACCGGAC | 50.7 | 0.8218 |

FIGURE 2F

| | | | | |
|---|---|---|---|---|
| 27887 | | | | |
| | SCN9A_Int11_Int12_T14 | TGCTGTGGACTGCAACGGTG | 49.8 | 0.9532 |
| 47243 | | | | |
| | SCN9A_Int11_Int12_T17 | TTGGTGGGGACCTACTGGCT | 49.6 | 0.9388 |
| 27868 | | | | |
| | SCN9A_Int11_Int12_T25 | TTACATAGCTCAGGCATGGC | 48.5 | 0.7899 |
| 27891 | | | | |
| | SCN9A_Int11_Int12_T6 | CACCAATGCTGCCGGTGAAC | 48.4 | 0.8152 |
| 46834 | | | | |
| | SCN9A_Int13_Int14_T7 | CCAAGGTGGACATTTTTGTC | 48.2 | 0.9607 |
| 30043 | | | | |
| | SCN9A_Int2_Int5_T5 | TCACTTTTCTTCGTGACCCG | 47.6 | 0.9582 |
| 49944 | | | | |
| | SCN9A_Int1_Int2_T2 | CAGCAATGCGTTGTTCAATG | 46 | 0.9926 |
| 49316 | | | | |
| | SCN9A_Int2_Int5_T29 | ACACCCTATTAAACTACAAT | 45.3 | 0.9238 |
| 26767 | | | | |
| | SCN9A_Int16_Int17_T3 | GTGACAGTGCCAATTGCACC | 44.1 | 0.9752 |
| 28273 | | | | |
| | SCN9A_Int9_Int10_T3 | GAGGCTCTGCGGTATATGCT | 44 | 0.4837 |
| 47242 | | | | |
| | SCN9A_Int11_Int12_T13 | CAGCATTGGTGGGGACCTAC | 43.8 | 0.9894 |
| 47624 | | | | |
| | SCN9A_Int9_Int10_T2 | GCCAGCAGCACGCAGCGTCT | 41.1 | 0.9805 |
| 29811 | | | | |
| | SCN9A_Int6_Int7_T6 | ATTGGACTACAGCTGTTCAT | 40.8 | 0.429 |
| 49422 | | | | |
| | SCN9A_Int2_Int5_T27 | TCAATACTATGAAAGTCTGC | 40.1 | 0.9581 |
| 28081 | | | | |
| | SCN9A_Int10_Int11_T1 | TGCTAAATGTGTATCACCCG | 39.9 | 0.9746 |
| 46050 | | | | |
| | SCN9A_Int16_Int17_T17 | TGCTCATTTCAGCAAGTGTA | 38.5 | 0.9915 |
| 27870 | | | | |
| | SCN9A_Int11_Int12_T16 | AAGGACGTTTTACATAGCTC | 36.8 | 0.3684 |
| 47472 | | | | |
| | SCN9A_Int10_Int11_T15 | ATCCTAGGAAACCCTAGGAC | 36.6 | 0.9894 |
| 49952 | | | | |
| | SCN9A_Int1_Int2_T27 | TGGACAAAGCTCTGAGGTCC | 34.9 | 0.9874 |
| 28780 | | | | |
| | SCN9A_Int8_Int9_T9 | CGAGCTTTGACACTTTCAGC | 32.2 | 0.9531 |
| 46099 | | | | |
| | SCN9A_Int16_Int17_T13 | AAGTACACTTTTCCGAATAT | 29.8 | 0.9835 |
| 49143 | | | | |
| | SCN9A_Int5_Int6_T1 | GTCAAGGTATTTTCTACGTT | 27.6 | 0.8857 |
| 28150 | | | | |
| | SCN9A_Int10_Int11_T19 | CACCATGTTGTTATGCTAAT | 26 | 0.9945 |
| 27873 | | | | |
| | SCN9A_Int11_Int12_T4 | CAACTTCTGATGACAGCGTA | 25.8 | 0.9859 |
| 47244 | | | | |
| | SCN9A_Int11_Int12_T1 | TGTTACTGCTGCGTCGCTCC | 25.6 | 0.9923 |
| 30041 | | | | |
| | SCN9A_Int2_Int5_T7 | TCGTGACCCGTGGAACTGGC | 23.4 | 0.9831 |

FIGURE 2G

| 47604 | | | | |
|---|---|---|---|---|
| | SCN9A_Int9_Int10_T8 | TAGCTTCTTCAATGTTTGCC | 22.1 | 0.9675 |
| 49357 | | | | |
| | SCN9A_Int2_Int5_T43 | AAATGCAGTAACTTCCTGGC | 18.5 | 0.9816 |
| 28275 | | | | |
| | SCN9A_Int9_Int10_T5 | AATGCAAACGGTTACAACAG | 17.3 | 0.2165 |
| 28092 | | | | |
| | SCN9A_Int10_Int11_T5 | AGTTTCCACCTTGGTGTCGA | 16.1 | 0.9885 |
| 49283 | | | | |
| | SCN9A_Int2_Int5_T19 | CCCCAGAGGTTTGCTGTTAT | 12.2 | 0.9888 |
| 28141 | | | | |
| | SCN9A_Int10_Int11_T13 | TCATTTAAGTGTTAACGTCT | 10.2 | 0.9934 |
| 30628 | | | | |
| | SCN9A_Int1_Int2_T20 | TTTAATGGGCCTTTCTTGGC | 9.4 | 0.9392 |
| 46066 | | | | |
| | SCN9A_Int16_Int17_T12 | ATCTGGAGGTTGTTTGCATC | 8.7 | 0.9932 |
| 49364 | | | | |
| | SCN9A_Int2_Int5_T12 | TCGACATTTTTGGTCCAGTC | 8.5 | 0.989 |
| 28307 | | | | |
| | SCN9A_Int9_Int10_T4 | CCCTAGACGCTGCGTGCTGC | 5.1 | 0.9929 |
| 28143 | | | | |
| | SCN9A_Int10_Int11_T20 | TCCTAGGGTTTCCTAGGATT | 4.1 | 0.9928 |

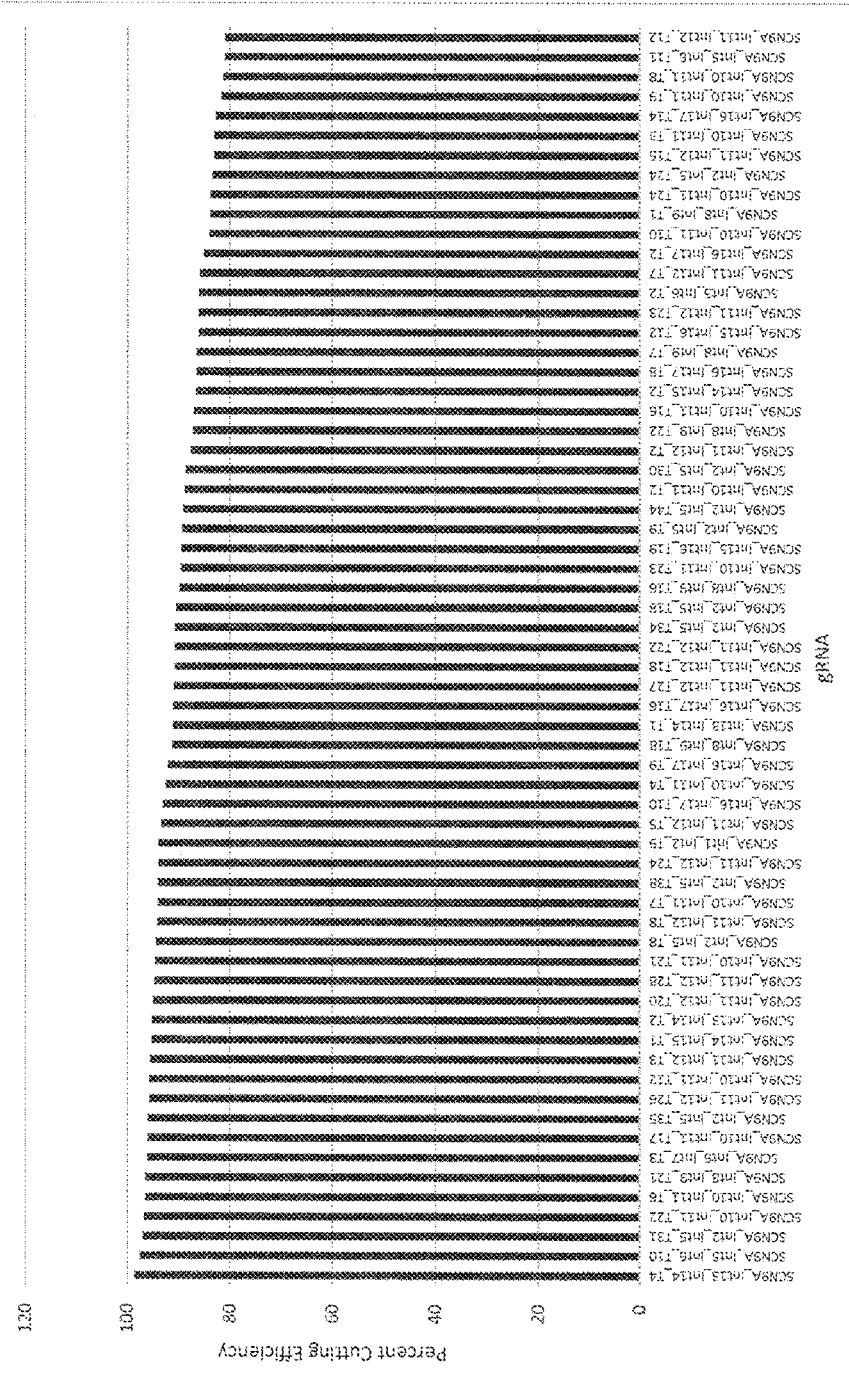

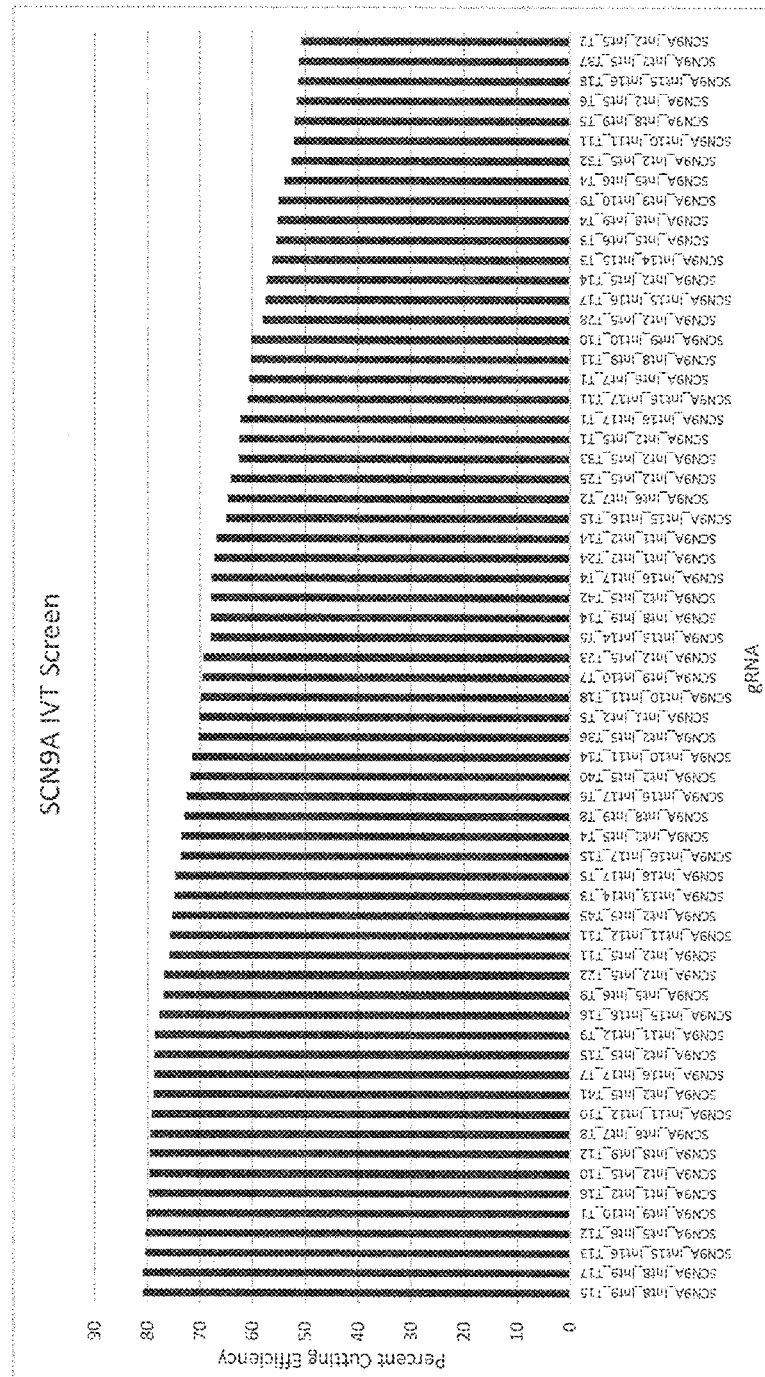

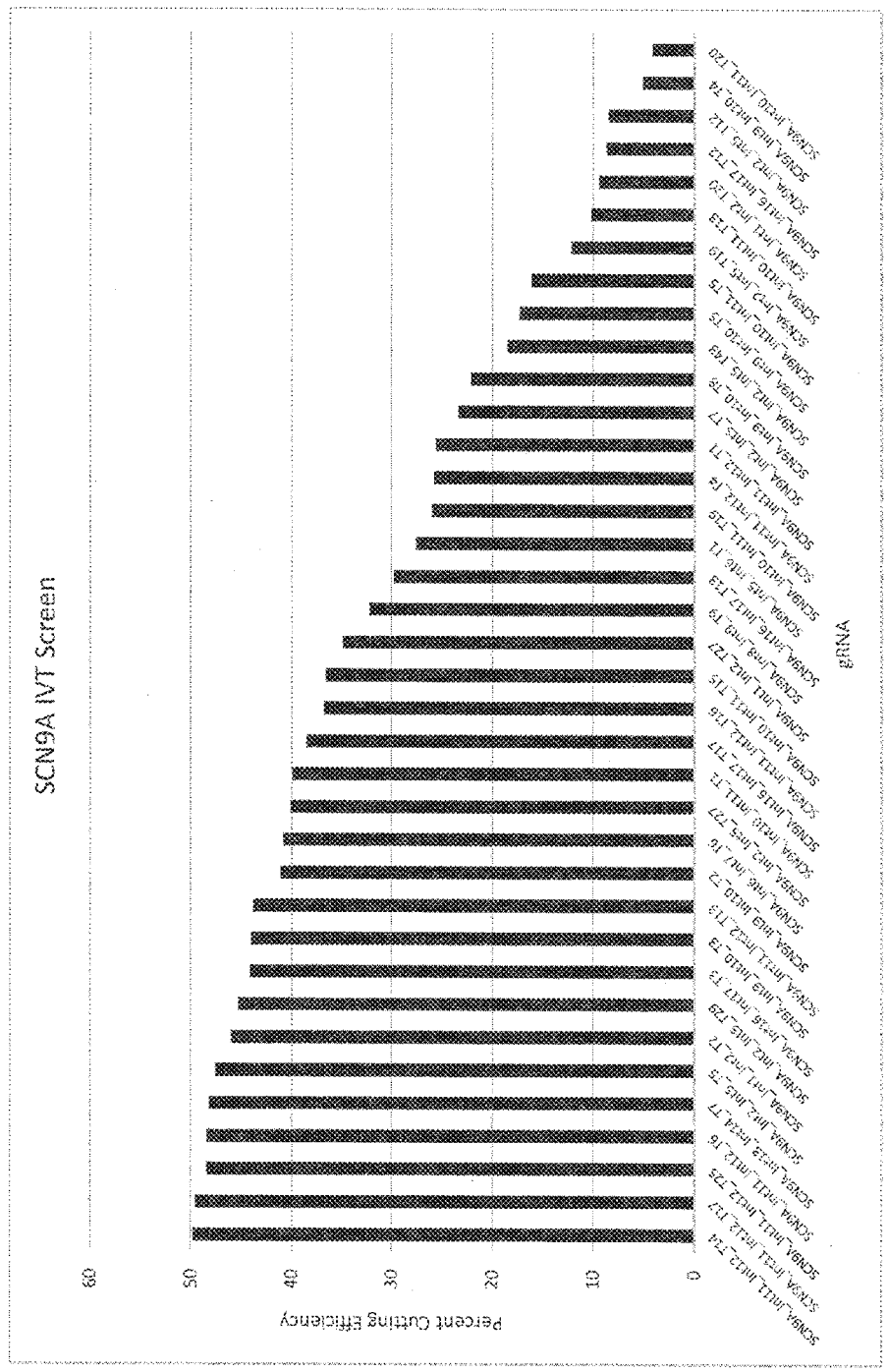

MATERIALS AND METHODS FOR TREATMENT OF PAIN RELATED DISORDERS

RELATED APPLICATIONS

This application is a national stage filing under 35 U.S.C. § 371 of international application number PCT/IB2017/054086, filed Jul. 6, 2017, which claims the benefit of U.S. Provisional Application No. 62/358,763 filed Jul. 6, 2016 and U.S. Provisional Application No. 62/461,874 filed Feb. 22, 2017, each of which are incorporated herein by reference in its entirety.

FIELD

The present disclosure relates to the field of gene editing and specifically to the alteration of the Sodium Voltage-Gated Channel Alpha Subunit 9 (SCN9A) gene.

INCORPORATION BY REFERENCE OF SEQUENCE LISTING

This application contains a Sequence Listing which has been filed electronically in ASCII format and is hereby incorporated herein by reference in its entirety. This ASCII copy, created on Dec. 31, 2018, is named C154270022US02-SEQ-YJC and is 48,746 kB in size.

BACKGROUND

Genome engineering refers to the strategies and techniques for the targeted, specific modification of the genetic information (genome) of living organisms. Genome engineering is a very active field of research because of the wide range of possible applications, particularly in the areas of human health. For example, genome engineering can be used to alter (e.g., correct or knock-out) a gene carrying a harmful mutation or to explore the function of a gene. Early technologies developed to insert a transgene into a living cell were often limited by the random nature of the insertion of the new sequence into the genome. Random insertions into the genome may result in disrupting normal regulation of neighboring genes leading to severe unwanted effects. Furthermore, random integration technologies offer little reproducibility, as there is no guarantee that the sequence would be inserted at the same place in two different cells. Recent genome engineering strategies, such as zinc finger nucleases (ZFNs), transcription activator like effector nucleases (TALENs), homing endonucleases (HEs) and MegaTALs, enable a specific area of the DNA to be modified, thereby increasing the precision of the alteration compared to early technologies. These newer platforms offer a much larger degree of reproducibility, but still have their limitations.

Despite efforts from researchers and medical professionals worldwide who have been trying to address genetic disorders, and despite the promise of genome engineering approaches, there still remains a critical need for developing safe and effective treatments involving SCN9A related indications.

By using genome engineering tools to create permanent changes to the genome that can address the SCN9A related disorders or conditions with as few as a single treatment, the resulting therapy may completely remedy certain SCN9A related indications and/or diseases.

SUMMARY

Provided herein are cellular, ex vivo and in vivo methods for creating permanent changes to the genome by introducing one or more insertions, deletions or mutations of at least one nucleotide within or near the Sodium Voltage-Gated Channel Alpha Subunit 9 (SCN9A) gene or other DNA sequences that encode regulatory elements of the SCN9A gene by genome editing and reducing or eliminating Sodium Voltage-Gated Channel Alpha Subunit 9 (SCN9A) gene products, which can be used to treat pain. Also provided performing herein are components and compositions, and vectors for performing such methods.

Provided herein is a method for editing a Sodium Voltage-Gated Channel Alpha Subunit 9 (SCN9A) gene in a cell by genome editing comprising: introducing into the cell one or more deoxyribonucleic acid (DNA) endonucleases to effect one or more single-strand breaks (SSBs) or double-strand breaks (DSBs) within or near the SCN9A gene or SCN9A regulatory elements that results in one or more permanent insertions, deletions or mutations of at least one nucleotide within or near the SCN9A gene, thereby reducing or eliminating the expression or function of SCN9A gene products.

Also provided herein is an ex vivo method for treating a patient having an SCN9A related condition or disorder comprising: editing a patient specific induced pluripotent stem cell (iPSC) within or near a Sodium Voltage-Gated Channel Alpha Subunit 9 (SCN9A) gene or other DNA sequences that encode regulatory elements of the SCN9A gene; differentiating the edited iPSC into a neuron of the peripheral nervous system; and administering the neuron of the peripheral nervous system to the patient.

In some aspects, the editing step comprises: introducing into the iPSC one or more deoxyribonucleic acid (DNA) endonucleases to effect one or more single-strand breaks (SSBs) or double-strand breaks (DSBs) within or near the SCN9A gene or SCN9A regulatory elements that results in one or more permanent insertions, deletions or mutations of at least one nucleotide within or near the SCN9A gene, thereby reducing or eliminating the expression or function of SCN9A gene products.

Also provided herein is an ex vivo method for treating a patient having an SCN9A related condition or disorder comprising: editing a mesenchymal stem cell within or near a Sodium Voltage-Gated Channel Alpha Subunit 9 (SCN9A) gene or other DNA sequences that encode regulatory elements of the SCN9A gene; differentiating the edited mesenchymal stem cell into a neuron of the peripheral nervous system; and administering the neuron of the peripheral nervous system to the patient.

In some aspects, the editing step comprises: introducing into the mesenchymal stem cell one or more deoxyribonucleic acid (DNA) endonucleases to effect one or more single-strand breaks (SSBs) or double-strand breaks (DSBs) within or near the SCN9A gene or SCN9A regulatory elements that results in one or more permanent insertions, deletions or mutations of at least one nucleotide within or near the SCN9A gene, thereby reducing or eliminating the expression or function of SCN9A gene products.

Also provided herein is an in vivo method for treating a patient with an SCN9A related disorder comprising: editing the Sodium Voltage-Gated Channel Alpha Subunit 9 (SCN9A) gene in a cell of the patient.

In some aspects, the editing step comprises: introducing into the cell one or more deoxyribonucleic acid (DNA) endonucleases to effect one or more single-strand breaks (SSBs) or double-strand breaks (DSBs) within or near the SCN9A gene or SCN9A regulatory elements that results in one or more permanent insertions, deletions or mutations of at least one nucleotide within or near the SCN9A gene, thereby reducing or eliminating the expression or function of SCN9A gene products.

In some aspects, the cell is a neuron of the peripheral nervous system. In some aspects, the one or more deoxyribonucleic acid (DNA) endonuclease is delivered to the neuron of the peripheral nervous system via direct intraganglionic or intraspinal injection, or intrathecal delivery.

Also provided herein is a method of altering the contiguous genomic sequence of an SCN9A gene in a cell comprising: contacting the cell with one or more deoxyribonucleic acid (DNA) endonuclease to effect one or more single-strand breaks (SSBs) or double-strand breaks (DSBs). In some aspects, the alteration of the contiguous genomic sequence occurs in one or more exons of the SCN9A gene.

In some aspects, the one or more deoxyribonucleic acid (DNA) endonuclease is selected from any of those in SEQ ID NOs: 1-620 and variants having at least 90% homology to any of the sequences listed in SEQ ID NOs: 1-620.

In some aspects, the one or more deoxyribonucleic acid (DNA) endonuclease is one or more protein or polypeptide. In some aspects, the one or more deoxyribonucleic acid (DNA) endonuclease is one or more polynucleotide encoding the one or more DNA endonuclease. In some aspects, the one or more deoxyribonucleic acid (DNA) endonuclease is one or more ribonucleic acid (RNA) encoding the one or more DNA endonuclease. In some aspects, the one or more ribonucleic acid (RNA) is one or more chemically modified RNA. In some aspects, the one or more ribonucleic acid (RNA) is chemically modified in the coding region. In some aspects, the one or more polynucleotide or one or more ribonucleic acid (RNA) is codon optimized.

In some aspects, the methods further comprise introducing into the cell one or more gRNA or one or more sgRNA. In some aspects, the one or more gRNA or one or more sgRNA comprises a spacer sequence that is complementary to a DNA sequence within or near the SCN9A gene. In some aspects, the one or more gRNA or one or more sgRNA is chemically modified. In some aspects, the one or more gRNA or one or more sgRNA is pre-complexed with the one or more deoxyribonucleic acid (DNA) endonuclease. In some aspects, the pre-complexing involves a covalent attachment of the one or more gRNA or one or more sgRNA to the one or more deoxyribonucleic acid (DNA) endonuclease.

In some aspects, the one or more deoxyribonucleic acid (DNA) endonuclease is formulated in a liposome or lipid nanoparticle. In some aspects, the one or more deoxyribonucleic acid (DNA) endonuclease is formulated in a liposome or lipid nanoparticle which also comprises the one or more gRNA or one or more sgRNA.

In some aspects, the one or more deoxyribonucleic acid (DNA) endonuclease is encoded in an AAV vector particle. In some aspects, the one or more gRNA or one or more sgRNA is encoded in an AAV vector particle. In some aspects, the one or more deoxyribonucleic acid (DNA) endonuclease is encoded in an AAV vector particle, which also encodes the one or more gRNA or one or more sgRNA. In some aspects, the AAV vector particle is selected from any of those disclosed in SEQ ID NOs: 4734-5302 and Table 2.

Also provided herein is a single-molecule guide RNA comprising: at least a spacer sequence that is an RNA sequence corresponding to any of SEQ ID NOs: 5305-125469. In some aspects, the single-molecule guide RNA further comprises a spacer extension region. In some aspects, the single-molecule guide RNA further comprises a tracrRNA extension region. In some aspects, the single-molecule guide RNA is chemically modified.

In some aspects, the single-molecule guide RNA is pre-complexed with a site-directed polypeptide. In some aspects, the site-directed polypeptide is a DNA endonuclease. In some aspects, the DNA endonuclease is a Cas9 or CPf1 endonuclease. In some aspects, the Cas9 or Cpf1 endonuclease is selected from a group consisting of: *S. pyogenes* Cas9, *S. aureus* Cas9, *N. meningitides* Cas9, *S. thermophilus* CRISPR1 Cas9, *S. thermophilus* CRISPR 3 Cas9, *T. denticola* Cas9, *L. bacterium* ND2006 Cpf1 and *Acidaminococcus* sp. BV3L6 Cpf1, and variants having at least 90% homology to these endonucleases. In some aspects, the Cas9 or Cpf1 endonuclease comprises one or more nuclear localization signals (NLSs). In some aspects, at least one NLS is at or within 50 amino acids of the amino-terminus of the Cas9 or Cpf1 endonuclease and/or at least one NLS is at or within 50 amino acids of the carboxy-terminus of the Cas9 or Cpf1 endonuclease.

Also provided herein is RNA encoding the single-molecule guide polynucleotide described herein.

Also provided herein is RNA encoding the CRISPR/Cas system described herein.

Also provided herein is a DNA encoding the single-molecule guide RNA described herein.

Also provided herein is a DNA encoding the CRISPR/Cas system described herein.

Also provided herein is a vector comprising a DNA encoding the single-molecule guide RNA or CRISPR/Cas system. In some aspects, the vector is a plasmid. In some aspects, the vector is an AAV vector particle, wherein the AAV vector serotype is selected from those listed in SEQ ID NOs: 4734-5302 or Table 2.

BRIEF DESCRIPTION OF THE DRAWINGS

Various aspects of materials and methods disclosed and described in this specification can be better understood by reference to the accompanying figures, in which:

FIG. 1A is a depiction of the type II CRISPR/Cas system including gRNA;

FIG. 1B is another depiction of the type II CRISPR/Cas system including sgRNA;

FIGS. 2A-G describe the cutting efficiencies of *S. pyogenes* gRNAs selected via an in-vitro transcribed (IVT) gRNA screen;

FIG. 2A describes the cutting efficiencies in the range of 93.3-98.5% of *S. pyogenes* gRNAs selected via an in-vitro transcribed (IVT) gRNA screen;

FIG. 2B describes the cutting efficiencies in the range of 86.1-93% of *S. pyogenes* gRNAs selected via an in-vitro transcribed (IVT) gRNA screen;

FIG. 2C describes the cutting efficiencies in the range of 78.8-86% of *S. pyogenes* gRNAs selected via an in-vitro transcribed (IVT) gRNA screen;

FIG. 2D describes the cutting efficiencies in the range of 67.2-78.8% of *S. pyogenes* gRNAs selected via an in-vitro transcribed (IVT) gRNA screen;

FIG. 2E describes the cutting efficiencies in the range of 50.7-66.8% of *S. pyogenes* gRNAs selected via an in-vitro transcribed (IVT) gRNA screen;

FIG. 2F describes the cutting efficiencies in the range of 23.4-49.8% of *S. pyogenes* gRNAs selected via an in-vitro transcribed (IVT) gRNA screen;

FIG. 2G describes the cutting efficiencies in the range of 4.1-22.1% of *S. pyogenes* gRNAs selected via an in-vitro transcribed (IVT) gRNA screen;

FIGS. 3A-C describe the cutting efficiency of *S. pyogenes* gRNAs in HEK293T cells targeting the SCN9A gene;

FIG. 3A describes the cutting efficiency in the range of 80.9-98.5% of *S. pyogenes* gRNAs in HEK293T cells targeting the SCN9A gene;

FIG. 3B describes the cutting efficiency in the range of 50.7-80.9% of *S. pyogenes* gRNAs in HEK293T cells targeting the SCN9A gene; and FIG. 3C describes the cutting efficiency in the range of 4.1-49.8% of *S. pyogenes* gRNAs in HEK293T cells targeting the SCN9A gene.

BRIEF DESCRIPTION OF SEQUENCE LISTING

Figure 1A:
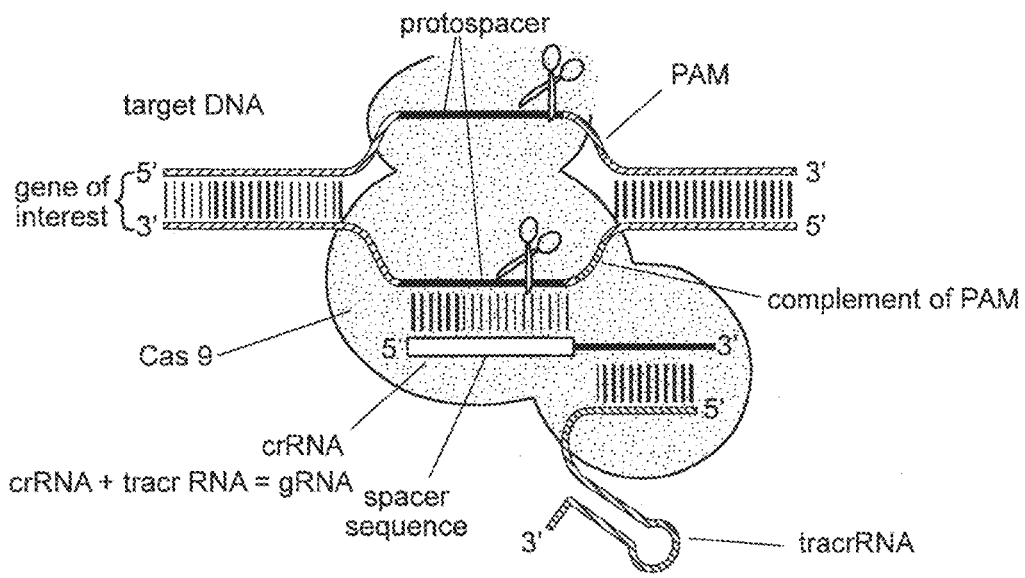
FIGS. 1A-B depict the type II CRISPR/Cas system.

SEQ ID NOs: 1-620 are Cas endonuclease ortholog sequences.
SEQ ID NOs: 621-631 do not include sequences.
SEQ ID NOs: 632-4715 are microRNA sequences.
SEQ ID NOs: 4716-4733 do not include sequences.
SEQ ID NOs: 4734-5302 are AAV serotype sequences.
SEQ ID NO: 5303 is a SCN9A nucleotide sequence.
SEQ ID NO: 5304 is a gene sequence including 1-5 kilobase pairs upstream and/or downstream of the SCN9A gene.
SEQ ID NOs: 5305-6250 are 20 bp spacer sequences for targeting within or near a SCN9A gene or other DNA sequence that encodes a regulatory element of the SCN9A gene with a *T. denticola* Cas9 endonuclease.
SEQ ID NOs: 6251-8561 are 20 bp spacer sequences for targeting within or near a SCN9A gene or other DNA sequence that encodes a regulatory element of the SCN9A gene with a *S. thermophilus* Cas9 endonuclease.
SEQ ID NOs: 8562-13614 are 20 bp spacer sequences for targeting within or near a SCN9A gene or other DNA sequence that encodes a regulatory element of the SCN9A gene with a *S. aureus* Cas9 endonuclease.
SEQ ID NOs: 13615-18988 are 20 bp spacer sequences for targeting within or near a SCN9A gene or other DNA sequence that encodes a regulatory element of the SCN9A gene with a *N. meningitides* Cas9 endonuclease.
SEQ ID NOs: 18989-56863 are 20 bp spacer sequences for targeting within or near a SCN9A gene or other DNA sequence that encodes a regulatory element of the SCN9A gene with a *S. pyogenes* Cas9 endonuclease.
SEQ ID NOs: 56864-125469 are 20 bp spacer sequences for targeting within or near a SCN9A gene or other DNA sequence that encodes a regulatory element of the SCN9A gene with an *Acidaminococcus*, a *Lachnospiraceae*, and a *Franciscella Novicida* Cpf1 endonuclease.
SEQ ID NOs: 125470-125499 do not include sequences.
SEQ ID NO: 125500 is a sample guide RNA (gRNA) for a *S. pyogenes* Cas9 endonuclease.
SEQ ID NOs: 125501-125503 show sample sgRNA sequences.

DETAILED DESCRIPTION

I. Introduction

Genome Editing

The present disclosure provides strategies and techniques for the targeted, specific alteration of the genetic information (genome) of living organisms. As used herein, the term "alteration" or "alteration of genetic information" refers to any change in the genome of a cell. In the context of treating genetic disorders, alterations may include, but are not limited to, insertion, deletion and correction. As used herein, the term "insertion" refers to an addition of one or more nucleotides in a DNA sequence. Insertions can range from small insertions of a few nucleotides to insertions of large segments such as a cDNA or a gene. The term "deletion" refers to a loss or removal of one or more nucleotides in a DNA sequence or a loss or removal of the function of a gene. In some cases, a deletion can include, for example, a loss of a few nucleotides, an exon, an intron, a gene segment, or the entire sequence of a gene. In some cases, deletion of a gene refers to the elimination or reduction of the function or expression of a gene or its gene product. This can result from not only a deletion of sequences within or near the gene, but also other events (e.g., insertion, nonsense mutation) that disrupt the expression of the gene. The term "correction" as used herein, refers to a change of one or more nucleotides of a genome in a cell, whether by insertion, deletion or substitution. Such correction may result in a more favorable genotypic or phenotypic outcome, whether in structure or function, to the genomic site which was corrected. One non-limiting example of a "correction" includes the correction of a mutant or defective sequence to a wild-type sequence which restores structure or function to a gene or its gene product(s). Depending on the nature of the mutation, correction may be achieved via various strategies disclosed herein. In one non-limiting example, a missense mutation may be corrected by replacing the region containing the mutation with its wild-type counterpart. As another example, duplication mutations (e.g., repeat expansions) in a gene may be corrected by removing the extra sequences.

In some aspects, alterations may also include a gene knock-in, knock-out or knock-down. As used herein, the term "knock-in" refers to an addition of a DNA sequence, or fragment thereof into a genome. Such DNA sequences to be knocked-in may include an entire gene or genes, may include regulatory sequences associated with a gene or any portion or fragment of the foregoing. For example, a cDNA encoding the wild-type protein may be inserted into the genome of a cell carrying a mutant gene. Knock-in strategies need not replace the defective gene, in whole or in part. In some cases, a knock-in strategy may further involve substitution of an existing sequence with the provided sequence, e.g., substitution of a mutant allele with a wild-type copy. On the other hand, the term "knock-out" refers to the elimination of a gene or the expression of a gene. For example, a gene can be knocked out by either a deletion or an addition of a nucleotide sequence that leads to a disruption of the reading frame. As another example, a gene may be knocked out by replacing a part of the gene with an irrelevant sequence. Finally, the term "knock-down" as used herein refers to reduction in the expression of a gene or its gene product(s). As a result of a gene knock-down, the protein activity or function may be attenuated or the protein levels may be reduced or eliminated.

Genome editing generally refers to the process of modifying the nucleotide sequence of a genome, preferably in a precise or pre-determined manner. Examples of methods of genome editing described herein include methods of using site-directed nucleases to cut deoxyribonucleic acid (DNA) at precise target locations in the genome, thereby creating single-strand or double-strand DNA breaks at particular locations within the genome. Such breaks can be and regularly are repaired by natural, endogenous cellular processes, such as homology-directed repair (HDR) and non-homologous end joining (NHEJ), as reviewed in Cox et al., Nature Medicine 21(2), 121-31 (2015). These two main DNA repair processes consist of a family of alternative pathways. NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor can be an exogenous nucleic acid, such as a plasmid, a single-strand oligonucleotide, a double-stranded oligonucleotide, a duplex oligonucleotide or a virus, that has regions of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ," in which the genetic outcome is similar to NHEJ in that small deletions and insertions can occur at the cleavage site. MMEJ can make use of homologous sequences of a few base pairs flanking the DNA break site to drive a more favored DNA end joining repair outcome, and recent reports have further elucidated the molecular mechanism of this process; see, e.g., Cho and Greenberg, Nature 518, 174-76 (2015); Kent et al., Nature Structural and Molecular Biology, Adv. Online doi:10.1038/nsmb.2961 (2015); Mateos-Gomez et al., Nature 518, 254-57 (2015); Ceccaldi et al., Nature 528, 258-62 (2015). In some instances, it may be possible to predict likely repair outcomes based on analysis of potential microhomologies at the site of the DNA break.

Each of these genome editing mechanisms can be used to create desired genomic alterations. A step in the genome editing process can be to create one or two DNA breaks, the latter as double-strand breaks or as two single-stranded breaks, in the target locus as near the site of intended mutation. This can be achieved via the use of site-directed polypeptides, as described and illustrated herein.

CRISPR Endonuclease System

A CRISPR (Clustered Regularly Interspaced Short Palindromic Repeats) genomic locus can be found in the genomes of many prokaryotes (e.g., bacteria and archaea). In prokaryotes, the CRISPR locus encodes products that function as a type of immune system to help defend the prokaryotes against foreign invaders, such as virus and phage. There are three stages of CRISPR locus function: integration of new sequences into the CRISPR locus, expression of CRISPR RNA (crRNA), and silencing of foreign invader nucleic acid. Five types of CRISPR systems (e.g., Type I, Type II, Type III, Type U, and Type V) have been identified.

A CRISPR locus includes a number of short repeating sequences referred to as "repeats." When expressed, the repeats can form secondary structures (e.g., hairpins) and/or comprise unstructured single-stranded sequences. The repeats usually occur in clusters and frequently diverge between species. The repeats are regularly interspaced with unique intervening sequences referred to as "spacers," resulting in a repeat-spacer-repeat locus architecture. The spacers are identical to or have high homology with known foreign invader sequences. A spacer-repeat unit encodes a crisprRNA (crRNA), which is processed into a mature form of the spacer-repeat unit. A crRNA comprises a "seed" or spacer sequence that is involved in targeting a target nucleic acid (in the naturally occurring form in prokaryotes, the spacer sequence targets the foreign invader nucleic acid). A spacer sequence is located at the 5' or 3' end of the crRNA.

A CRISPR locus also comprises polynucleotide sequences encoding CRISPR Associated (Cas) genes. Cas genes encode endonucleases involved in the biogenesis and the interference stages of crRNA function in prokaryotes. Some Cas genes comprise homologous secondary and/or tertiary structures.

Figure 1B:
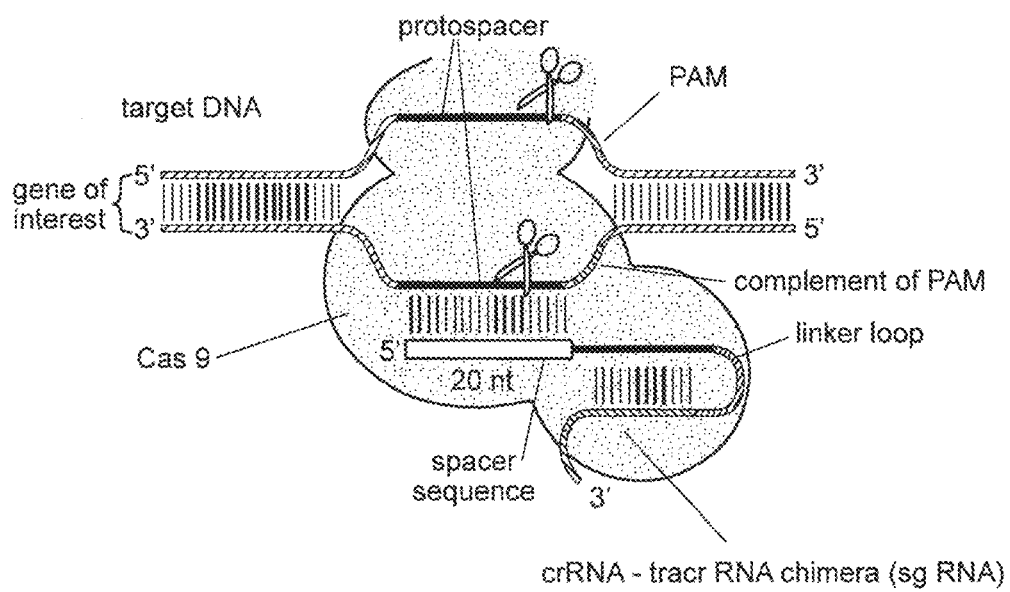

Type II CRISPR Systems crRNA biogenesis in a Type II CRISPR system in nature requires a trans-activating CRISPR RNA (tracrRNA). Non-limiting examples of Type II CRISPR systems are shown in FIGS. 1A and 1B. The tracrRNA can be modified by endogenous RNaseIII, and then hybridizes to a crRNA repeat in the pre-crRNA array. Endogenous RNaseIII can be recruited to cleave the pre-crRNA. Cleaved crRNAs can be subjected to exoribonuclease trimming to produce the mature crRNA form (e.g., 5' trimming). The tracrRNA can remain hybridized to the crRNA, and the tracrRNA and the crRNA associate with a site-directed polypeptide (e.g., Cas9). The crRNA of the crRNA-tracrRNA-Cas9 complex can guide the complex to a target nucleic acid to which the crRNA can hybridize. Hybridization of the crRNA to the target nucleic acid can activate Cas9 for targeted nucleic acid cleavage. The target nucleic acid in a Type II CRISPR system is referred to as a protospacer adjacent motif (PAM). In nature, the PAM is essential to facilitate binding of a site-directed polypeptide (e.g., Cas9) to the target nucleic acid. Type II systems (also referred to as Nmeni or CASS4) are further subdivided into Type II-A (CASS4) and II-B (CASS4a). Jinek et al., *Science,* 337(6096):816-821 (2012) showed that the CRISPR/Cas9 system is useful for RNA-programmable genome editing, and international patent application publication number WO2013/176772 provides numerous examples and applications of the CRISPR/Cas endonuclease system for site-specific gene editing.

Type V CRISPR Systems

Type V CRISPR systems have several important differences from Type II systems. For example, Cpf1 is a single RNA-guided endonuclease that, in contrast to Type II systems, lacks tracrRNA. In fact, Cpf1-associated CRISPR arrays can be processed into mature crRNAs without the requirement of an additional trans-activating tracrRNA. The Type V CRISPR array can be processed into short mature crRNAs of 42-44 nucleotides in length, with each mature crRNA beginning with 19 nucleotides of direct repeat followed by 23-25 nucleotides of spacer sequence. In contrast, mature crRNAs in Type II systems can start with 20-24 nucleotides of spacer sequence followed by about 22 nucleotides of direct repeat. Also, Cpf1 can utilize a T-rich protospacer-adjacent motif such that Cpf1-crRNA complexes efficiently cleave target DNA preceded by a short T-rich PAM, which is in contrast to the G-rich PAM following the target DNA for Type II systems. Thus, Type V systems cleave at a point that is distant from the PAM, while Type II systems cleave at a point that is adjacent to the PAM. In addition, in contrast to Type II systems, Cpf1 cleaves DNA via a staggered DNA double-stranded break with a 4 or 5 nucleotide 5' overhang. Type II systems cleave via a blunt double-stranded break. Similar to Type II systems, Cpf1 contains a predicted RuvC-like endonuclease domain, but lacks a second HNH endonuclease domain, which is in contrast to Type II systems.

Cas Genes/Polypeptides and Protospacer Adjacent Motifs

Exemplary CRISPR/Cas polypeptides include the Cas9 polypeptides as published in Fonfara et al., *Nucleic Acids Research,* 42: 2577-2590 (2014). The CRISPR/Cas gene naming system has undergone extensive rewriting since the Cas genes were discovered. Fonfara et al. also provides PAM sequences for the Cas9 polypeptides from various species (see also Table 1 infra).

II. Compositions and Methods of the Disclosure

Provided herein are cellular, ex vivo and in vivo methods for using genome engineering tools to create permanent changes to the genome by deleting or mutating the SCN9A gene or other DNA sequences that encode regulatory elements of the SCN9A gene. Such methods use endonucleases, such as CRISPR-associated (Cas9, Cpf1 and the like) nucleases, to permanently edit within or near the genomic locus of the SCN9A gene or other DNA sequences that encode regulatory elements of the SCN9A gene. In this way, examples set forth in the present disclosure can help to reduce or eliminate the expression of the SCN9A gene with as few as a single treatment (rather than deliver potential therapies for the lifetime of the patient).

Site-Directed Polypeptides (Endonucleases, Enzymes)

A site-directed polypeptide is a nuclease used in genome editing to cleave DNA. The site-directed polypeptide can be administered to a cell or a patient as either: one or more polypeptides, or one or more mRNAs encoding the polypeptide. Any of the enzymes or orthologs listed in SEQ ID NOs: 1-620, or disclosed herein, may be utilized in the methods herein. Single-molecule guide RNA can be pre-complexed with a site-directed polypeptide. The site-directed polypeptide can be any of the DNA endonuclease disclosed herein.

In the context of a CRISPR/Cas9 or CRISPR/Cpf1 system, the site-directed polypeptide can bind to a guide RNA that, in turn, specifies the site in the target DNA to which the polypeptide is directed. In the CRISPR/Cas9 or CRISPR/Cpf1 systems disclosed herein, the site-directed polypeptide can be an endonuclease, such as a DNA endonuclease.

A site-directed polypeptide can comprise a plurality of nucleic acid-cleaving (i.e., nuclease) domains. Two or more nucleic acid-cleaving domains can be linked together via a linker. For example, the linker can comprise a flexible linker. Linkers can comprise 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length.

Naturally-occurring wild-type Cas9 enzymes comprise two nuclease domains, a HNH nuclease domain and a RuvC domain. Herein, the term "Cas9" refers to both a naturally-occurring and a recombinant Cas9. Cas9 enzymes contemplated herein can comprise a HNH or HNH-like nuclease domain, and/or a RuvC or RuvC-like nuclease domain.

HNH or HNH-like domains comprise a McrA-like fold. HNH or HNH-like domains comprises two antiparallel β-strands and an α-helix. HNH or HNH-like domains comprises a metal binding site (e.g., a divalent cation binding site). HNH or HNH-like domains can cleave one strand of a target nucleic acid (e.g., the complementary strand of the crRNA targeted strand).

RuvC or RuvC-like domains comprise an RNaseH or RNaseH-like fold. RuvC/RNaseH domains are involved in a diverse set of nucleic acid-based functions including acting on both RNA and DNA. The RNaseH domain comprises 5 β-strands surrounded by a plurality of α-helices. RuvC/RNaseH or RuvC/RNaseH-like domains comprise a metal binding site (e.g., a divalent cation binding site). RuvC/RNaseH or RuvC/RNaseH-like domains can cleave one strand of a target nucleic acid (e.g., the non-complementary strand of a double-stranded target DNA).

Site-directed polypeptides can introduce double-strand breaks or single-strand breaks in nucleic acids, e.g., genomic DNA. The double-strand break can stimulate a cell's endogenous DNA-repair pathways (e.g., homology-dependent repair (HDR) or NHEJ or alternative non-homologous end joining (A-NHEJ) or microhomology-mediated end joining (MMEJ)). NHEJ can repair cleaved target nucleic acid without the need for a homologous template. This can sometimes result in small deletions or insertions (indels) in the target nucleic acid at the site of cleavage, and can lead to disruption or alteration of gene expression. HDR can occur when a homologous repair template, or donor, is available. The homologous donor template can comprise sequences that are homologous to sequences flanking the target nucleic acid cleavage site. The sister chromatid can be used by the cell as the repair template. However, for the purposes of genome editing, the repair template can be supplied as an exogenous nucleic acid, such as a plasmid, duplex oligonucleotide, single-strand oligonucleotide or viral nucleic acid. With exogenous donor templates, an additional nucleic acid sequence (such as a transgene) or modification (such as a single or multiple base change or a deletion) can be introduced between the flanking regions of homology so that the additional or altered nucleic acid sequence also becomes incorporated into the target locus. MMEJ can result in a genetic outcome that is similar to NHEJ in that small deletions and insertions can occur at the cleavage site. MMEJ can make use of homologous sequences of a few base pairs flanking the cleavage site to drive a favored end-joining DNA repair outcome. In some instances, it may be possible to predict likely repair outcomes based on analysis of potential microhomologies in the nuclease target regions.

Thus, in some cases, homologous recombination can be used to insert an exogenous polynucleotide sequence into the target nucleic acid cleavage site. An exogenous polynucleotide sequence is termed a "donor polynucleotide" (or donor or donor sequence) herein. The donor polynucleotide, a portion of the donor polynucleotide, a copy of the donor polynucleotide, or a portion of a copy of the donor polynucleotide can be inserted into the target nucleic acid cleavage site. The donor polynucleotide can be an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

The site-directed polypeptide can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary site-directed polypeptide [e.g., Cas9 from *S. pyogenes*, US2014/0068797 Sequence ID No. 8 or Sapranauskas et al., *Nucleic Acids Res*, 39(21): 9275-9282 (2011)], and various other site-directed polypeptides. The site-directed polypeptide can comprise at least 70, 75, 80, 85, 90, 95, 97, 99, or 100% identity to a wild-type site-directed polypeptide (e.g., Cas9 from *S. pyogenes*, supra) over 10 contiguous amino acids. The site-directed polypeptide can comprise at most: 70, 75, 80, 85, 90, 95, 97, 99, or 100% identity to a wild-type site-directed polypeptide (e.g., Cas9 from *S. pyogenes*, supra) over 10 contiguous amino acids. The site-directed polypeptide can comprise at least: 70, 75, 80, 85, 90, 95, 97, 99, or 100% identity to a wild-type site-directed polypeptide (e.g., Cas9 from *S. pyogenes*, supra) over 10 contiguous amino acids in a HNH nuclease domain of the site-directed polypeptide. The site-directed polypeptide can comprise at most: 70, 75, 80, 85, 90, 95, 97, 99, or 100% identity to a wild-type site-directed polypeptide (e.g., Cas9 from *S. pyogenes*, supra) over 10 contiguous amino acids in a HNH nuclease domain of the site-directed polypeptide. The site-directed polypeptide can comprise at least: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide. The site-directed polypeptide can comprise at most: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide.

The site-directed polypeptide can comprise a modified form of a wild-type exemplary site-directed polypeptide. The modified form of the wild-type exemplary site-directed polypeptide can comprise a mutation that reduces the nucleic acid-cleaving activity of the site-directed polypeptide. The modified form of the wild-type exemplary site-directed polypeptide can have less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary site-directed polypeptide (e.g., Cas9 from *S. pyogenes*, supra). The modified form of the site-directed polypeptide can have no substantial nucleic acid-cleaving activity. When a site-directed polypeptide is a modified form that has no substantial nucleic acid-cleaving activity, it is referred to herein as "enzymatically inactive."

The modified form of the site-directed polypeptide can comprise a mutation such that it can induce a single-strand break (SSB) on a target nucleic acid (e.g., by cutting only one of the sugar-phosphate backbones of a double-strand target nucleic acid). In some aspects, the mutation can result in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type site directed polypeptide (e.g., Cas9 from *S. pyogenes*, supra). In some aspects, the mutation can result in one or more of the plurality of nucleic acid-cleaving domains retaining the ability to cleave the complementary strand of the target nucleic acid, but reducing its ability to cleave the non-complementary strand of the target nucleic acid. The mutation can result in one or more of the plurality of nucleic acid-cleaving domains retaining the ability to cleave the non-complementary strand of the target nucleic acid, but reducing its ability to cleave the complementary strand of the target nucleic acid. For example, residues in the wild-type exemplary *S. pyogenes* Cas9 polypeptide, such as Asp10, His840, Asn854 and Asn856, are mutated to inactivate one or more of the plurality of nucleic acid-cleaving domains (e.g., nuclease domains). The residues to be mutated can correspond to residues Asp10, His840, Asn854 and Asn856 in the wild-type exemplary *S. pyogenes* Cas9 polypeptide (e.g., as determined by sequence and/or structural alignment). Non-limiting examples of mutations include D10A, H840A, N854A or N856A. One skilled in the art will recognize that mutations other than alanine substitutions can be suitable.

In some aspects, a D10A mutation can be combined with one or more of H840A, N854A, or N856A mutations to produce a site-directed polypeptide substantially lacking DNA cleavage activity. A H840A mutation can be combined with one or more of D10A, N854A, or N856A mutations to produce a site-directed polypeptide substantially lacking DNA cleavage activity. A N854A mutation can be combined with one or more of H840A, D10A, or N856A mutations to produce a site-directed polypeptide substantially lacking DNA cleavage activity. A N856A mutation can be combined with one or more of H840A, N854A, or D10A mutations to produce a site-directed polypeptide substantially lacking DNA cleavage activity. Site-directed polypeptides that comprise one substantially inactive nuclease domain are referred to as "nickases."

Nickase variants of RNA-guided endonucleases, for example Cas9, can be used to increase the specificity of CRISPR-mediated genome editing. Wild type Cas9 is typically guided by a single guide RNA designed to hybridize with a specified ~20 nucleotide sequence in the target sequence (such as an endogenous genomic locus). However, several mismatches can be tolerated between the guide RNA and the target locus, effectively reducing the length of required homology in the target site to, for example, as little as 13 nt of homology, and thereby resulting in elevated potential for binding and double-strand nucleic acid cleavage by the CRISPR/Cas9 complex elsewhere in the target genome—also known as off-target cleavage. Because nickase variants of Cas9 each only cut one strand, in order to create a double-strand break it is necessary for a pair of nickases to bind in close proximity and on opposite strands of the target nucleic acid, thereby creating a pair of nicks, which is the equivalent of a double-strand break. This requires that two separate guide RNAs—one for each nickase—must bind in close proximity and on opposite strands of the target nucleic acid. This requirement essentially doubles the minimum length of homology needed for the double-strand break to occur, thereby reducing the likelihood that a double-strand cleavage event will occur elsewhere in the genome, where the two guide RNA sites—if they exist—are unlikely to be sufficiently close to each other to enable the double-strand break to form. As described in the art, nickases can also be used to promote HDR versus NHEJ. HDR can be used to introduce selected changes into target sites in the genome through the use of specific donor sequences that effectively mediate the desired changes.

Mutations contemplated can include substitutions, additions, and deletions, or any combination thereof. The mutation converts the mutated amino acid to alanine. The mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagine, glutamine, histidine, lysine, or arginine). The mutation converts the mutated amino acid to a non-natural amino acid (e.g., selenomethionine). The mutation converts the mutated amino acid to amino acid mimics (e.g., phosphomimics). The mutation can be a conservative mutation. For example, the mutation converts the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). The mutation can cause a shift in reading frame and/or the creation of a premature stop codon. Mutations can cause changes to regulatory regions of genes or loci that affect expression of one or more genes.

The site-directed polypeptide (e.g., variant, mutated, enzymatically inactive and/or conditionally enzymatically inactive site-directed polypeptide) can target nucleic acid.

The site-directed polypeptide (e.g., variant, mutated, enzymatically inactive and/or conditionally enzymatically inactive endoribonuclease) can target DNA. The site-directed polypeptide (e.g., variant, mutated, enzymatically inactive and/or conditionally enzymatically inactive endoribonuclease) can target RNA.

The site-directed polypeptide can comprise one or more non-native sequences (e.g., the site-directed polypeptide is a fusion protein).

The site-directed polypeptide can comprise an amino acid sequence comprising at least 15% amino acid identity to a Cas9 from a bacterium (e.g., *S. pyogenes*), a nucleic acid binding domain, and two nucleic acid cleaving domains (i.e., a HNH domain and a RuvC domain).

The site-directed polypeptide can comprise an amino acid sequence comprising at least 15% amino acid identity to a Cas9 from a bacterium (e.g., *S. pyogenes*), and two nucleic acid cleaving domains (i.e., a HNH domain and a RuvC domain).

The site-directed polypeptide can comprise an amino acid sequence comprising at least 15% amino acid identity to a Cas9 from a bacterium (e.g., *S. pyogenes*), and two nucleic acid cleaving domains, wherein one or both of the nucleic acid cleaving domains comprise at least 50% amino acid identity to a nuclease domain from Cas9 from a bacterium (e.g., *S. pyogenes*).

The site-directed polypeptide can comprise an amino acid sequence comprising at least 15% amino acid identity to a Cas9 from a bacterium (e.g., *S. pyogenes*), two nucleic acid cleaving domains (i.e., a HNH domain and a RuvC domain), and a non-native sequence (for example, a nuclear localization signal) or a linker linking the site-directed polypeptide to a non-native sequence.

The site-directed polypeptide can comprise an amino acid sequence comprising at least 15% amino acid identity to a Cas9 from a bacterium (e.g., *S. pyogenes*), two nucleic acid cleaving domains (i.e., a HNH domain and a RuvC domain), wherein the site-directed polypeptide comprises a mutation in one or both of the nucleic acid cleaving domains that reduces the cleaving activity of the nuclease domains by at least 50%.

The site-directed polypeptide can comprise an amino acid sequence comprising at least 15% amino acid identity to a Cas9 from a bacterium (e.g., *S. pyogenes*), and two nucleic acid cleaving domains (i.e., a HNH domain and a RuvC domain), wherein one of the nuclease domains comprises mutation of aspartic acid 10, and/or wherein one of the nuclease domains can comprise a mutation of histidine 840, and wherein the mutation reduces the cleaving activity of the nuclease domain(s) by at least 50%.

The one or more site-directed polypeptides, e.g. DNA endonucleases, can comprise two nickases that together effect one double-strand break at a specific locus in the genome, or four nickases that together effect or cause two double-strand breaks at specific loci in the genome. Alternatively, one site-directed polypeptide, e.g. DNA endonuclease, can effect or cause one double-strand break at a specific locus in the genome.

Non-limiting examples of Cas9 orthologs from other bacterial strains include but are not limited to, Cas proteins identified in *Acaryochloris marina* MBIC11017; *Acetohalobium arabaticum* DSM 5501; *Acidithiobacillus caldus*; *Acidithiobacillus ferrooxidans* ATCC 23270; *Alicyclobacillus acidocaldarius* LAA1; *Alicyclobacillus acidocaldarius* subsp. *acidocaldarius* DSM 446; *Allochromatium vinosum* DSM 180; *Ammonifex degensii* KC4; *Anabaena variabilis* ATCC 29413; *Arthrospira maxima* CS-328; *Arthrospira platensis* str. *Paraca*; *Arthrospira* sp. PCC 8005; *Bacillus pseudomycoides* DSM 12442; *Bacillus selenitireducens* MLS10; *Burkholderiales bacterium* 1_1_47; *Caldicelulosiruptor becscii* DSM 6725; *Candidatus Desulforudis audaxviator* MP104C; *Caldicellulosiruptor hydrothermalis*_108; *Clostridium phage* c-st; *Clostridium botulinum* A3 str. Loch Maree; *Clostridium botulinum* Ba4 str. 657; *Clostridium difficile* QCD-63q42; *Crocosphaera watsonii* WH 8501; *Cyanothece* sp. ATCC 51142; *Cyanothece* sp. CCY0110; *Cyanothece* sp. PCC 7424; *Cyanothece* sp. PCC 7822; *Exiguobacterium sibiricum* 255-15; *Finegoldia magna* ATCC 29328; *Ktedonobacter racemifer* DSM 44963; *Lactobacillus delbrueckii* subsp. *bulgaricus* PB2003/044-T3-4; *Lactobacillus salivarius* ATCC 11741; *Listeria innocua*; *Lyngbya* sp. PCC 8106; *Marinobacter* sp. ELB17; *Methanohalobium evestigatum* Z-7303; *Microcystis phage* Ma-LMM01; *Microcystis aeruginosa* NIES-843; *Microscilla marina* ATCC 23134; *Microcoleus chthonoplastes* PCC 7420; *Neisseria meningitidis*; *Nitrosococcus halophilus* Nc4; *Nocardiopsis dassonvillei* subsp. *dassonvillei* DSM 43111; *Nodularia spumigena* CCY9414; *Nostoc* sp. PCC 7120; *Oscillatoria* sp. PCC 6506; *Pelotomaculum_thermopropionicum*_SI; *Petrotoga mobilis* SJ95; *Polaromonas naphthalenivorans* CJ2; *Polaromonas* sp. JS666; *Pseudoalteromonas haloplanktis* TAC125; *Streptomyces pristinaespiralis* ATCC 25486; *Streptomyces pristinaespiralis* ATCC 25486; *Streptococcus thermophilus*; *Streptomyces viridochromogenes* DSM 40736; *Streptosporangium roseum* DSM 43021; *Synechococcus* sp. PCC 7335; and *Thermosipho africanus* TCF52B (Chylinski et al., *RNA Biol.*, 2013; 10(5): 726-737).

In addition to Cas9 orthologs, other Cas9 variants such as fusion proteins of inactive dCas9 and effector domains with different functions may be served as a platform for genetic modulation. Any of the foregoing enzymes may be useful in the present disclosure.

Further examples of endonucleases that may be utilized in the present disclosure are given in SEQ ID NOs: 1-620. These proteins may be modified before use or may be encoded in a nucleic acid sequence such as a DNA, RNA or mRNA or within a vector construct such as the plasmids or AAV vectors taught herein. Further, they may be codon optimized.

SEQ ID NOs: 1-620 disclose a non-exhaustive listing of endonuclease sequences.

Genome-Targeting Nucleic Acid

The present disclosure provides a genome-targeting nucleic acid that can direct the activities of an associated polypeptide (e.g., a site-directed polypeptide) to a specific target sequence within a target nucleic acid. The genome-targeting nucleic acid can be an RNA. A genome-targeting RNA is referred to as a "guide RNA" or "gRNA" herein. A guide RNA can comprise at least a spacer sequence that hybridizes to a target nucleic acid sequence of interest, and a CRISPR repeat sequence. In Type II systems, the gRNA also comprises a second RNA called the tracrRNA sequence. In the Type II guide RNA (gRNA), the CRISPR repeat sequence and tracrRNA sequence hybridize to each other to form a duplex. In the Type V guide RNA (gRNA), the crRNA forms a duplex. In both systems, the duplex can bind a site-directed polypeptide, such that the guide RNA and site-direct polypeptide form a complex. The genome-targeting nucleic acid can provide target specificity to the complex by virtue of its association with the site-directed polypeptide. The genome-targeting nucleic acid thus can direct the activity of the site-directed polypeptide.

Exemplary guide RNAs include the spacer sequences in SEQ ID NOs: 5305-125469 of the Sequence Listing. As is understood by the person of ordinary skill in the art, each guide RNA can be designed to include a spacer sequence complementary to its genomic target sequence. For example, each of the spacer sequences in SEQ ID NOs: 5305-125469 of the Sequence Listing can be put into a single RNA chimera or a crRNA (along with a corresponding tracrRNA). See Jinek et al., Science, 337, 816-821 (2012) and Deltcheva et al., Nature, 471, 602-607 (2011).

The genome-targeting nucleic acid can be a double-molecule guide RNA. The genome-targeting nucleic acid can be a single-molecule guide RNA.

A double-molecule guide RNA can comprise two strands of RNA. The first strand comprises in the 5' to 3' direction, an optional spacer extension sequence, a spacer sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) in a Type II system can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

The sgRNA can comprise a 20 nucleotide spacer sequence at the 5' end of the sgRNA sequence. The sgRNA can comprise a less than a 20 nucleotide spacer sequence at the 5' end of the sgRNA sequence. The sgRNA can comprise a more than 20 nucleotide spacer sequence at the 5' end of the sgRNA sequence. The sgRNA can comprise a variable length spacer sequence with 17-30 nucleotides at the 5' end of the sgRNA sequence (see Table 1).

The sgRNA can comprise no uracil at the 3' end of the sgRNA sequence, such as in SEQ ID NO: 125502 of Table 1. The sgRNA can comprise one or more uracil at the 3' end of the sgRNA sequence, such as in SEQ ID NO: 125503 in Table 1. For example, the sgRNA can comprise 1 uracil (U) at the 3' end of the sgRNA sequence. The sgRNA can comprise 2 uracil (UU) at the 3' end of the sgRNA sequence. The sgRNA can comprise 3 uracil (UUU) at the 3' end of the sgRNA sequence. The sgRNA can comprise 4 uracil (UUUU) at the 3' end of the sgRNA sequence. The sgRNA can comprise 5 uracil (UUUUU) at the 3' end of the sgRNA sequence. The sgRNA can comprise 6 uracil (UUUUUU) at the 3' end of the sgRNA sequence. The sgRNA can comprise 7 uracil (UUUUUUU) at the 3' end of the sgRNA sequence. The sgRNA can comprise 8 uracil (UUUUUUUU) at the 3' end of the sgRNA sequence.

The sgRNA can be unmodified or modified. For example, modified sgRNAs can comprise one or more 2'-O-methyl phosphorothioate nucleotides.

TABLE 1

| SEQ ID NO. | sgRNA sequence |
|---|---|
| 125501 | nnnnnnnnnnnnnnnnnnnnguuuuagagcuagaaauag caaguuaaaauaaggcuaguccguuaucaacuugaaaaa guggcaccgagucggugcuuuu |

TABLE 1-continued

| SEQ ID NO. | sgRNA sequence |
|---|---|
| 125502 | nnnnnnnnnnnnnnnnnnnnguuuuagagcuagaaauag caaguuaaaauaaggcuaguccguuaucaacuugaaaaa guggcaccgagucggugc |
| 125503 | $n_{(17-30)}$guuuuagagcuagaaauagcaaguuaaaauaag gcuaguccguuaucaacuugaaaaaguggcaccgaguc ggugcu$_{(1-8)}$ |

A single-molecule guide RNA (sgRNA) in a Type V system can comprise, in the 5' to 3' direction, a minimum CRISPR repeat sequence and a spacer sequence.

By way of illustration, guide RNAs used in the CRISPR/Cas9 or CRISPR/Cpf1 system, or other smaller RNAs can be readily synthesized by chemical means, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

Spacer Extension Sequence

In some examples of genome-targeting nucleic acids, a spacer extension sequence can modify activity, provide stability and/or provide a location for modifications of a genome-targeting nucleic acid. A spacer extension sequence can modify on- or off-target activity or specificity. In some examples, a spacer extension sequence can be provided. The spacer extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. The spacer extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000 or more nucleotides. The spacer extension sequence can be less than 10 nucleotides in length. The spacer extension sequence can be between 10-30 nucleotides in length. The spacer extension sequence can be between 30-70 nucleotides in length.

The spacer extension sequence can comprise another moiety (e.g., a stability control sequence, an endoribonuclease binding sequence, a ribozyme). The moiety can decrease or increase the stability of a nucleic acid targeting nucleic acid. The moiety can be a transcriptional terminator segment (i.e., a transcription termination sequence). The moiety can function in a eukaryotic cell. The moiety can function in a prokaryotic cell. The moiety can function in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

Spacer Sequence

The spacer sequence hybridizes to a sequence in a target nucleic acid of interest. The spacer of a genome-targeting nucleic acid can interact with a target nucleic acid in a sequence-specific manner via hybridization (i.e., base pairing). The nucleotide sequence of the spacer can vary depending on the sequence of the target nucleic acid of interest.

In a CRISPR/Cas system herein, the spacer sequence can be designed to hybridize to a target nucleic acid that is located 5' of a PAM of the Cas9 enzyme used in the system. The spacer may perfectly match the target sequence or may have mismatches. Each Cas9 enzyme has a particular PAM sequence that it recognizes in a target DNA. For example, *S. pyogenes* recognizes in a target nucleic acid a PAM that comprises the sequence 5'-NRG-3', where R comprises either A or G, where N is any nucleotide and N is immediately 3' of the target nucleic acid sequence targeted by the spacer sequence.

The target nucleic acid sequence can comprise 20 nucleotides. The target nucleic acid can comprise less than 20 nucleotides. The target nucleic acid can comprise more than 20 nucleotides. The target nucleic acid can comprise at least: 5, 10, 15, 16, 17, 18, 19, 20, 21, 22, 23, 24, 25, 30 or more nucleotides. The target nucleic acid can comprise at most: 5, 10, 15, 16, 17, 18, 19, 20, 21, 22, 23, 24, 25, 30 or more nucleotides. The target nucleic acid sequence can comprise 20 bases immediately 5' of the first nucleotide of the PAM. For example, in a sequence comprising 5'-NNNNNNNNNNNNNNNNNNNNNRG-3' (SEQ ID NO: 125500), the target nucleic acid can comprise the sequence that corresponds to the Ns, wherein N is any nucleotide, and the underlined NRG sequence is the *S. pyogenes* PAM. This target nucleic acid sequence is often referred to as the PAM strand, and the complementary nucleic acid sequence is often referred to the non-PAM strand. One of skill in the art would recognize that the spacer sequence hybridizes to the non-PAM strand of the target nucleic acid (FIGS. 1A and 1B).

The spacer sequence that hybridizes to the target nucleic acid can have a length of at least about 6 nucleotides (nt). The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some examples, the spacer sequence can comprise 20 nucleotides. In some examples, the spacer can comprise 19 nucleotides. In some examples, the spacer can comprise 18 nucleotides. In some examples, the spacer can comprise 22 nucleotides.

In some examples, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the spacer sequence and the target nucleic acid is 100% over the six contiguous 5'-most nucleotides of the target sequence of the complementary strand of the target nucleic acid. The percent complementarity between the spacer sequence and the target nucleic acid can be at least 60% over about 20 contiguous nucleotides. The length of the spacer sequence and the target nucleic acid can differ by 1 to 6 nucleotides, which may be thought of as a bulge or bulges.

The spacer sequence can be designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like.

Minimum CRISPR Repeat Sequence

In some aspects, a minimum CRISPR repeat sequence is a sequence with at least about 30%, about 40%, about 50%, about 60%, about 65%, about 70%, about 75%, about 80%, about 85%, about 90%, about 95%, or 100% sequence identity to a reference CRISPR repeat sequence (e.g., crRNA from *S. pyogenes*).

In some aspects, a minimum CRISPR repeat sequence comprises nucleotides that can hybridize to a minimum tracrRNA sequence in a cell. The minimum CRISPR repeat sequence and a minimum tracrRNA sequence can form a duplex, i.e. a base-paired double-stranded structure. Together, the minimum CRISPR repeat sequence and the minimum tracrRNA sequence can bind to the site-directed polypeptide. At least a part of the minimum CRISPR repeat sequence can hybridize to the minimum tracrRNA sequence. At least a part of the minimum CRISPR repeat sequence can comprise at least about 30%, about 40%, about 50%, about 60%, about 65%, about 70%, about 75%, about 80%, about 85%, about 90%, about 95%, or 100% complementary to the minimum tracrRNA sequence. In some aspects, at least a part of the minimum CRISPR repeat sequence comprises at most about 30%, about 40%, about 50%, about 60%, about 65%, about 70%, about 75%, about 80%, about 85%, about 90%, about 95%, or 100% complementary to the minimum tracrRNA sequence.

The minimum CRISPR repeat sequence can have a length from about 7 nucleotides to about 100 nucleotides. For example, the length of the minimum CRISPR repeat sequence is from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. In some aspects, the minimum CRISPR repeat sequence is approximately 9 nucleotides in length. In some aspects, the minimum CRISPR repeat sequence is approximately 12 nucleotides in length.

The minimum CRISPR repeat sequence can be at least about 60% identical to a reference minimum CRISPR repeat sequence (e.g., wild-type crRNA from *S. pyogenes*) over a stretch of at least 6, 7, or 8 contiguous nucleotides. For example, the minimum CRISPR repeat sequence can be at least about 65% identical, at least about 70% identical, at least about 75% identical, at least about 80% identical, at least about 85% identical, at least about 90% identical, at least about 95% identical, at least about 98% identical, at least about 99% identical or 100% identical to a reference minimum CRISPR repeat sequence over a stretch of at least 6, 7, or 8 contiguous nucleotides.

Minimum tracrRNA Sequence

A minimum tracrRNA sequence can be a sequence with at least about 30%, about 40%, about 50%, about 60%, about 65%, about 70%, about 75%, about 80%, about 85%, about 90%, about 95%, or 100% sequence identity to a reference tracrRNA sequence (e.g., wild type tracrRNA from *S. pyogenes*).

A minimum tracrRNA sequence can comprise nucleotides that hybridize to a minimum CRISPR repeat sequence in a cell. A minimum tracrRNA sequence and a minimum CRISPR repeat sequence form a duplex, i.e. a base-paired double-stranded structure. Together, the minimum tracrRNA sequence and the minimum CRISPR repeat can bind to a site-directed polypeptide. At least a part of the minimum tracrRNA sequence can hybridize to the minimum CRISPR repeat sequence. The minimum tracrRNA sequence can be at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. The minimum tracrRNA sequence can be approximately 9 nucleotides in length. The minimum tracrRNA sequence can be approximately 12 nucleotides. The minimum tracrRNA can consist of tracrRNA nt 23-48 described in Jinek et al., supra.

The minimum tracrRNA sequence can be at least about 60% identical to a reference minimum tracrRNA (e.g., wild type, tracrRNA from *S. pyogenes*) sequence over a stretch of at least 6, 7, or 8 contiguous nucleotides. For example, the minimum tracrRNA sequence can be at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

The duplex between the minimum CRISPR RNA and the minimum tracrRNA can comprise a double helix. The duplex between the minimum CRISPR RNA and the minimum tracrRNA can comprise at least about 1, 2, 3, 4, 5, 6, 7, 8, 9, or 10 or more nucleotides. The duplex between the minimum CRISPR RNA and the minimum tracrRNA can comprise at most about 1, 2, 3, 4, 5, 6, 7, 8, 9, or 10 or more nucleotides.

The duplex can comprise a mismatch (i.e., the two strands of the duplex are not 100% complementary). The duplex can comprise at least about 1, 2, 3, 4, or 5 or mismatches. The duplex can comprise at most about 1, 2, 3, 4, or 5 or mismatches. The duplex can comprise no more than 2 mismatches.

Bulges

In some cases, there can be a "bulge" in the duplex between the minimum CRISPR RNA and the minimum tracrRNA. A bulge is an unpaired region of nucleotides within the duplex. A bulge can contribute to the binding of the duplex to the site-directed polypeptide. The bulge can comprise, on one side of the duplex, an unpaired 5'-XXXY-3' where X is any purine and Y comprises a nucleotide that can form a wobble pair with a nucleotide on the opposite strand, and an unpaired nucleotide region on the other side of the duplex. The number of unpaired nucleotides on the two sides of the duplex can be different.

In one example, the bulge can comprise an unpaired purine (e.g., adenine) on the minimum CRISPR repeat strand of the bulge. In some examples, the bulge can comprise an unpaired 5'-AAGY-3' of the minimum tracrRNA sequence strand of the bulge, where Y comprises a nucleotide that can form a wobble pairing with a nucleotide on the minimum CRISPR repeat strand.

A bulge on the minimum CRISPR repeat side of the duplex can comprise at least 1, 2, 3, 4, or 5 or more unpaired nucleotides. A bulge on the minimum CRISPR repeat side of the duplex can comprise at most 1, 2, 3, 4, or 5 or more unpaired nucleotides. A bulge on the minimum CRISPR repeat side of the duplex can comprise 1 unpaired nucleotide.

A bulge on the minimum tracrRNA sequence side of the duplex can comprise at least 1, 2, 3, 4, 5, 6, 7, 8, 9, or 10 or more unpaired nucleotides. A bulge on the minimum tracrRNA sequence side of the duplex can comprise at most 1, 2, 3, 4, 5, 6, 7, 8, 9, or 10 or more unpaired nucleotides. A bulge on a second side of the duplex (e.g., the minimum tracrRNA sequence side of the duplex) can comprise 4 unpaired nucleotides.

A bulge can comprise at least one wobble pairing. In some examples, a bulge can comprise at most one wobble pairing. A bulge can comprise at least one purine nucleotide. A bulge can comprise at least 3 purine nucleotides. A bulge sequence can comprise at least 5 purine nucleotides. A bulge sequence can comprise at least one guanine nucleotide. In some examples, a bulge sequence can comprise at least one adenine nucleotide.

Hairpins

In various examples, one or more hairpins can be located 3' to the minimum tracrRNA in the 3' tracrRNA sequence.

The hairpin can start at least about 1, 2, 3, 4, 5, 6, 7, 8, 9, 10, 15, or 20 or more nucleotides 3' from the last paired nucleotide in the minimum CRISPR repeat and minimum tracrRNA sequence duplex. The hairpin can start at most about 1, 2, 3, 4, 5, 6, 7, 8, 9 or 10 or more nucleotides 3' of the last paired nucleotide in the minimum CRISPR repeat and minimum tracrRNA sequence duplex.

The hairpin can comprise at least about 1, 2, 3, 4, 5, 6, 7, 8, 9, 10, 15, or 20 or more consecutive nucleotides. The hairpin can comprise at most about 1, 2, 3, 4, 5, 6, 7, 8, 9, 10, 15, or more consecutive nucleotides.

The hairpin can comprise a CC dinucleotide (i.e., two consecutive cytosine nucleotides).

The hairpin can comprise duplexed nucleotides (e.g., nucleotides in a hairpin, hybridized together). For example, a hairpin can comprise a CC dinucleotide that is hybridized to a GG dinucleotide in a hairpin duplex of the 3' tracrRNA sequence.

One or more of the hairpins can interact with guide RNA-interacting regions of a site-directed polypeptide.

In some examples, there are two or more hairpins, and in other examples there are three or more hairpins.

3' tracrRNA Sequence

A 3' tracrRNA sequence can comprise a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from S. pyogenes).

The 3' tracrRNA sequence can have a length from about 6 nucleotides to about 100 nucleotides. For example, the 3' tracrRNA sequence can have a length from about 6 nucleotides (nt) to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. The 3' tracrRNA sequence can have a length of approximately 14 nucleotides.

The 3' tracrRNA sequence can be at least about 60% identical to a reference 3' tracrRNA sequence (e.g., wild type 3' tracrRNA sequence from S. pyogenes) over a stretch of at least 6, 7, or 8 contiguous nucleotides. For example, the 3' tracrRNA sequence can be at least about 60% identical, about 65% identical, about 70% identical, about 75% identical, about 80% identical, about 85% identical, about 90% identical, about 95% identical, about 98% identical, about 99% identical, or 100% identical, to a reference 3' tracrRNA sequence (e.g., wild type 3' tracrRNA sequence from S. pyogenes) over a stretch of at least 6, 7, or 8 contiguous nucleotides.

The 3' tracrRNA sequence can comprise more than one duplexed region (e.g., hairpin, hybridized region). The 3' tracrRNA sequence can comprise two duplexed regions.

The 3' tracrRNA sequence can comprise a stem loop structure. The stem loop structure in the 3' tracrRNA can comprise at least 1, 2, 3, 4, 5, 6, 7, 8, 9, 10, 15 or 20 or more nucleotides. The stem loop structure in the 3' tracrRNA can comprise at most 1, 2, 3, 4, 5, 6, 7, 8, 9 or 10 or more nucleotides. The stem loop structure can comprise a functional moiety. For example, the stem loop structure can comprise an aptamer, a ribozyme, a protein-interacting hairpin, a CRISPR array, an intron, or an exon. The stem loop structure can comprise at least about 1, 2, 3, 4, or 5 or more functional moieties. The stem loop structure can comprise at most about 1, 2, 3, 4, or 5 or more functional moieties.

The hairpin in the 3' tracrRNA sequence can comprise a P-domain. In some examples, the P-domain can comprise a double-stranded region in the hairpin.

tracrRNA Extension Sequence

A tracrRNA extension sequence may be provided whether the tracrRNA is in the context of single-molecule guides or double-molecule guides. The tracrRNA extension sequence can have a length from about 1 nucleotide to about 400 nucleotides. The tracrRNA extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, or 400 nucleotides. The tracrRNA extension sequence can have a length from about 20 to about 5000 or more nucleotides. The tracrRNA extension sequence can have a length of more than 1000 nucleotides. The tracrRNA extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 or more nucleotides. The tracrRNA extension sequence can have a length of less than 1000 nucleotides. The tracrRNA extension sequence can comprise less than 10 nucleotides in length. The tracrRNA extension sequence can be 10-30 nucleotides in length. The tracrRNA extension sequence can be 30-70 nucleotides in length.

The tracrRNA extension sequence can comprise a functional moiety (e.g., a stability control sequence, ribozyme, endoribonuclease binding sequence). The functional moiety can comprise a transcriptional terminator segment (i.e., a transcription termination sequence). The functional moiety can have a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt. The functional moiety can function in a eukaryotic cell. The functional moiety can function in a prokaryotic cell. The functional moiety can function in both eukaryotic and prokaryotic cells.

Non-limiting examples of suitable tracrRNA extension functional moieties include a 3' poly-adenylated tail, a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like). The tracrRNA extension sequence can comprise a primer binding site or a molecular index (e.g., barcode sequence). The tracrRNA extension sequence can comprise one or more affinity tags.

Single-Molecule Guide Linker Sequence

The linker sequence of a single-molecule guide nucleic acid can have a length from about 3 nucleotides to about 100 nucleotides. In Jinek et al., supra, for example, a simple 4 nucleotide "tetraloop" (-GAAA-) was used, Science, 337 (6096):816-821 (2012). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. The linker of a single-molecule guide nucleic acid can be between 4 and 40 nucleotides. The linker can be at least about 100, 500, 1000, 1500, 2000, 2500, 3000, 3500, 4000, 4500, 5000, 5500, 6000, 6500, or 7000 or more nucleotides. The linker can be at most about 100, 500, 1000, 1500, 2000, 2500, 3000, 3500, 4000, 4500, 5000, 5500, 6000, 6500, or 7000 or more nucleotides.

Linkers can comprise any of a variety of sequences, although in some examples the linker will not comprise sequences that have extensive regions of homology with other portions of the guide RNA, which might cause intramolecular binding that could interfere with other functional regions of the guide. In Jinek et al., supra, a simple 4 nucleotide sequence -GAAA- was used, Science, 337 (6096):816-821 (2012), but numerous other sequences, including longer sequences can likewise be used.

The linker sequence can comprise a functional moiety. For example, the linker sequence can comprise one or more features, including an aptamer, a ribozyme, a protein-interacting hairpin, a protein binding site, a CRISPR array, an intron, or an exon. The linker sequence can comprise at least about 1, 2, 3, 4, or 5 or more functional moieties. In some examples, the linker sequence can comprise at most about 1, 2, 3, 4, or 5 or more functional moieties.

Nucleic Acid Modifications (Chemical and Structural Modifications)

In some aspects, polynucleotides introduced into cells can comprise one or more modifications that can be used individually or in combination, for example, to enhance activity, stability or specificity, alter delivery, reduce innate immune responses in host cells, or for other enhancements, as further described herein and known in the art.

In certain examples, modified polynucleotides can be used in the CRISPR/Cas9 or CRISPR/Cpf1 system, in which case the guide RNAs (either single-molecule guides or double-molecule guides) and/or a DNA or an RNA encoding a Cas9 or Cpf1 endonuclease introduced into a cell can be modified, as described and illustrated below. Such modified polynucleotides can be used in the CRISPR/Cas9 or CRISPR/Cpf1 system to edit any one or more genomic loci.

Using the CRISPR/Cas9 or CRISPR/Cpf1 system for purposes of non-limiting illustrations of such uses, modifications of guide RNAs can be used to enhance the formation or stability of the CRISPR/Cas9 or CRISPR/Cpf1 genome editing complex comprising guide RNAs, which can be single-molecule guides or double-molecule, and a Cas9 or Cpf1 endonuclease. Modifications of guide RNAs can also or alternatively be used to enhance the initiation, stability or kinetics of interactions between the genome editing complex with the target sequence in the genome, which can be used, for example, to enhance on-target activity. Modifications of guide RNAs can also or alternatively be used to enhance specificity, e.g., the relative rates of genome editing at the on-target site as compared to effects at other (off-target) sites.

Modifications can also or alternatively be used to increase the stability of a guide RNA, e.g., by increasing its resistance to degradation by ribonucleases (RNases) present in a cell, thereby causing its half-life in the cell to be increased. Modifications enhancing guide RNA half-life can be particularly useful in aspects in which a Cas9 or Cpf1 endonuclease is introduced into the cell to be edited via an RNA that needs to be translated in order to generate endonuclease, because increasing the half-life of guide RNAs introduced at the same time as the RNA encoding the endonuclease can be used to increase the time that the guide RNAs and the encoded Cas9 or Cpf1 endonuclease co-exist in the cell.

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease that are introduced into a cell, including, without limitation, modifications that enhance the stability of the RNA (such as by increasing its degradation by RNases present in the cell), modifications that enhance translation of the resulting product (i.e. the endonuclease), and/or modifications that decrease the likelihood or degree to which the RNAs introduced into cells elicit innate immune responses.

Combinations of modifications, such as the foregoing and others, can likewise be used. In the case of CRISPR/Cas9 or CRISPR/Cpf1, for example, one or more types of modifications can be made to guide RNAs (including those exemplified above), and/or one or more types of modifications can be made to RNAs encoding Cas endonuclease (including those exemplified above).

By way of illustration, guide RNAs used in the CRISPR/Cas9 or CRISPR/Cpf1 system, or other smaller RNAs can be readily synthesized by chemical means, enabling a number of modifications to be readily incorporated, as illustrated below and described in the art. While chemical synthetic procedures are continually expanding, purifications of such RNAs by procedures such as high-performance liquid chromatography (HPLC, which avoids the use of gels such as PAGE) tends to become more challenging as polynucleotide lengths increase significantly beyond a hundred or so nucleotides. One approach that can be used for generating chemically-modified RNAs of greater length is to produce two or more molecules that are ligated together. Much longer RNAs, such as those encoding a Cas9 endonuclease, are more readily generated enzymatically. While fewer types of modifications are available for use in enzymatically produced RNAs, there are still modifications that can be used to, e.g., enhance stability, reduce the likelihood or degree of innate immune response, and/or enhance other attributes, as described further below and in the art; and new types of modifications are regularly being developed.

By way of illustration of various types of modifications, especially those used frequently with smaller chemically synthesized RNAs, modifications can comprise one or more nucleotides modified at the 2' position of the sugar, in some aspects a 2'-O-alkyl, 2'-O-alkyl-O-alkyl, or 2'-fluoro-modified nucleotide. In some examples, RNA modifications include 2'-fluoro, 2'-amino or 2'-O-methyl modifications on the ribose of pyrimidines, abasic residues, or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligonucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—$CH_2$); amide backbones [see De Mesmaeker et al., Ace. Chem. Res., 28:366-374 (1995)]; morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Braasch and David Corey, Biochemistry, 41(14): 4503-4510 (2002); Genesis, Volume 30, Issue 3, (2001); Heasman, Dev. Biol., 243: 209-214 (2002); Nasevicius et al., Nat. Genet., 26:216-220 (2000); Lacerra et al., Proc. Natl. Acad. Sci., 97: 9591-9596 (2000); and U.S. Pat. No. 5,034,506, issued Jul. 23, 1991.

Cyclohexenyl nucleic acid oligonucleotide mimetics are described in Wang et al., J. Am. Chem. Soc., 122: 8595-8602 (2000).

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

One or more substituted sugar moieties can also be included, e.g., one of the following at the 2' position: OH, SH, $SCH_3$, F, OCN, $OCH_3OCH_3$, $OCH_3O(CH_2)nCH_3$, $O(CH_2)nNH_2$, or $O(CH_2)nCH_3$, where n is from 1 to about 10; C1 to C10 lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some aspects, a modification includes 2'-methoxyethoxy (2'-O—$CH_2CH_2OCH_3$, also known as 2'-O-(2-methoxyethyl)) (Martin et al, Helv. Chim. Acta, 1995, 78, 486). Other modifications include 2'-methoxy (2'-O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics, such as cyclobutyls in place of the pentofuranosyl group.

In some examples, both a sugar and an internucleoside linkage, i.e., the backbone, of the nucleotide units can be replaced with novel groups. The base units can be maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide can be replaced with an amide containing backbone, for example, an aminoethylglycine backbone. The nucleobases can be retained and bound directly or indirectly to aza nitrogen atoms of the amide portion of the backbone. Representative U.S. patents that teach the preparation of PNA compounds comprise, but are not limited to, U.S. Pat. Nos. 5,539,082; 5,714,331; and 5,719,262. Further teaching of PNA compounds can be found in Nielsen et al, Science, 254: 1497-1500 (1991).

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino) adenine, 2-(imidazolylalkyl)adenine, 2-(aminoalklyamino) adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl) adenine, and 2,6-diaminopurine. Kornberg, A., DNA Replication, W. H. Freeman & Co., San Francisco, pp. 75-77 (1980); Gebeyehu et al., Nucl. Acids Res. 15:4513 (1997). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Further, nucleobases can comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the present disclosure. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are aspects of base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,681,941; 5,750,692; 5,763,588; 5,830,653; 6,005,096; and U.S. Patent Application Publication 2003/0158403.

Thus, the term "modified" refers to a non-natural sugar, phosphate, or base that is incorporated into a guide RNA, an endonuclease, or both a guide RNA and an endonuclease. It is not necessary for all positions in a given oligonucleotide to be uniformly modified, and in fact more than one of the aforementioned modifications can be incorporated in a single oligonucleotide, or even in a single nucleoside within an oligonucleotide.

The guide RNAs and/or mRNA (or DNA) encoding an endonuclease can be chemically linked to one or more moieties or conjugates that enhance the activity, cellular distribution, or cellular uptake of the oligonucleotide. Such moieties comprise, but are not limited to, lipid moieties such as a cholesterol moiety [Letsinger et al., Proc. Natl. Acad. Sci. USA, 86: 6553-6556 (1989)]; cholic acid [Manoharan et al., Bioorg. Med. Chem. Let., 4: 1053-1060 (1994)]; a thioether, e.g., hexyl-S-tritylthiol [Manoharan et al, Ann. N. Y. Acad. Sci., 660: 306-309 (1992) and Manoharan et al., Bioorg. Med. Chem. Let., 3: 2765-2770 (1993)]; a thiocholesterol [Oberhauser et al., Nucl. Acids Res., 20: 533-538 (1992)]; an aliphatic chain, e.g., dodecandiol or undecyl residues [Kabanov et al., FEBS Lett., 259: 327-330 (1990) and Svinarchuk et al., Biochimie, 75: 49-54 (1993)]; a phospholipid, e.g., di-hexadecyl-rac-glycerol or triethylammonium 1,2-di-O-hexadecyl-rac-glycero-3-H-phosphonate [Manoharan et al., Tetrahedron Lett., 36: 3651-3654 (1995) and Shea et al., Nucl. Acids Res., 18: 3777-3783 (1990)]; a polyamine or a polyethylene glycol chain [Mancharan et al., Nucleosides & Nucleotides, 14: 969-973 (1995)]; adamantane acetic acid [Manoharan et al., Tetrahedron Lett., 36: 3651-3654 (1995)]; a palmityl moiety [(Mishra et al., Biochim. Biophys. Acta, 1264: 229-237 (1995)]; or an octadecylamine or hexylamino-carbonyl-t oxycholesterol moiety [Crooke et al., J. Pharmacol. Exp. Ther., 277: 923-937 (1996)]. See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Sugars and other moieties can be used to target proteins and complexes comprising nucleotides, such as cationic polysomes and liposomes, to particular sites. For example, hepatic cell directed transfer can be mediated via asialoglycoprotein receptors (ASGPRs); see, e.g., Hu, et al., Protein Pept Lett. 21(10):1025-30 (2014). Other systems known in the art and regularly developed can be used to target biomolecules of use in the present case and/or complexes thereof to particular target cells of interest.

These targeting moieties or conjugates can include conjugate groups covalently bound to functional groups, such as primary or secondary hydroxyl groups. Conjugate groups of the present disclosure include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this present disclosure, include groups that improve uptake, enhance resistance to degradation, and/or strengthen sequence-specific hybridization with the target nucleic acid. Groups that enhance the pharmacokinetic properties, in the context of this present disclosure, include groups that improve uptake, distribution, metabolism or excretion of the compounds of the present disclosure. Representative conjugate groups are disclosed in International Patent Application No. PCT/US92/09196, filed Oct. 23, 1992 (published as WO1993007883), and U.S. Pat. No. 6,287,860. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are typically produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding Cas9 is approximately 4 kb in length and can be synthesized by in vitro transcription. Modifications to the mRNA can be applied to, e.g., increase its translation or stability (such as by increasing its resistance to degradation with a cell), or to reduce the tendency of the RNA to elicit an innate immune response that is often observed in cells following introduction of exogenous RNAs, particularly longer RNAs such as that encoding Cas9.

Numerous such modifications have been described in the art, such as polyA tails, 5' cap analogs (e.g., Anti Reverse Cap Analog (ARCA) or m7G(5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates. These and other modifications are known in the art, and new modifications of RNAs are regularly being developed.

There are numerous commercial suppliers of modified RNAs, including for example, TriLink Biotech, AxoLabs, Bio-Synthesis Inc., Dharmacon and many others. As described by TriLink, for example, 5-Methyl-CTP can be used to impart desirable characteristics, such as increased nuclease stability, increased translation or reduced interaction of innate immune receptors with in vitro transcribed RNA. 5-Methylcytidine-5'-Triphosphate (5-Methyl-CTP), N6-Methyl-ATP, as well as Pseudo-UTP and 2-Thio-UTP, have also been shown to reduce innate immune stimulation in culture and in vivo while enhancing translation, as illustrated in publications by Kormann et al. and Warren et al. referred to below.

It has been shown that chemically modified mRNA delivered in vivo can be used to achieve improved therapeutic effects; see, e.g., Kormann et al., Nature Biotechnology 29, 154-157 (2011). Such modifications can be used, for example, to increase the stability of the RNA molecule and/or reduce its immunogenicity. Using chemical modifications such as Pseudo-U, N6-Methyl-A, 2-Thio-U and 5-Methyl-C, it was found that substituting just one quarter of the uridine and cytidine residues with 2-Thio-U and 5-Methyl-C respectively resulted in a significant decrease in toll-like receptor (TLR) mediated recognition of the mRNA in mice. By reducing the activation of the innate immune system, these modifications can be used to effectively increase the stability and longevity of the mRNA in vivo; see, e.g., Kormann et al., supra.

It has also been shown that repeated administration of synthetic messenger RNAs incorporating modifications designed to bypass innate anti-viral responses can reprogram differentiated human cells to pluripotency. See, e.g., Warren, et al., Cell Stem Cell, 7(5):618-30 (2010). Such modified mRNAs that act as primary reprogramming proteins can be an efficient means of reprogramming multiple human cell types. Such cells are referred to as induced pluripotency stem cells (iPSCs), and it was found that enzymatically synthesized RNA incorporating 5-Methyl-CTP, Pseudo-UTP and an Anti Reverse Cap Analog (ARCA) could be used to effectively evade the cell's antiviral response; see, e.g., Warren et al., supra.

Other modifications of polynucleotides described in the art include, for example, the use of polyA tails, the addition of 5' cap analogs (such as m7G(5')ppp(5')G (mCAP)), modifications of 5' or 3' untranslated regions (UTRs), or treatment with phosphatase to remove 5' terminal phosphates—and new approaches are regularly being developed.

A number of compositions and techniques applicable to the generation of modified RNAs for use herein have been developed in connection with the modification of RNA interference (RNAi), including small-interfering RNAs (siRNAs). siRNAs present particular challenges in vivo because their effects on gene silencing via mRNA interference are generally transient, which can require repeat administration. In addition, siRNAs are double-stranded RNAs (dsRNA) and mammalian cells have immune responses that have evolved to detect and neutralize dsRNA, which is often a by-product of viral infection. Thus, there are mammalian enzymes such as PKR (dsRNA-responsive kinase), and potentially retinoic acid-inducible gene I (RIG-I), that can mediate cellular responses to dsRNA, as well as Toll-like receptors (such as TLR3, TLR7 and TLR8) that can trigger the induction of cytokines in response to such molecules; see, e.g., the reviews by Angart et al., Pharmaceuticals (Basel) 6(4): 440-468 (2013); Kanasty et al., Molecular Therapy 20(3): 513-524 (2012); Burnett et al., Biotechnol J. 6(9):1130-46 (2011); Judge and MacLachlan, Hum Gene Ther 19(2):111-24 (2008); and references cited therein.

A large variety of modifications have been developed and applied to enhance RNA stability, reduce innate immune responses, and/or achieve other benefits that can be useful in connection with the introduction of polynucleotides into human cells, as described herein; see, e.g., the reviews by Whitehead K A et al., Annual Review of Chemical and Biomolecular Engineering, 2: 77-96 (2011); Gaglione and Messere, Mini Rev Med Chem, 10(7):578-95 (2010); Chernolovskaya et al, Curr Opin Mol Ther., 12(2):158-67 (2010); Deleavey et al., Curr Protoc Nucleic Acid Chem Chapter 16: Unit 16.3 (2009); Behlke, Oligonucleotides 18(4):305-19 (2008); Fucini et al., Nucleic Acid Ther 22(3): 205-210 (2012); Bremsen et al., Front Genet 3:154 (2012).

As noted above, there are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kole, Nature Reviews Drug Discovery 11:125-140 (2012). Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O-Methyl, 2'-Fluoro, 2'-Hydro) have been associated with highly stable siRNAs for applications in vivo, as reported by Soutschek et al. Nature 432:173-178 (2004); and 2'-O-Methyl modifications have been reported to be effective in improving stability as reported by Volkov, Oligonucleotides 19:191-202 (2009). With respect to decreasing the induction of innate immune responses, modifying specific sequences with 2'-O-Methyl, 2'-Fluoro, 2'-Hydro have been reported to reduce TLR7/TLR8 interaction while generally preserving silencing activity; see, e.g., Judge et al., Mol. Ther. 13:494-505 (2006); and Cekaite et al., J. Mol. Biol. 365:90-108 (2007). Additional modifications, such as 2-thiouracil, pseudouracil, 5-methylcytosine, 5-methyluracil, and N6-methyladenosine have also been shown to minimize the immune effects mediated by TLR3, TLR7, and TLR8; see, e.g., Kariko, K. et al., Immunity 23:165-175 (2005).

As is also known in the art, and commercially available, a number of conjugates can be applied to polynucleotides, such as RNAs, for use herein that can enhance their delivery and/or uptake by cells, including for example, cholesterol, tocopherol and folic acid, lipids, peptides, polymers, linkers and aptamers; see, e.g., the review by Winkler, Ther. Deliv. 4:791-809 (2013), and references cited therein.

Codon-Optimization

A polynucleotide encoding a site-directed polypeptide can be codon-optimized according to methods standard in the art for expression in the cell containing the target DNA of interest. For example, if the intended target nucleic acid is in a human cell, a human codon-optimized polynucleotide encoding Cas9 is contemplated for use for producing the Cas9 polypeptide.

Complexes of a Genome-Targeting Nucleic Acid and a Site-Directed Polypeptide

A genome-targeting nucleic acid interacts with a site-directed polypeptide (e.g., a nucleic acid-guided nuclease such as Cas9), thereby forming a complex. The genome-targeting nucleic acid guides the site-directed polypeptide to a target nucleic acid.

Ribonucleoprotein Complexes (RNPs)

The site-directed polypeptide and genome-targeting nucleic acid can each be administered separately to a cell or a patient. On the other hand, the site-directed polypeptide can be pre-complexed with one or more guide RNAs, or one or more crRNA together with a tracrRNA. The pre-complexed material can then be administered to a cell or a patient. Such pre-complexed material is known as a ribonucleoprotein particle (RNP). The site-directed polypeptide in the RNP can be, for example, a Cas9 endonuclease or a Cpf1 endonuclease. The site-directed polypeptide can be flanked at the N-terminus, the C-terminus, or both the N-terminus and C-terminus by one or more nuclear localization signals (NLSs). For example, a Cas9 endonuclease can be flanked by two NLSs, one NLS located at the N-terminus and the second NLS located at the C-terminus. The NLS can be any NLS known in the art, such as a SV40 NLS. The weight ratio of genome-targeting nucleic acid to site-directed polypeptide in the RNP can be 1:1. For example, the weight ratio of sgRNA to Cas9 endonuclease in the RNP can be 1:1.

Nucleic Acids Encoding System Components

The present disclosure provides a nucleic acid comprising a nucleotide sequence encoding a genome-targeting nucleic acid of the disclosure, a site-directed polypeptide of the disclosure, and/or any nucleic acid or proteinaceous molecule necessary to carry out the aspects of the methods of the disclosure.

The nucleic acid encoding a genome-targeting nucleic acid of the disclosure, a site-directed polypeptide of the disclosure, and/or any nucleic acid or proteinaceous molecule necessary to carry out the aspects of the methods of the disclosure can comprise a vector (e.g., a recombinant expression vector).

The term "vector" refers to a nucleic acid molecule capable of transporting another nucleic acid to which it has been linked. One type of vector is a "plasmid", which refers to a circular double-stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some examples, vectors can be capable of directing the expression of nucleic acids to which they are operatively linked. Such vectors are referred to herein as "recombinant expression vectors", or more simply "expression vectors", which serve equivalent functions.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, Calif. (1990). Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Other vectors can be used so long as they are compatible with the host cell.

In some examples, a vector can comprise one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. The vector can be a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

For expressing small RNAs, including guide RNAs used in connection with Cas endonuclease, various promoters such as RNA polymerase III promoters, including for example U6 and H1, can be advantageous. Descriptions of and parameters for enhancing the use of such promoters are known in art, and additional information and approaches are regularly being described; see, e.g., Ma, H. et al., *Molecular Therapy—Nucleic Acids* 3, e161 (2014) doi:10.1038/mtna.2014.12.

The expression vector can also contain a ribosome binding site for translation initiation and a transcription terminator. The expression vector can also comprise appropriate sequences for amplifying expression. The expression vector can also include nucleotide sequences encoding non-native tags (e.g., histidine tag, hemagglutinin tag, green fluorescent protein, etc.) that are fused to the site-directed polypeptide, thus resulting in a fusion protein.

A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter). In some cases, the promoter can be a spatially restricted and/or temporally restricted promoter (e.g., a tissue specific promoter, a cell type specific promoter, etc.).

The nucleic acid encoding a genome-targeting nucleic acid of the disclosure and/or a site-directed polypeptide can be packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Therapeutic Approach

Provided herein are methods for treating a patient with pain. An aspect of such method is an ex vivo cell-based therapy. For example, a biopsy of the patient's peripheral nerves is performed. The nerve tissue can be isolated from the patient's skin or leg. Then, a cell of the peripheral nervous system (e.g., a neuron or a glial cell such as Schwann cell in nerves or satellite glial cell in ganglia) is isolated from the biopsied material. Then, the chromosomal DNA of the cell of the peripheral nervous system (e.g., a neuron, or a glial cell such as Schwann cell in nerves or satellite glial cell in ganglia) can be edited using the materials and methods described herein. Finally, the edited cell of the peripheral nervous system (e.g., a neuron or a glial cell such as Schwann cell in nerves or satellite glial cell in ganglia) is implanted into the patient. Any source or type of cell may be used as the progenitor cell.

Another aspect of such method is an ex vivo cell-based therapy. For example, a patient specific induced pluripotent stem cell (iPSC) can be created. Then, the chromosomal DNA of these iPSC cells can be edited using the materials and methods described herein. Next, the genome-edited iPSCs can be differentiated into cells of the peripheral nervous system (e.g., a neuron or a glial cell such as Schwann cell in nerves or satellite glial cell in ganglia). Finally, the differentiated cells of the peripheral nervous system (e.g., a neuron or a glial cell such as Schwann cell in nerves or satellite glial cell in ganglia) are implanted into the patient.

Yet another aspect of such method is an ex vivo cell-based therapy. For example, a mesenchymal stem cell can be isolated from the patient, which can be isolated from the patient's bone marrow or peripheral blood. Next, the chromosomal DNA of these mesenchymal stem cells can be edited using the materials and methods described herein. Next, the genome-edited mesenchymal stem cells can be differentiated into cells of the peripheral nervous system (e.g., a neuron or a glial cell such as Schwann cell in nerves or satellite glial cell in ganglia). Finally, the differentiated cells of the peripheral nervous system (e.g., a neuron or a glial cell such as Schwann cell in nerves or satellite glial cell in ganglia) are implanted into the patient.

One advantage of an ex vivo cell therapy approach is the ability to conduct a comprehensive analysis of the therapeutic prior to administration. Nuclease-based therapeutics can have some level of off-target effects. Performing gene editing ex vivo allows one to characterize the edited cell population prior to implantation. The present disclosure includes sequencing the entire genome of the edited cells to ensure that the off-target effects, if any, can be in genomic locations associated with minimal risk to the patient. Furthermore, populations of specific cells, including clonal populations, can be isolated prior to implantation.

Another advantage of ex vivo cell therapy relates to genetic modification in iPSCs compared to other primary cell sources. iPSCs are prolific, making it easy to obtain the large number of cells that will be required for a cell-based therapy. Furthermore, iPSCs are an ideal cell type for performing clonal isolations. This allows screening for the correct genomic modification, without risking a decrease in viability. In contrast, other primary cells, such as glial cells, are viable for only a few passages and difficult to clonally expand. Thus, manipulation of iPSCs for the treatment of pain can be much easier, and can shorten the amount of time needed to make the desired genetic modification.

Methods can also include an in vivo based therapy. Chromosomal DNA of the cells in the patient is edited using the materials and methods described herein. In some aspects, the target cell in an in vivo based therapy is a neuron of the peripheral nervous system.

Although certain cells present an attractive target for ex vivo treatment and therapy, increased efficacy in delivery may permit direct in vivo delivery to such cells. Ideally the targeting and editing would be directed to the relevant cells. Cleavage in other cells can also be prevented by the use of promoters only active in certain cells and or developmental stages. Additional promoters are inducible, and therefore can be temporally controlled if the nuclease is delivered as a plasmid. The amount of time that delivered RNA and protein remain in the cell can also be adjusted using treatments or domains added to change the half-life. In vivo treatment would eliminate a number of treatment steps, but a lower rate of delivery can require higher rates of editing. In vivo treatment can eliminate problems and losses from ex vivo treatment and engraftment and post-engraftment integration of neurons and glial cells appropriately into existing brain circuits.

An advantage of in vivo gene therapy can be the ease of therapeutic production and administration. The same therapeutic approach and therapy will have the potential to be used to treat more than one patient, for example a number of patients who share the same or similar genotype or allele. In contrast, ex vivo cell therapy typically requires using a patient's own cells, which are isolated, manipulated and returned to the same patient.

Also provided herein is a cellular method for editing the SCN9A gene in a cell by genome editing. For example, a cell can be isolated from a patient or animal. Then, the chromosomal DNA of the cell can be edited using the materials and methods described herein.

The methods provided herein, regardless of whether a cellular or ex vivo or in vivo method, can involve reducing (knock-down) or eliminating (knock-out) the expression of the SCN9A gene by introducing one or more insertions, deletions or mutations within or near the SCN9A gene or other DNA sequences that encode regulatory elements of the SCN9A gene.

For example, the knock-down or knock-out strategy can involve disrupting the reading frame in the SCN9A gene by introducing random insertions or deletions (indels) that arise due to the imprecise NHEJ repair pathway. This can be achieved by inducing one single stranded break or double stranded break in the SCN9A gene with one or more CRISPR endonucleases and a gRNA (e.g., crRNA+tracrRNA, or sgRNA), or two or more single stranded breaks or double stranded breaks in the SCN9A gene with two or more CRISPR endonucleases and two or more sgRNAs. This approach can require development and optimization of sgRNAs for the SCN9A gene.

Alternatively, the knock-down or knock-out strategy can also involve deletion of one or more segments within or near the SCN9A gene or other DNA sequences that encode regulatory elements of the SCN9A gene. This deletion strategy requires at least a pair of gRNAs (e.g., crRNA+tracrRNA, or sgRNA) capable of binding to two different sites within or near the SCN9A gene and one or more CRISPR endonucleases. The CRISPR endonucleases, configured with the two gRNAs, induce two double stranded breaks at the desired locations. After cleavage, the two ends, regardless of whether blunt or with overhangs, can be joined by NHEJ, leading to the deletion of the intervening segment. In certain aspects, NHEJ repair pathways can lead to insertions, deletions or mutations at the joints.

In addition to the above genome editing strategies, another strategy involves modulating expression, function, or activity of SCN9A by editing in the regulatory sequence.

In addition to the editing options listed above, Cas9 or similar proteins can be used to target effector domains to the same target sites that can be identified for editing, or additional target sites within range of the effector domain. A range of chromatin modifying enzymes, methylases or demethylases can be used to alter expression of the target gene. One possibility is decreasing the expression of the SCN9A protein if a mutation leads to undesirable activity. These types of epigenetic regulation have some advantages, particularly as they are limited in possible off-target effects.

A number of types of genomic target sites can be present in addition to the coding and splicing sequences.

The regulation of transcription and translation implicates a number of different classes of sites that interact with cellular proteins or nucleotides. Often the DNA binding sites of transcription factors or other proteins can be targeted for mutation or deletion to study the role of the site, though they can also be targeted to change gene expression. Sites can be added through non-homologous end joining NHEJ or direct genome editing by homology directed repair (HDR). Increased use of genome sequencing, RNA expression and genome-wide studies of transcription factor binding have increased our ability to identify how the sites lead to developmental or temporal gene regulation. These control systems can be direct or can involve extensive cooperative regulation that can require the integration of activities from multiple enhancers. Transcription factors typically bind 6-12 bp-long degenerate DNA sequences. The low level of specificity provided by individual sites suggests that complex interactions and rules are involved in binding and the functional outcome. Binding sites with less degeneracy can provide simpler means of regulation. Artificial transcription factors can be designed to specify longer sequences that have less similar sequences in the genome and have lower potential for off-target cleavage. Any of these types of binding sites can be mutated, deleted or even created to enable changes in gene regulation or expression (Canver, M. C. et al., *Nature* (2015)).

Another class of gene regulatory regions having these features is microRNA (miRNA) binding sites. miRNAs are non-coding RNAs that play key roles in post-transcriptional gene regulation. miRNA can regulate the expression of 30% of all mammalian protein-encoding genes. Specific and potent gene silencing by double stranded RNA (RNAi) was discovered, plus additional small noncoding RNA (Canver, M. C. et al., *Nature* (2015)). The largest class of non-coding RNAs important for gene silencing is miRNAs. In mammals, miRNAs are first transcribed as a long RNA transcript, which can be separate transcriptional units, part of protein introns, or other transcripts. The long transcripts are called primary miRNA (pri-miRNA) that include imperfectly base-paired hairpin structures. These pri-miRNA can be cleaved into one or more shorter precursor miRNAs (pre-miRNAs) by Microprocessor, a protein complex in the nucleus, involving Drosha.

Pre-miRNAs are short stem loops ~70 nucleotides in length with a 2-nucleotide 3'-overhang that are exported, into the mature 19-25 nucleotide miRNA:miRNA* duplexes. The miRNA strand with lower base pairing stability (the guide strand) can be loaded onto the RNA-induced silencing complex (RISC). The passenger strand (marked with *), can be functional, but is usually degraded. The mature miRNA tethers RISC to partly complementary sequence motifs in target mRNAs predominantly found within the 3' untranslated regions (UTRs) and induces posttranscriptional gene silencing (Bartel, D. P. *Cell* 136, 215-233 (2009); Saj, A. & Lai, E. C. *Curr Opin Genet Dev* 21, 504-510 (2011)).

miRNAs can be important in development, differentiation, cell cycle and growth control, and in virtually all biological pathways in mammals and other multicellular organisms. miRNAs can also be involved in cell cycle control, apoptosis and stem cell differentiation, hematopoiesis, hypoxia, muscle development, neurogenesis, insulin secretion, cholesterol metabolism, aging, viral replication and immune responses.

A single miRNA can target hundreds of different mRNA transcripts, while an individual miRNA transcript can be targeted by many different miRNAs. More than 28645 microRNAs have been annotated in the latest release of miRBase (v.21). Some miRNAs can be encoded by multiple loci, some of which can be expressed from tandemly co-transcribed clusters. The features allow for complex regulatory networks with multiple pathways and feedback controls. miRNAs can be integral parts of these feedback and regulatory circuits and can help regulate gene expression by keeping protein production within limits (Herranz, H. & Cohen, S. M. *Genes Dev* 24, 1339-1344 (2010); Posadas, D. M. & Carthew, R. W. *Curr Opin Genet Dev* 27, 1-6 (2014)).

miRNA can also be important in a large number of human diseases that are associated with abnormal miRNA expression. This association underscores the importance of the miRNA regulatory pathway. Recent miRNA deletion studies have linked miRNA with regulation of the immune responses (Stern-Ginossar, N. et al., *Science* 317, 376-381 (2007)).

miRNA also has a strong link to cancer and can play a role in different types of cancer. miRNAs have been found to be downregulated in a number of tumors. miRNA can be important in the regulation of key cancer-related pathways, such as cell cycle control and the DNA damage response, and can therefore be used in diagnosis and can be targeted clinically. MicroRNAs can delicately regulate the balance of angiogenesis, such that experiments depleting all microRNAs suppress tumor angiogenesis (Chen, S. et al., *Genes Dev* 28, 1054-1067 (2014)).

As has been shown for protein coding genes, miRNA genes can also be subject to epigenetic changes occurring with cancer. Many miRNA loci can be associated with CpG islands increasing their opportunity for regulation by DNA methylation (Weber, B., Stresemann, C., Brueckner, B. & Lyko, F. *Cell Cycle* 6, 1001-1005 (2007)). The majority of studies have used treatment with chromatin remodeling drugs to reveal epigenetically silenced miRNAs.

In addition to their role in RNA silencing, miRNA can also activate translation (Posadas, D. M. & Carthew, R. W. *Curr Opin Genet Dev* 27, 1-6 (2014)). Knocking out miRNA sites may lead to decreased expression of the targeted gene, while introducing these sites may increase expression.

Individual miRNA can be knocked out most effectively by mutating the seed sequence (bases 2-8 of the microRNA), which can be important for binding specificity. Cleavage in this region, followed by mis-repair by NHEJ can effectively abolish miRNA function by blocking binding to target sites. miRNA could also be inhibited by specific targeting of the special loop region adjacent to the palindromic sequence. Catalytically inactive Cas9 can also be used to inhibit shRNA expression (Zhao, Y. et al., *Sci Rep* 4, 3943 (2014)). In addition to targeting the miRNA, the binding sites can also be targeted and mutated to prevent the silencing by miRNA.

According to the present disclosure, any of the microRNA (miRNA) or their binding sites may be incorporated into the compositions of the invention.

The compositions may have a region such as, but not limited to, a region comprising the sequence of any of the microRNAs listed in SEQ ID NOs: 632-4715, the reverse complement of the microRNAs listed in SEQ ID NOs: 632-4715 or the microRNA anti-seed region of any of the microRNAs listed in SEQ ID NOs: 632-4715.

The compositions of the present disclosure may comprise one or more microRNA target sequences, microRNA sequences, or microRNA seeds. Such sequences may correspond to any known microRNA such as those taught in U.S. Publication US2005/0261218 and U.S. Publication US2005/0059005. As a non-limiting example, known microRNAs, their sequences and their binding site sequences in the human genome are listed below in SEQ ID NOs: 632-4715.

A microRNA sequence comprises a "seed" sequence, i.e., a sequence in the region of positions 2-8 of the mature microRNA, which sequence has perfect Watson-Crick complementarity to the miRNA target sequence. A microRNA seed may comprise positions 2-8 or 2-7 of the mature microRNA. In some aspects, a microRNA seed may comprise 7 nucleotides (e.g., nucleotides 2-8 of the mature microRNA), wherein the seed-complementary site in the corresponding miRNA target is flanked by an adenine (A) opposed to microRNA position 1. In some aspects, a microRNA seed may comprise 6 nucleotides (e.g., nucleotides 2-7 of the mature microRNA), wherein the seed-complementary site in the corresponding miRNA target is flanked by an adenine (A) opposed to microRNA position 1. See for example, Grimson A, Farh K K, Johnston W K, Garrett-Engele P, Lim L P, Bartel D P; Mol Cell. 2007 Jul. 6; 27(1):91-105. The bases of the microRNA seed have complete complementarity with the target sequence.

Identification of microRNA, microRNA target regions, and their expression patterns and role in biology have been reported (Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136: 215-233; Landgraf et al, Cell, 2007 129:1401-1414; Gentner and Naldini, Tissue Antigens. 2012 80:393-403).

For example, if the composition is not intended to be delivered to the liver but ends up there, then miR-122, a microRNA abundant in liver, can inhibit the expression of the sequence delivered if one or multiple target sites of miR-122 are engineered into the polynucleotide encoding that target sequence. Introduction of one or multiple binding sites for different microRNA can be engineered to further decrease the longevity, stability, and protein translation hence providing an additional layer of tenability.

As used herein, the term "microRNA site" refers to a microRNA target site or a microRNA recognition site, or any nucleotide sequence to which a microRNA binds or associates. It should be understood that "binding" may follow traditional Watson-Crick hybridization rules or may reflect any stable association of the microRNA with the target sequence at or adjacent to the microRNA site.

Conversely, for the purposes of the compositions of the present disclosure, microRNA binding sites can be engineered out of (i.e. removed from) sequences in which they naturally occur in order to increase protein expression in specific tissues.

Specifically, microRNAs are known to be differentially expressed in immune cells (also called hematopoietic cells), such as antigen presenting cells (APCs) (e.g. dendritic cells and macrophages), macrophages, monocytes, B lymphocytes, T lymphocytes, granulocytes, natural killer cells, etc. Immune cell specific microRNAs are involved in immunogenicity, autoimmunity, the immune-response to infection, inflammation, as well as unwanted immune response after gene therapy and tissue/organ transplantation. Immune cells specific microRNAs also regulate many aspects of development, proliferation, differentiation and apoptosis of hematopoietic cells (immune cells). For example, miR-142 and miR-146 are exclusively expressed in the immune cells, particularly abundant in myeloid dendritic cells. Introducing the miR-142 binding site into the 3'-UTR of a polypeptide of the present disclosure can selectively suppress the gene expression in the antigen presenting cells through miR-142 mediated mRNA degradation, limiting antigen presentation in professional APCs (e.g. dendritic cells) and thereby preventing antigen-mediated immune response after gene delivery (see, Annoni A et al., blood, 2009, 114, 5152-5161).

In one example, microRNAs binding sites that are known to be expressed in immune cells, in particular, the antigen presenting cells, can be engineered into the polynucleotides to suppress the expression of the polynucleotide in APCs through microRNA mediated RNA degradation, subduing the antigen-mediated immune response, while the expression of the polynucleotide is maintained in non-immune cells where the immune cell specific microRNAs are not expressed.

Many microRNA expression studies have been conducted, and are described in the art, to profile the differential expression of microRNAs in various cancer cells/tissues and other diseases. Some microRNAs are abnormally overexpressed in certain cancer cells and others are underexpressed. For example, microRNAs are differentially expressed in cancer cells (WO2008/154098, US2013/0059015, US2013/0042333, WO2011/157294); cancer stem cells (US2012/0053224); pancreatic cancers and diseases (US2009/0131348, US2011/0171646, US2010/0286232, U.S. Pat. No. 8,389,210); asthma and inflammation (U.S. Pat. No. 8,415,096); prostate cancer (US2013/0053264); hepatocellular carcinoma (WO2012/151212, US2012/0329672, WO2008/054828, U.S. Pat. No. 8,252,538); lung cancer cells (WO2011/076143, WO2013/033640, WO2009/070653, US2010/0323357); cutaneous T-cell lymphoma (WO2013/011378); colorectal cancer cells (WO2011/0281756, WO2011/076142); cancer positive lymph nodes (WO2009/100430, US2009/0263803); nasopharyngeal carcinoma (EP2112235); chronic obstructive pulmonary disease (US2012/0264626, US2013/0053263); thyroid cancer (WO2013/066678); ovarian cancer cells (US2012/0309645, WO2011/095623); breast cancer cells (WO2008/154098, WO2007/081740, US2012/0214699), leukemia and lymphoma (WO2008/073915, US2009/0092974, US2012/0316081, US2012/0283310, WO2010/018563).

Non-limiting examples of microRNA sequences and the targeted tissues and/or cells are disclosed in SEQ ID NOs: 632-4715.

Genome Engineering Strategies

In some aspects, the methods of the present disclosure can involve editing one or both alleles. Gene editing to modify the allele(s) has the advantage of permanently altering the target gene or gene products.

A step of the ex vivo methods of the present disclosure can comprise editing the cells of the peripheral nervous system (e.g., a neuron or a glial cell such as Schwann cell in nerves or satellite glial cell in ganglia) isolated from the patient using genome engineering. Alternatively, a step of the ex vivo methods of the present disclosure can comprise editing the patient specific iPSC or mesenchymal stem cell. Likewise, a step of the in vivo methods of the present disclosure involves editing the cells in patients experiencing pain using genome engineering. Similarly, a step in the cellular methods of the present disclosure can comprise editing the SCN9A gene in a human cell by genome engineering.

Patients experiencing pain may exhibit a wide range of mutations in the SCN9A gene. Therefore, different patients may require different editing strategies. Any CRISPR endonuclease may be used in the methods of the present disclosure, each CRISPR endonuclease having its own associated PAM, which may or may not be disease specific.

For example, expression of the SCN9A gene may be disrupted or eliminated by introducing random insertions or deletions (indels) that arise due to the imprecise NHEJ repair pathway. The target regions may be the coding sequences of the SCN9A gene (i.e., exons). Inserting or deleting nucleotides into the coding sequence of a gene may cause a "frame shift" where the normal 3-letter codon pattern is disturbed. In this way, gene expression and therefore protein production can be reduced or eliminated. This approach may also be used to target any intron, intron:exon junction, or regulatory DNA element of the SCN9A gene where sequence alteration may interfere with the expression of the SCN9A gene.

As another example, NHEJ can also be used to delete segments of the gene, either directly or by altering splice donor or acceptor sites through cleavage by one gRNA targeting several locations, or several gRNAs. This can be useful if small random indels are inefficient to knock-out the target gene. Pairs of gRNAs have been used for this type of deletions.

Without a donor present, the ends from a DNA break or ends from different breaks can be joined using the several non-homologous repair pathways in which the DNA ends are joined with little or no base-pairing at the junction. In addition to canonical NHEJ, there are similar repair mechanisms, such as alt-NHEJ. If there are two breaks, the intervening segment can be deleted or inverted. NHEJ repair pathways can lead to insertions, deletions or mutations at the joints.

NHEJ can also lead to homology-independent target integration. For example, inclusion of a nuclease target site on a donor plasmid can promote integration of a transgene into the chromosomal double-strand break following in vivo nuclease cleavage of both the donor and the chromosome (Cristea., Biotechnol Bioeng. 2013 March; 110(3):871-80). NHEJ was used to insert a 15-kb inducible gene expression cassette into a defined locus in human cell lines after nuclease cleavage. (See e.g., Maresca, M., Lin, V. G., Guo, N. & Yang, Y., *Genome Res* 23, 539-546 (2013); Suzuki et al. *Nature,* 540, 144-149 (2016)). The integrated sequence may disrupt the reading frame of the SCN9A gene or alter the structure of the gene.

As a further alternative, homology directed repair (HDR) can also be used to knock-out a gene or alter the gene function. For example, the HDR knock-out strategy can involve disrupting the structure or function of the SCN9A gene by inserting into the SCN9A gene a non-functional or irrelevant sequence. This can be achieved by inducing one single stranded break or double stranded break in the gene of interest with one or more CRISPR endonucleases and a gRNA (e.g., crRNA+tracrRNA, or sgRNA), or two or more single stranded breaks or double stranded breaks in the gene of interest with one or more CRISPR endonucleases and two or more gRNAs, in the presence of a donor DNA template introduced exogenously to direct the cellular DSB response to Homology-Directed Repair (the donor DNA template can be a short single stranded oligonucleotide, a short double stranded oligonucleotide, a long single or double stranded DNA molecule). This approach can require development and optimization of gRNAs and donor DNA molecules for the SCN9A gene.

Homology directed repair (HDR) is essentially an error-free mechanism that uses a supplied homologous DNA sequence as a template during DSB repair. The rate of HDR is a function of the distance between the mutation and the cut site so choosing overlapping or nearest target sites is important. Templates can include extra sequences flanked by the homologous regions or can contain a sequence that differs from the genomic sequence, thus allowing sequence editing.

The most common form of HDR is homologous recombination. There are additional pathways for HDR, including single-strand annealing and alternative-HDR. Genome engineering tools allow researchers to manipulate the cellular homologous recombination pathways to create site-specific modifications to the genome. It has been found that cells can repair a double-stranded break using a synthetic donor molecule provided in trans. Therefore, by introducing a double-stranded break near a specific mutation and providing a suitable donor, targeted changes can be made in the genome. Specific cleavage increases the rate of HDR more than 1,000 fold above the rate of 1 in $10^6$ cells receiving a homologous donor alone. The rate of homology directed repair (HDR) at a particular nucleotide is a function of the distance to the cut site, so choosing overlapping or nearest target sites is important. Gene editing offers the advantage over gene addition, as editing in situ leaves the rest of the genome unperturbed.

Supplied donors for editing by HDR vary markedly but can contain the intended sequence with small or large flanking homology arms to allow annealing to the genomic DNA. The homology regions flanking the introduced genetic changes can be 30 bp or smaller, or as large as a multi-kilobase cassette that can contain promoters, cDNAs, etc. Both single-stranded and double-stranded oligonucleotide donors have been used. These oligonucleotides range in size from less than 100 nt to over many kb, though longer ssDNA can also be generated and used. Double-stranded donors can be used, including PCR amplicons, plasmids, and mini-circles. In general, it has been found that an AAV vector can be a very effective means of delivery of a donor template, though the packaging limits for individual donors is <5 kb. Active transcription of the donor increased HDR three-fold, indicating the inclusion of promoter may increase conversion. Conversely, CpG methylation of the donor decreased gene expression and HDR.

In addition to wild-type endonucleases, such as Cas9, nickase variants exist that have one or the other nuclease domain inactivated resulting in cutting of only one DNA strand. HDR can be directed from individual Cas nickases or using pairs of nickases that flank the target area. Donors can be single-stranded, nicked, or dsDNA.

The donor DNA can be supplied with the nuclease or independently by a variety of different methods, for example by transfection, nano-particle, micro-injection, or viral transduction. A range of tethering options has been proposed to increase the availability of the donors for HDR. Examples include attaching the donor to the nuclease, attaching to DNA binding proteins that bind nearby, or attaching to proteins that are involved in DNA end binding or repair.

The repair pathway choice can be guided by a number of culture conditions, such as those that influence cell cycling, or by targeting of DNA repair and associated proteins. For example, to increase HDR, key NHEJ molecules can be suppressed, such as KU70, KU80 or DNA ligase IV.

In addition to genome editing by NHEJ or HDR, site-specific gene insertions have been conducted that use both the NHEJ pathway and HDR. A combination approach may be applicable in certain settings, possibly including intron/exon borders. NHEJ may prove effective for ligation in the intron, while the error-free HDR may be better suited in the coding region.

The SCN9A gene contains a number of exons as shown in Table 3. Any one or more of these exons or nearby introns can be targeted in order to create one or more indels that disrupt the reading frame and eventually eliminate the abnormal SCN9A protein activity.

In some aspects, the methods can provide gRNA pairs that make a deletion by cutting the gene twice at locations flanking an unwanted sequence. This sequence may include one or more exons, introns, intron:exon junctions, other DNA sequences encoding regulatory elements of the SCN9A gene or combinations thereof. The cutting can be accomplished by a pair of DNA endonucleases that each makes a DSB in the genome, or by multiple nickases that together make a DSB in the genome.

Alternatively, the methods can provide one gRNA to make one double-strand cut within a coding or splicing sequence. The double-strand cut can be made by a single DNA endonuclease or multiple nickases that together make a DSB in the genome.

Splicing donor and acceptors are generally within 100 base pairs of the neighboring intron. In some examples, methods can provide gRNAs that cut approximately +/−100-3100 bp with respect to each exon/intron junction of interest.

For any of the genome editing strategies, gene editing can be confirmed by sequencing or PCR analysis.

Target Sequence Selection

Shifts in the location of the 5' boundary and/or the 3' boundary relative to particular reference loci can be used to facilitate or enhance particular applications of gene editing, which depend in part on the endonuclease system selected for the editing, as further described and illustrated herein.

In a first non-limiting example of such target sequence selection, many endonuclease systems have rules or criteria that can guide the initial selection of potential target sites for cleavage, such as the requirement of a PAM sequence motif in a particular position adjacent to the DNA cleavage sites in the case of CRISPR Type II or Type V endonucleases.

In another non-limiting example of target sequence selection or optimization, the frequency of off-target activity for a particular combination of target sequence and gene editing endonuclease (i.e. the frequency of DSBs occurring at sites other than the selected target sequence) can be assessed relative to the frequency of on-target activity. In some cases, cells that have been correctly edited at the desired locus can have a selective advantage relative to other cells. Illustrative, but non-limiting, examples of a selective advantage include the acquisition of attributes such as enhanced rates of replication, persistence, resistance to certain conditions, enhanced rates of successful engraftment or persistence in vivo following introduction into a patient, and other attributes associated with the maintenance or increased numbers or viability of such cells. In other cases, cells that have been correctly edited at the desired locus can be positively selected for by one or more screening methods used to identify, sort or otherwise select for cells that have been correctly edited. Both selective advantage and directed selection methods can take advantage of the phenotype associated with the alteration. In some cases, cells can be edited two or more times in order to create a second modification that creates a new phenotype that is used to select or purify the intended population of cells. Such a second modification could be created by adding a second gRNA enabling expression of a selectable or screenable marker. In some cases, cells can be correctly edited at the desired locus using a DNA fragment that contains the cDNA and also a selectable marker.

Whether any selective advantage is applicable or any directed selection is to be applied in a particular case, target sequence selection can also be guided by consideration of off-target frequencies in order to enhance the effectiveness of the application and/or reduce the potential for undesired alterations at sites other than the desired target. As described further and illustrated herein and in the art, the occurrence of off-target activity can be influenced by a number of factors including similarities and dissimilarities between the target site and various off-target sites, as well as the particular endonuclease used. Bioinformatics tools are available that assist in the prediction of off-target activity, and frequently such tools can also be used to identify the most likely sites of off-target activity, which can then be assessed in experimental settings to evaluate relative frequencies of off-target to on-target activity, thereby allowing the selection of sequences that have higher relative on-target activities. Illustrative examples of such techniques are provided herein, and others are known in the art.

Another aspect of target sequence selection relates to homologous recombination events. Sequences sharing regions of homology can serve as focal points for homologous recombination events that result in deletion of intervening sequences. Such recombination events occur during the normal course of replication of chromosomes and other DNA sequences, and also at other times when DNA sequences are being synthesized, such as in the case of repairs of double-strand breaks (DSBs), which occur on a regular basis during the normal cell replication cycle but can also be enhanced by the occurrence of various events (such as UV light and other inducers of DNA breakage) or the presence of certain agents (such as various chemical inducers). Many such inducers cause DSBs to occur indiscriminately in the genome, and DSBs can be regularly induced and repaired in normal cells. During repair, the original sequence can be reconstructed with complete fidelity, however, in some cases, small insertions or deletions (referred to as "indels") are introduced at the DSB site.

DSBs can also be specifically induced at particular locations, as in the case of the endonucleases systems described herein, which can be used to cause directed or preferential gene modification events at selected chromosomal locations. The tendency for homologous sequences to be subject to recombination in the context of DNA repair (as well as replication) can be taken advantage of in a number of circumstances, and is the basis for one application of gene editing systems, such as CRISPR, in which homology directed repair is used to insert a sequence of interest, provided through use of a "donor" polynucleotide, into a desired chromosomal location.

Regions of homology between particular sequences, which can be small regions of "microhomology" that can comprise as few as ten base pairs or less, can also be used to bring about desired deletions. For example, a single DSB can be introduced at a site that exhibits microhomology with a nearby sequence. During the normal course of repair of such DSB, a result that occurs with high frequency is the deletion of the intervening sequence as a result of recombination being facilitated by the DSB and concomitant cellular repair process.

In some circumstances, however, selecting target sequences within regions of homology can also give rise to much larger deletions, including gene fusions (when the deletions are in coding regions), which may or may not be desired given the particular circumstances.

The examples provided herein further illustrate the selection of various target regions for the creation of DSBs designed to induce insertions, deletions or mutations that result in reduction or elimination of SCN9A protein activity, as well as the selection of specific target sequences within such regions that are designed to minimize off-target events relative to on-target events.

Human Cells

For ameliorating pain or any disorder associated with SCN9A, as described and illustrated herein, the principal targets for gene editing are human cells. For example, in the ex vivo methods, the human cells can be somatic cells, which after being modified using the techniques as described, can give rise to differentiated cells, e.g., neurons of the peripheral nervous system or progenitor cells. For example, in the in vivo methods, the human cells may be neurons of the peripheral nervous system, or cells from other affected organs.

By performing gene editing in autologous cells that are derived from and therefore already completely matched with the patient in need, it is possible to generate cells that can be safely re-introduced into the patient, and effectively give rise to a population of cells that will be effective in ameliorating one or more clinical conditions associated with the patient's disease.

Stem cells are capable of both proliferation and giving rise to more progenitor cells, these in turn having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one aspect, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell that, itself, is derived from a multipotent cell, and so on. While each of these multipotent cells may be considered stem cells, the range of cell types that each can give rise to may vary considerably. Some differentiated cells also have the capacity to give rise to cells of greater developmental potential. Such capacity may be natural or may be induced artificially upon treatment with various factors. In many biological instances, stem cells can also be "multipotent" because they can produce progeny of more than one distinct cell type, but this is not required for "stem-ness."

Self-renewal can be another important aspect of the stem cell. In theory, self-renewal can occur by either of two major mechanisms. Stem cells can divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high-proliferative potential. Progenitor cells can give rise to multiple distinct differentiated cell types or to a single differentiated cell type, depending on the developmental pathway and on the environment in which the cells develop and differentiate.

In the context of cell ontogeny, the adjective "differentiated," or "differentiating" is a relative term. A "differentiated cell" is a cell that has progressed further down the developmental pathway than the cell to which it is being compared. Thus, stem cells can differentiate into lineage-restricted precursor cells (such as a myocyte progenitor cell), which in turn can differentiate into other types of precursor cells further down the pathway (such as a myocyte precursor), and then to an end-stage differentiated cell, such as a myocyte, which plays a characteristic role in a certain tissue type, and may or may not retain the capacity to proliferate further.

Induced Pluripotent Stem Cells

The genetically engineered human cells described herein can be induced pluripotent stem cells (iPSCs). An advantage of using iPSCs is that the cells can be derived from the same subject to which the progenitor cells are to be administered. That is, a somatic cell can be obtained from a subject, reprogrammed to an induced pluripotent stem cell, and then re-differentiated into a progenitor cell to be administered to the subject (e.g., autologous cells). Because the progenitors are essentially derived from an autologous source, the risk of engraftment rejection or allergic response can be reduced compared to the use of cells from another subject or group of subjects. In addition, the use of iPSCs negates the need for cells obtained from an embryonic source. Thus, in one aspect, the stem cells used in the disclosed methods are not embryonic stem cells.

Although differentiation is generally irreversible under physiological contexts, several methods have been recently developed to reprogram somatic cells to iPSCs. Exemplary methods are known to those of skill in the art and are described briefly herein below.

The term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. Reprogramming can encompass complete reversion of the differentiation state of a differentiated cell (e.g., a somatic cell) to a pluripotent state or a multipotent state. Reprogramming can encompass complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain examples described herein, reprogramming of a differentiated cell (e.g., a somatic cell) can cause the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a myogenic stem cell). Reprogramming is also distinct from promoting the self-renewal or proliferation of cells that are already pluripotent or multipotent, although the compositions and methods described herein can also be of use for such purposes, in some examples.

Many methods are known in the art that can be used to generate pluripotent stem cells from somatic cells. Any such method that reprograms a somatic cell to the pluripotent phenotype would be appropriate for use in the methods described herein.

Reprogramming methodologies for generating pluripotent cells using defined combinations of transcription factors have been described. Mouse somatic cells can be converted to ES cell-like cells with expanded developmental potential by the direct transduction of Oct4, Sox2, Klf4, and c-Myc; see, e.g., Takahashi and Yamanaka, Cell 126(4): 663-76 (2006). iPSCs resemble ES cells, as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germline transmission [see, e.g., Maherali and Hochedlinger, Cell Stem Cell. 3(6):595-605 (2008)], and tetraploid complementation.

Human iPSCs can be obtained using similar transduction methods, and the transcription factor trio, OCT4, SOX2, and NANOG, has been established as the core set of transcription factors that govern pluripotency; see, e.g., Budniatzky and Gepstein, Stem Cells Transl Med. 3(4):448-57 (2014); Barrett et al., Stem Cells Trans Med 3:1-6 sctm.2014-0121 (2014); Focosi et al., Blood Cancer Journal 4: e211 (2014); and references cited therein. The production of iPSCs can be achieved by the introduction of nucleic acid sequences encoding stem cell-associated genes into an adult, somatic cell, historically using viral vectors.

iPSCs can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 7(5):618-30 (2010). Reprogramming can be achieved by introducing a combination of nucleic acids encoding stem cell-associated genes, including, for example, Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. Reprogramming using the methods and compositions described herein can further comprise introducing one or more of Oct-3/4, a member of the Sox family, a member of the Klf family, and a member of the Myc family to a somatic cell. The methods and compositions described herein can further comprise introducing one or more of each of Oct-4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one aspect the reprogramming is not effected by a method that alters the genome. Thus, in such examples, reprogramming can be achieved, e.g., without the use of viral or plasmid vectors.

The efficiency of reprogramming (i.e., the number of reprogrammed cells) derived from a population of starting cells can be enhanced by the addition of various agents, e.g., small molecules, as shown by Shi et al., Cell-Stem Cell 2:525-528 (2008); Huangfu et al., Nature Biotechnology 26(7):795-797 (2008) and Marson et al., Cell-Stem Cell 3: 132-135 (2008). Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Titan Pharmaceuticals, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one case, for example, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. Detection can involve not only RT-PCR, but can also include detection of protein markers. Intracellular markers may be best identified via RT-PCR, or protein detection methods such as immunocytochemistry, while cell surface markers are readily identified, e.g., by immunocytochemistry.

The pluripotent stem cell character of isolated cells can be confirmed by tests evaluating the ability of the iPSCs to differentiate into cells of each of the three germ layers. As one example, teratoma formation in nude mice can be used to evaluate the pluripotent character of the isolated clones. The cells can be introduced into nude mice and histology and/or immunohistochemistry can be performed on a tumor arising from the cells. The growth of a tumor comprising cells from all three germ layers, for example, further indicates that the cells are pluripotent stem cells.

Cells of the Peripheral Nervous System

In some aspects, the genetically engineered human cells described herein are neurons and nerves outside of the brain and spinal cord. Neurons, which process information, and glial cells, which provide mechanical and metabolic support to the nervous system, are the two main classes of cells of the peripheral nervous system. Non-limiting examples of neurons include sensory neurons (collect impulses from the sensory receptors in areas such as skin, muscles, and organs and carries those impulses through the nerves to the CNS) and motor neurons (collect outgoing messages from the CNS and delivers them to the appropriate body organs, instructing them what action needs to be taken). Non-limiting examples of glial cells include Schwann cells in nerves or satellite cells in ganglia.

Creating Patient Specific iPSCs

One step of the ex vivo methods of the present disclosure can involve creating a patient specific iPS cell, patient specific iPS cells, or a patient specific iPS cell line. There are many established methods in the art for creating patient specific iPS cells, as described in Takahashi and Yamanaka 2006; Takahashi, Tanabe et al. 2007. For example, the creating step can comprise: a) isolating a somatic cell, such as a skin cell or fibroblast, from the patient; and b) introducing a set of pluripotency-associated genes into the somatic cell in order to induce the cell to become a pluripotent stem cell. The set of pluripotency-associated genes can be one or more of the genes selected from the group consisting of OCT4, SOX1, SOX2, SOX3, SOX15, SOX18, NANOG, KLF1, KLF2, KLF4, KLF5, c-MYC, n-MYC, REM2, TERT and LIN28.

Performing a Biopsy or Aspirate of the Patient's Tissue

A biopsy or aspirate is a sample of tissue or fluid taken from the body. There are many different kinds of biopsies or aspirates. Nearly all of them involve using a sharp tool to remove a small amount of tissue. If the biopsy will be on the skin or other sensitive area, numbing medicine can be applied first. A biopsy or aspirate may be performed according to any of the known methods in the art. For example, in a bone marrow aspirate, a large needle is used to enter the pelvis bone to collect bone marrow. For example, in the case of a nerve biopsy from skin or leg to isolate neurons of the peripheral nervous system, the nerve segment is excised inflicting minimal mechanical injury. Squeezing or stretching the nerve is avoided and excessive removal of fat or connective tissue is not attempted.

Isolating a Neuron of the Peripheral Nervous System

Neurons of the peripheral nervous system may be isolated according to any known method in the art. For example, the nerve segment is excised inflicting minimal mechanical injury under aseptic conditions. Squeezing or stretching the nerve is strictly avoided and excessive removal of fat or connective tissue is not attempted. Since, nerve fibers are very sensitive to mechanical injury, the proximal nerve cut is performed first. Following the isolation, the outermost connective tissue layer, the epineurium, is removed and collected for enzymatic digestion. The fibers are teased with the help of fine forceps until all fascicles are separated into individual fibers. The epineurium and teased fibers are then subjected to enzymatic digestion overnight with dispase II and type I collagenase. The digested products are filtered and collected by centrifugation. The resulting cell suspensions are plated onto adhesive PLL/laminin substrate. The adherent cells are cultured for analysis (Andersen et al., Scientific Reports-Nature, 2016, 6:31781).

Isolating a Mesenchymal Stem Cell

Mesenchymal stem cells can be isolated according to any method known in the art, such as from a patient's bone marrow or peripheral blood. For example, marrow aspirate can be collected into a syringe with heparin. Cells can be washed and centrifuged on a Percoll. The cells can be cultured in Dulbecco's modified Eagle's medium (DMEM) (low glucose) containing 10% fetal bovine serum (FBS) (Pittinger M F, Mackay A M, Beck S C et al., Science 1999; 284:143-147).

Genetically Modified Cells

The term "genetically modified cell" refers to a cell that comprises at least one genetic modification introduced by genome editing (e.g., using the CRISPR/Cas9 or CRISPR/Cpf1 system). In some ex vivo examples herein, the genetically modified cell can be genetically modified progenitor cell. In some in vivo examples herein, the genetically modified cell can be a genetically modified neuron of the peripheral nervous system. A genetically modified cell comprising an exogenous genome-targeting nucleic acid and/or an exogenous nucleic acid encoding a genome-targeting nucleic acid is contemplated herein.

The term "control treated population" describes a population of cells that has been treated with identical media, viral induction, nucleic acid sequences, temperature, confluency, flask size, pH, etc., with the exception of the addition of the genome editing components. Any method known in the art can be used to measure transcription of SCN9A gene or protein expression or activity, for example Western Blot analysis of the SCN9A protein or real time PCR for quantifying SCN9A mRNA.

The term "isolated cell" refers to a cell that has been removed from an organism in which it was originally found, or a descendant of such a cell. Optionally, the cell can be cultured in vitro, e.g., under defined conditions or in the presence of other cells. Optionally, the cell can be later introduced into a second organism or re-introduced into the organism from which it (or the cell from which it is descended) was isolated.

The term "isolated population" with respect to an isolated population of cells refers to a population of cells that has been removed and separated from a mixed or heterogeneous population of cells. In some cases, the isolated population can be a substantially pure population of cells, as compared to the heterogeneous population from which the cells were isolated or enriched. In some cases, the isolated population can be an isolated population of human progenitor cells, e.g., a substantially pure population of human progenitor cells, as compared to a heterogeneous population of cells comprising human progenitor cells and cells from which the human progenitor cells were derived.

The term "substantially enhanced," with respect to a particular cell population, refers to a population of cells in which the occurrence of a particular type of cell is increased relative to pre-existing or reference levels, by at least 2-fold, at least 3-, at least 4-, at least 5-, at least 6-, at least 7-, at least 8-, at least 9, at least 10-, at least 20-, at least 50-, at least 100-, at least 400-, at least 1000-, at least 5000-, at least 20000-, at least 100000- or more fold depending, e.g., on the desired levels of such cells for ameliorating pain.

The term "substantially enriched" with respect to a particular cell population, refers to a population of cells that is at least about 10%, about 20%, about 30%, about 40%, about 50%, about 60%, about 70% or more with respect to the cells making up a total cell population.

The term "substantially pure" with respect to a particular cell population, refers to a population of cells that is at least about 75%, at least about 85%, at least about 90%, or at least about 95% pure, with respect to the cells making up a total cell population. That is, the terms "substantially pure" or "essentially purified," with regard to a population of progenitor cells, refers to a population of cells that contain fewer than about 20%, about 15%, about 10%, about 9%, about 8%, about 7%, about 6%, about 5%, about 4%, about 3%, about 2%, about 1%, or less than 1%, of cells that are not progenitor cells as defined by the terms herein.

Differentiation of Genome-Edited iPSCs into Cells of the Peripheral Nervous System Another step of the ex vivo methods of the present disclosure can comprise differentiating the genome-edited iPSCs into cells of the peripheral nervous system (e.g., a neuron or a glial cell such as Schwann cell in nerves or satellite glial cell in ganglia). The differentiating step may be performed according to any method known in the art. For example, neuronal differentiation of iPSCs is induced using a combination of brain-derived neurotrophic factor (BDNF), glial cell-derived neurotrophic factor (GDNF), nerve growth factor (NGF) and dibutyryl cyclic AMP (dbcAMP). Then, the iPSCs-derived neural cells are further differentiated into Schwann cells using ciliary neurotrophic factor (CNTF), neuregulin 1β and dbcAMP (Wang et al., Biomaterials. 2011; 32(22): 5023-5032).

Differentiation of Genome-Edited Mesenchymal Stem Cells into Cells of the Peripheral Nervous System Another step of the ex vivo methods of the present disclosure can comprise differentiating the genome-edited mesenchymal stem cells into cells of the peripheral nervous system (e.g., a neuron or a glial cell such as Schwann cell in nerves or satellite glial cell in ganglia). The differentiating step may be performed according to any method known in the art. For example, MSC are treated with various factors and hormones, including basic fibroblast growth factor, human recombinant platelet derived growth factor, forskolin, and glial growth factor-2 (Ladak et al., Experimental Neurology 228 (2011) 242-252).

Implanting Cells into Patients

Another step of the ex vivo methods of the present disclosure can comprise implanting the genome-edited neurons of the peripheral nervous system into patients. This implanting step may be accomplished using any method of implantation known in the art. For example, the genetically modified cells may be injected directly in the patient's blood or otherwise administered to the patient.

III. Formulations and Delivery

Pharmaceutically Acceptable Carriers

The ex vivo methods of administering progenitor cells to a subject contemplated herein involve the use of therapeutic compositions comprising progenitor cells.

Therapeutic compositions can contain a physiologically tolerable carrier together with the cell composition, and optionally at least one additional bioactive agent as described herein, dissolved or dispersed therein as an active ingredient. In some cases, the therapeutic composition is not substantially immunogenic when administered to a mammal or human patient for therapeutic purposes, unless so desired.

In general, the progenitor cells described herein can be administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the progenitor cells, as described herein, using routine experimentation.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition can depend on the nature of the disorder or condition, and can be determined by standard clinical techniques.

Guide RNA Formulation

Guide RNAs of the present disclosure can be formulated with pharmaceutically acceptable excipients such as carriers, solvents, stabilizers, adjuvants, diluents, etc., depending upon the particular mode of administration and dosage form. Guide RNA compositions can be formulated to achieve a physiologically compatible pH, and range from a pH of about 3 to a pH of about 11, about pH 3 to about pH 7, depending on the formulation and route of administration. In some cases, the pH can be adjusted to a range from about pH 5.0 to about pH 8. In some cases, the compositions can comprise a therapeutically effective amount of at least one compound as described herein, together with one or more pharmaceutically acceptable excipients. Optionally, the compositions can comprise a combination of the compounds described herein, or can include a second active ingredient useful in the treatment or prevention of bacterial growth (for example and without limitation, anti-bacterial or anti-microbial agents), or can include a combination of reagents of the present disclosure.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Delivery

Guide RNA polynucleotides (RNA or DNA) and/or endonuclease polynucleotide(s) (RNA or DNA) can be delivered by viral or non-viral delivery vehicles known in the art. Alternatively, endonuclease polypeptide(s) can be delivered by viral or non-viral delivery vehicles known in the art, such as electroporation or lipid nanoparticles. In further alternative aspects, the DNA endonuclease can be delivered as one or more polypeptides, either alone or pre-complexed with one or more guide RNAs, or one or more crRNA together with a tracrRNA.

Polynucleotides can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 18: 1127-1133 (2011) (which focuses on non-viral delivery vehicles for siRNA that are also useful for delivery of other polynucleotides).

For polynucleotides of the present disclosure, the formulation may be selected from any of those taught, for example, in International Application PCT/US2012/069610.

Polynucleotides, such as guide RNA, sgRNA, and mRNA encoding an endonuclease, may be delivered to a cell or a patient by a lipid nanoparticle (LNP).

A LNP refers to any particle having a diameter of less than 1000 nm, 500 nm, 250 nm, 200 nm, 150 nm, 100 nm, 75 nm, 50 nm, or 25 nm. Alternatively, a nanoparticle may range in size from 1-1000 nm, 1-500 nm, 1-250 nm, 25-200 nm, 25-100 nm, 35-75 nm, or 25-60 nm.

LNPs may be made from cationic, anionic, or neutral lipids. Neutral lipids, such as the fusogenic phospholipid DOPE or the membrane component cholesterol, may be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses.

LNPs may also be comprised of hydrophobic lipids, hydrophilic lipids, or both hydrophobic and hydrophilic lipids.

Any lipid or combination of lipids that are known in the art can be used to produce a LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

The lipids can be combined in any number of molar ratios to produce a LNP. In addition, the polynucleotide(s) can be combined with lipid(s) in a wide range of molar ratios to produce a LNP.

As stated previously, the site-directed polypeptide and genome-targeting nucleic acid can each be administered separately to a cell or a patient. On the other hand, the site-directed polypeptide can be pre-complexed with one or more guide RNAs, or one or more crRNA together with a tracrRNA. The pre-complexed material can then be administered to a cell or a patient. Such pre-complexed material is known as a ribonucleoprotein particle (RNP).

RNA is capable of forming specific interactions with RNA or DNA. While this property is exploited in many biological processes, it also comes with the risk of promiscuous interactions in a nucleic acid-rich cellular environment. One solution to this problem is the formation of ribonucleoprotein particles (RNPs), in which the RNA is pre-complexed with an endonuclease. Another benefit of the RNP is protection of the RNA from degradation.

The endonuclease in the RNP can be modified or unmodified. Likewise, the gRNA, crRNA, tracrRNA, or sgRNA can be modified or unmodified. Numerous modifications are known in the art and can be used.

The endonuclease and sgRNA can be generally combined in a 1:1 molar ratio. Alternatively, the endonuclease, crRNA and tracrRNA can be generally combined in a 1:1:1 molar ratio. However, a wide range of molar ratios can be used to produce a RNP.

AAV (Adeno Associated Virus)

A recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived, and may be from a different AAV serotype than the rAAV genome ITRs, including, but not limited to, AAV serotypes described herein. Production of pseudotyped rAAV is disclosed in, for example, international patent application publication number WO 01/83692.

AAV Serotypes

AAV particles packaging polynucleotides encoding compositions of the present disclosure, e.g., endonucleases, donor sequences, or RNA guide molecules, of the present disclosure may comprise or be derived from any natural or recombinant AAV serotype. According to the present disclosure, the AAV particles may utilize or be based on a serotype selected from any of the following serotypes, and variants thereof including but not limited to AAV1, AAV10, AAV106.1/hu.37, AAV11, AAV114.3/hu.40, AAV12, AAV127.2/hu.41, AAV127.5/hu.42, AAV128.1/hu.43, AAV128.3/hu.44, AAV130.4/hu.48, AAV145.1/hu.53, AAV145.5/hu.54, AAV145.6/hu.55, AAV16.12/hu.11, AAV16.3, AAV16.8/hu.10, AAV161.10/hu.60, AAV161.6/hu.61, AAV1-7/rh.48, AAV1-8/rh.49, AAV2, AAV2.5T, AAV2-15/rh.62, AAV223.1, AAV223.2, AAV223.4, AAV223.5, AAV223.6, AAV223.7, AAV2-3/rh.61, AAV24.1, AAV2-4/rh.50, AAV2-5/rh.51, AAV27.3, AAV29.3/bb.1, AAV29.5/bb.2, AAV2G9, AAV-2-pre-miRNA-101, AAV3, AAV3.1/hu.6, AAV3.1/hu.9, AAV3-11/rh.53, AAV3-3, AAV33.12/hu.17, AAV33.4/hu.15, AAV33.8/hu.16, AAV3-9/rh.52, AAV3a, AAV3b, AAV4, AAV4-19/rh.55, AAV42.12, AAV42-10, AAV42-11, AAV42-12, AAV42-13, AAV42-15, AAV42-1b, AAV42-2, AAV42-3a, AAV42-3b, AAV42-4, AAV42-5a, AAV42-5b, AAV42-6b, AAV42-8, AAV42-aa, AAV43-1, AAV43-12, AAV43-20, AAV43-21, AAV43-23, AAV43-25, AAV43-5, AAV4-4, AAV44.1, AAV44.2, AAV44.5, AAV46.2/hu.28, AAV46.6/hu.29, AAV4-8/r11.64, AAV4-8/rh.64, AAV4-9/rh.54, AAV5, AAV52.1/hu.20, AAV52/hu.19, AAV5-22/rh.58, AAV5-3/rh.57, AAV54.1/hu.21, AAV54.2/hu.22, AAV54.4R/hu.27, AAV54.5/hu.23, AAV54.7/hu.24, AAV58.2/hu.25, AAV6, AAV6.1, AAV6.1.2, AAV6.2, AAV7, AAV7.2, AAV7.3/hu.7, AAV8, AAV-8b, AAV-8h, AAV9, AAV9.11, AAV9.13, AAV9.16, AAV9.24, AAV9.45, AAV9.47, AAV9.61, AAV9.68, AAV9.84, AAV9.9, AAVA3.3, AAVA3.4, AAVA3.5, AAVA3.7, AAV-b, AAVC1, AAVC2, AAVC5, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAV-DJ, AAV-DJ8, AAVF3, AAVF5, AAV-h, AAVH-1/hu.1, AAVH2, AAVH-5/hu.3, AAVH6, AAVhE1.1, AAVhER1.14, AAVhEr1.16, AAVhEr1.18, AAVhER1.23, AAVhEr1.35, AAVhEr1.36, AAVhEr1.5, AAVhEr1.7, AAVhEr1.8, AAVhEr2.16, AAVhEr2.29, AAVhEr2.30, AAVhEr2.31, AAVhEr2.36, AAVhEr2.4, AAVhEr3.1, AAVhu.1, AAVhu.10, AAVhu.11, AAVhu.11, AAVhu.12, AAVhu.13, AAVhu.14/9, AAVhu.15, AAVhu.16, AAVhu.17, AAVhu.18, AAVhu.19, AAVhu.2, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.3, AAVhu.31, AAVhu.32, AAVhu.34, AAVhu.35, AAVhu.37, AAVhu.39, AAVhu.4, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.5, AAVhu.51, AAVhu.52, AAVhu.53, AAVhu.54, AAVhu.55, AAVhu.56, AAVhu.57, AAVhu.58, AAVhu.6, AAVhu.60, AAVhu.61, AAVhu.63, AAVhu.64, AAVhu.66, AAVhu.67, AAVhu.7, AAVhu.8, AAVhu.9, AAVhu.t 19, AAVLG-10/rh.40, AAVLG-4/rh.38, AAVLG-9/hu.39, AAVLG-9/hu.39, AAV-LK01, AAV-LK02, AAVLK03, AAV-LK03, AAV- LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK17, AAV-LK18, AAV-LK19, AAVN721-8/rh.43, AAV-PAEC, AAV-PAEC11, AAV-PAEC12, AAV-PAEC2, AAV-PAEC4, AAV-PAEC6, AAV-PAEC7, AAV-PAEC8, AAVpi.1, AAVpi.2, AAVpi.3, AAVrh.10, AAVrh.12, AAVrh.13, AAVrh.13R, AAVrh.14, AAVrh.17, AAVrh.18, AAVrh.19, AAVrh.2, AAVrh.20, AAVrh.21, AAVrh.22, AAVrh.23, AAVrh.24, AAVrh.25, AAVrh.2R, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.43, AAVrh.44, AAVrh.45, AAVrh.46, AAVrh.47, AAVrh.48, AAVrh.48, AAVrh.48.1, AAVrh.48.1.2, AAVrh.48.2, AAVrh.49, AAVrh.50, AAVrh.51, AAVrh.52, AAVrh.53, AAVrh.54, AAVrh.55, AAVrh.56, AAVrh.57, AAVrh.58, AAVrh.59, AAVrh.60, AAVrh.61, AAVrh.62, AAVrh.64, AAVrh.64R1, AAVrh.64R2, AAVrh.65, AAVrh.67, AAVrh.68, AAVrh.69, AAVrh.70, AAVrh.72, AAVrh.73, AAVrh.74, AAVrh.8, AAVrh.8R, AAVrh8R, AAVrh8R A586R mutant, AAVrh8R R533A mutant, BAAV, BNP61 AAV, BNP62 AAV, BNP63 AAV, bovine AAV, caprine AAV, Japanese AAV 10, true type AAV (ttAAV), UPENN AAV 10, AAV-LK16, AAAV, AAV Shuffle 100-1, AAV Shuffle 100-2, AAV Shuffle 100-3, AAV Shuffle 100-7, AAV Shuffle 10-2, AAV Shuffle 10-6, AAV Shuffle 10-8, AAV SM 100-10, AAV SM 100-3, AAV SM 10-1, AAV SM 10-2, and/or AAV SM 10-8.

In some aspects, the AAV serotype may be, or have, a mutation in the AAV9 sequence as described by N Pulicherla et al. (Molecular Therapy 19(6):1070-1078 (2011)), such as but not limited to, AAV9.9, AAV9.11, AAV9.13, AAV9.16, AAV9.24, AAV9.45, AAV9.47, AAV9.61, AAV9.68, AAV9.84.

In some aspects, the AAV serotype may be, or have, a sequence as described in U.S. Pat. No. 6,156,303, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S. Pat. No. 6,156,303), AAV3A (SEQ ID NO: 4 and 9, of U.S. Pat. No. 6,156,303), or derivatives thereof.

In some aspects, the serotype may be AAVDJ or a variant thereof, such as AAVDJ8 (or AAV-DJ8), as described by Grimm et al. (Journal of Virology 82(12): 5887-5911 (2008)). The amino acid sequence of AAVDJ8 may comprise two or more mutations in order to remove the heparin binding domain (HBD). As a non-limiting example, the AAV-DJ sequence described as SEQ ID NO: 1 in U.S. Pat. No. 7,588,772, may comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, may comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In some aspects, the AAV serotype may be, or have, a sequence as described in International Publication No. WO2015121501, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present disclosure, AAV capsid serotype selection or use may be from a variety of species. In one example, the AAV may be an avian AAV (AAAV). The AAAV serotype may be, or have, a sequence as described in U.S. Pat. No. 9,238,800, such as, but not limited to, AAAV (SEQ ID NO: 1, 2, 4, 6, 8, 10, 12, and 14 of U.S. Pat. No. 9,238,800), or variants thereof.

In one example, the AAV may be a bovine AAV (BAAV). The BAAV serotype may be, or have, a sequence as described in U.S. Pat. No. 9,193,769, such as, but not limited to, BAAV (SEQ ID NO: 1 and 6 of U.S. Pat. No. 9,193,769), or variants thereof. The BAAV serotype may be or have a sequence as described in U.S. Pat. No. 7,427,396, such as, but not limited to, BAAV (SEQ ID NO: 5 and 6 of U.S. Pat. No. 7,427,396), or variants thereof.

In one example, the AAV may be a caprine AAV. The caprine AAV serotype may be, or have, a sequence as described in U.S. Pat. No. 7,427,396, such as, but not limited to, caprine AAV (SEQ ID NO: 3 of U.S. Pat. No. 7,427,396), or variants thereof.

In other examples, the AAV may be engineered as a hybrid AAV from two or more parental serotypes. In one example, the AAV may be AAV2G9 which comprises sequences from AAV2 and AAV9. The AAV2G9 AAV serotype may be, or have, a sequence as described in U.S. Patent Publication No. 20160017005.

In one example, the AAV may be a serotype generated by the AAV9 capsid library with mutations in amino acids 390-627 (VP1 numbering) as described by Pulicherla et al. (Molecular Therapy 19(6):1070-1078 (2011). The serotype and corresponding nucleotide and amino acid substitutions may be, but is not limited to, AAV9.1 (G1594C; D532H), AAV6.2 (T1418A and T1436X; V473D and I479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V606I), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T582I), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A; T492I, H527N), AAV.59 (T1336C; Y446H), AAV9.61 (A1493T; N498I), AAV9.64 (C1531A, A1617T; L511I), AAV9.65 (C1335T, T1530C, C1568A; A523D), AAV9.68 (C1510A; P504T), AAV9.80 (G1441A,G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K528I), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In one example, the AAV may be a serotype comprising at least one AAV capsid CD8+ T-cell epitope. As a non-limiting example, the serotype may be AAV1, AAV2 or AAV8.

In one example, the AAV may be a variant, such as PHP.A or PHP.B as described in Deverman. 2016. Nature Biotechnology. 34(2): 204-209.

In one example, the AAV may be a serotype selected from any of those found in SEQ ID NOs: 4734-5302 and Table 2.

In one example, the AAV may be encoded by a sequence, fragment or variant as disclosed in SEQ ID NOs: 4734-5302 and Table 2.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

AAV vector serotypes can be matched to target cell types. For example, the following exemplary cell types can be transduced by the indicated AAV serotypes among others.

TABLE 2

Tissue/Cell Types and Serotypes

| Tissue/Cell Type | Serotype |
| --- | --- |
| Liver | AAV3, AAV8, AAV5, AAV9 |
| Skeletal muscle | AAV1, AAV7, AAV6, AAV8, AAV9 |
| Central nervous system | AAV5, AAV1, AAV4, AAV9 |
| RPE | AAV5, AAV4 |
| Photoreceptor cells | AAV5 |
| Lung | AAV9 |
| Heart | AAV8 |
| Pancreas | AAV8 |
| Kidney | AAV2, AAV8 |
| Hematopoietic stem cells | AAV6 |

In addition to adeno-associated viral vectors, other viral vectors can be used. Such viral vectors include, but are not limited to, lentivirus, alphavirus, enterovirus, pestivirus, baculovirus, herpesvirus, Epstein Barr virus, papovavirus, poxvirus, vaccinia virus, and herpes simplex virus.

In some aspects, Cas9 mRNA, sgRNA targeting one or two sites in SCN9A gene, and donor DNA can each be separately formulated into lipid nanoparticles, or are all co-formulated into one lipid nanoparticle.

In some aspects, Cas9 mRNA can be formulated in a lipid nanoparticle, while sgRNA and donor DNA can be delivered in an AAV vector.

Options are available to deliver the Cas9 nuclease as a DNA plasmid, as mRNA or as a protein. The guide RNA can be expressed from the same DNA, or can also be delivered as an RNA. The RNA can be chemically modified to alter or improve its half-life, or decrease the likelihood or degree of immune response. The endonuclease protein can be complexed with the gRNA prior to delivery. Viral vectors allow efficient delivery; split versions of Cas9 and smaller orthologs of Cas9 can be packaged in AAV, as can donors for HDR. A range of non-viral delivery methods also exist that can deliver each of these components, or non-viral and viral methods can be employed in tandem. For example, nanoparticles can be used to deliver the protein and guide RNA, while AAV can be used to deliver a donor DNA.

In some aspects of the in vivo based therapy described herein, the viral vector(s) encoding the endonuclease, guide RNA and/or donor DNA may be delivered to the neurons of the peripheral neural system, such as primary sensory and motor neurons, via direct intraganglionic or intraspinal injection, or intrathecal delivery (Hoyng et al., Front Mol Neurosci. 2015 Jul. 15; 8:32).

IV. Dosing and Administration

The terms "administering," "introducing" and "transplanting" are used interchangeably in the context of the placement of cells, e.g., progenitor cells, into a subject, by a method or route that results in at least partial localization of the introduced cells at a desired site, such as a site of injury or repair, such that a desired effect(s) is produced. The cells e.g., progenitor cells, or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the patient, i.e., long-term engraftment. For example, in some aspects described herein, an effective amount of progenitor cells is administered via a systemic route of administration, such as an intraperitoneal or intravenous route.

The terms "individual," "subject," "host" and "patient" are used interchangeably herein and refer to any subject for whom diagnosis, treatment or therapy is desired. In some aspects, the subject is a mammal. In some aspects, the subject is a human being.

When provided prophylactically, progenitor cells described herein can be administered to a subject in advance of any symptom of pain. Accordingly, the prophylactic administration of a progenitor cell population serves to prevent pain.

A progenitor cell population being administered according to the methods described herein can comprise allogeneic progenitor cells obtained from one or more donors. Such progenitors may be of any cellular or tissue origin, e.g., liver, muscle, cardiac, etc. "Allogeneic" refers to a progenitor cell or biological samples comprising progenitor cells obtained from one or more different donors of the same species, where the genes at one or more loci are not identical. For example, a liver progenitor cell population being administered to a subject can be derived from one more unrelated donor subjects, or from one or more non-identical siblings. In some cases, syngeneic progenitor cell populations can be used, such as those obtained from genetically identical animals, or from identical twins. The progenitor cells can be autologous cells; that is, the progenitor cells are obtained or isolated from a subject and administered to the same subject, i.e., the donor and recipient are the same.

The term "effective amount" refers to the amount of a population of progenitor cells or their progeny needed to prevent or alleviate at least one or more signs or symptoms of pain, and relates to a sufficient amount of a composition to provide the desired effect, e.g., to treat a subject having pain. The term "therapeutically effective amount" therefore refers to an amount of progenitor cells or a composition comprising progenitor cells that is sufficient to promote a particular effect when administered to a typical subject, such as one who has or is at risk for pain. An effective amount would also include an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate "effective amount" can be determined by one of ordinary skill in the art using routine experimentation.

For use in the various aspects described herein, an effective amount of progenitor cells comprises at least $10^2$ progenitor cells, at least $5 \times 10^2$ progenitor cells, at least $10^3$ progenitor cells, at least $5 \times 10^3$ progenitor cells, at least $10^4$ progenitor cells, at least $5 \times 10^4$ progenitor cells, at least $10^5$ progenitor cells, at least $2 \times 10^5$ progenitor cells, at least $3 \times 10^5$ progenitor cells, at least $4 \times 10^5$ progenitor cells, at least $5 \times 10^5$ progenitor cells, at least $6 \times 10^5$ progenitor cells, at least $7 \times 10^5$ progenitor cells, at least $8 \times 10^5$ progenitor cells, at least $9 \times 10^5$ progenitor cells, at least $1 \times 10^6$ progenitor cells, at least $2 \times 10^6$ progenitor cells, at least $3 \times 10^6$ progenitor cells, at least $4 \times 10^6$ progenitor cells, at least $5 \times 10^6$ progenitor cells, at least $6 \times 10^6$ progenitor cells, at least $7 \times 10^6$ progenitor cells, at least $8 \times 10^6$ progenitor cells, at least $9 \times 10^6$ progenitor cells, or multiples thereof. The progenitor cells can be derived from one or more donors, or can be obtained from an autologous source. In some examples described herein, the progenitor cells can be expanded in culture prior to administration to a subject in need thereof.

Modest and incremental decreases in the levels of SCN9A expressed in cells of patients having pain can be beneficial for ameliorating one or more symptoms of the disease, for increasing long-term survival, and/or for reducing side effects associated with other treatments. Upon administration of such cells to human patients, the presence of progenitors that are producing decreased levels of SCN9A is beneficial. In some cases, effective treatment of a subject gives rise to at least about 3%, 5% or 7% reduction in SCN9A relative to total SCN9A in the treated subject. In some examples, the reduction in SCN9A will be at least about 10% of total SCN9A. In some examples, the reduction in SCN9A will be at least about 20% to 30% of total SCN9A. Similarly, the introduction of even relatively limited subpopulations of cells having significantly reduced levels of SCN9A can be beneficial in various patients because in some situations normalized cells will have a selective advantage relative to diseased cells. However, even modest levels of progenitors with reduced levels of SCN9A can be beneficial for ameliorating one or more aspects of Pain in patients. In some examples, about 10%, about 20%, about 30%, about 40%, about 50%, about 60%, about 70%, about 80%, about 90% or more of the progenitors in patients to whom such cells are administered are producing decreased levels of SCN9A.

"Administered" refers to the delivery of a progenitor cell composition into a subject by a method or route that results in at least partial localization of the cell composition at a desired site. A cell composition can be administered by any appropriate route that results in effective treatment in the subject, i.e. administration results in delivery to a desired location in the subject where at least a portion of the composition delivered, i.e. at least $1 \times 10^4$ cells are delivered to the desired site for a period of time.

In one aspect of the method, the pharmaceutical composition may be administered via a route such as, but not limited to, enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration, which is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis and spinal.

Modes of administration include injection, infusion, instillation, and/or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some examples, the route is intravenous. For the delivery of cells, administration by injection or infusion can be made.

The cells can be administered systemically. The phrases "systemic administration," "administered systemically", "peripheral administration" and "administered peripherally" refer to the administration of a population of progenitor cells other than directly into a target site, tissue, or organ, such that it enters, instead, the subject's circulatory system and, thus, is subject to metabolism and other like processes.

The efficacy of a treatment comprising a composition for the treatment of pain can be determined by the skilled clinician. However, a treatment is considered "effective treatment," if any one or all of the signs or symptoms of, as but one example, levels of SCN9A are altered in a beneficial manner (e.g., decreased by at least 10%), or other clinically accepted symptoms or markers of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

The treatment according to the present disclosure can ameliorate one or more symptoms associated with pain by decreasing or altering the amount of the SCN9A protein in the individual.

V. Features and Properties of the Sodium Channel, Voltage Gated, Type IX Alpha Subunit (Scn9a) Gene SCN9A has been associated with diseases and disorders such as, but not limited to, Congenital Pain Insensitivity, Anosmia, As If Personality, Borderline Personality Disorder, Malignant neoplasm of breast, Non-Small Cell Lung Carcinoma, Cold intolerance, Febrile Convulsions, Diabetes, Diabetes Mellitus, Dissociative disorder, Epilepsy, Erythromelalgia, Primary Erythermalgia, Facial Pain, Herpesviridae Infections, Hereditary Sensory Autonomic Neuropathy Type 5, Hyperplasia, Neuralgia, Hereditary Sensory and Autonomic Neuropathies, Degenerative polyarthritis, Pain, Pain in limb, Postoperative Pain, Parkinson Disease, Postherpetic neuralgia, Prostatic Neoplasms, Pruritus, Seizures, Somatoform Disorder, Tobacco Use Disorder, Trigeminal Neuralgia, Synovial Cyst, Chronic pain, Acute onset pain, Paramyotonia Congenita (disorder), Malaise, Sensory Discomfort, Burning Pain, Indifference to pain, Inflammatory pain, Mechanical pain, Scalp pain, Hereditary Motor and Sensory-Neuropathy Type II, Common Migraine, Absence of pain sensation, Malignant neoplasm of prostate, Pain Disorder, Knee Osteoarthritis, Neuropathy, Complex Regional Pain Syndromes, Tonic-clonic seizures, Inherited neuropathies, Prostate carcinoma, Breast Carcinoma, Infantile Severe Myoclonic Epilepsy, Myxoid cyst, Channelopathies, Paroxysmal Extreme Pain Disorder, Painful Neuropathy, Compressive Neuropathies, Congenital Indifference to Pain Autosomal Recessive, Generalized Epilepsy With Febrile Seizures Plus Type 2, Generalized Epilepsy With Febrile Seizures Plus 7, Febrile Seizures Familial 3B, and Small Fiber Neuropathy (Adult-onset is referred to as small fiber neuropathy). Editing the SCN9A gene using any of the methods described herein may be used to treat, prevent and/or mitigate the symptoms of the diseases and disorders described herein.

The SCN9A gene encodes the alpha subunit of a sodium channel named NaV1.7. NaV1.7 is primarily expressed in sensory neurons and plays a significant role in nociception signaling. Mutations in the SCN9A gene are known to cause pain perception disorders, including primary erythermalgia, paroxysmal extreme pain disorder, congenital insensitivity to pain, and small fiber neuropathy. Gain-of-function mutations in the SCN9A gene result in spontaneous pain as observed in primary erythermalgia and paroxysmal extreme pain disorder. Thus, knock-out or knock-down of the SCN9A gene in patients having primary erythromelalgia or paroxysmal extreme pain disorder can be used to treat, prevent and/or mitigate the associated symptoms.

Primary erythromelalgia is a rare autosomal dominant disorder characterized by episodes of burning pain in the feet and hands in response to heat and movement. Affected individuals typically develop signs and symptoms in early childhood, although in milder cases symptoms can appear later in life. Management of this condition is mainly symptomatic. Besides avoidance of pain triggers (such as heat, exercise, and alcohol), treatment options include cooling and elevating the extremity, use of anesthetics such as lidocaine and mexilitine, and use of opioid drugs in extreme cases.

Paroxysmal extreme pain disorder is another rare disorder characterized by severe episodic pain in rectal, ocular, and mandibular regions as well as skin redness. Symptoms of this condition often begin in the neonatal period or in the early childhood, and can retain throughout life. Agents for treating chronic neuropathic pain disorders are often used to alleviate the pain episodes caused by the disease. Carbamazepine, a sodium channel blocker, has proven most effective of these treatments.

In one example, the gene is Sodium Channel, Voltage Gated, Type IX Alpha Subunit (SCN9A) which may also be referred to Sodium Voltage-Gated Channel Alpha Subunit 9, Sodium Channel, Voltage-Gated, Type IX, Alpha Polypeptide, Voltage-Gated Sodium Channel Subunit Alpha Nav1.7, Sodium Channel Protein Type IX Subunit Alpha, Neuroendocrine Sodium Channel, Peripheral Sodium Channel 1, HNE-Na, NENA, PN1, GEFSP7, HSAN2D, Nav1.7, FEB3B, ETHA, and SFNP. SCN9A has a cytogenetic location of 2q24.3 and the genomic coordinate are on Chromosome 2 on the forward strand at position 166,195,185-166,375,993. The nucleotide sequence of SCN9A is shown as SEQ ID NO: 5303. SCN7A is the gene upstream of SCN9A on the reverse strand and RN7SKP152 is the gene downstream of SCN9A on the reverse strand. AC010127.3 is a gene located on the forward strand opposite of SCN9A. SCN9A has a NCBI gene ID of 6335, Uniprot ID of Q15858 and Ensembl Gene ID of ENSG00000169432. SCN9A has 3906 SNPs, 39 introns and 38 exons. The exon identifier from Ensembl and the start/stop sites of the introns and exons are shown in Table 3.

TABLE 3

Introns and Exons for SCN9A

| Exon No. | Exon ID | Start/Stop | Intron No. | Intron based on Exon ID | Start/Stop |
|---|---|---|---|---|---|
| EX1 | ENSE00001589707 | 166,375,993-166,375,697 | INT1 | Intron ENSE00001589707-ENSE00001584414 | 166,375,696-166,311,807 |
| EX2 | ENSE00001584414 | 166,311,806-166,311,499 | INT2 | Intron ENSE00001584414-ENSE00001585608 | 166,311,498-166,307,075 |
| EX3 | ENSE00001585608 | 166,307,074-166,306,956 | INT3 | Intron ENSE00001585608-ENSE00001578488 | 166,306,955-166,306,600 |
| EX4 | ENSE00001578488 | 166,306,599-166,306,510 | INT4 | Intron ENSE00001578488-ENSE00003608010 | 166,306,509-166,305,921 |
| EX5 | ENSE00003608010 | 166,305,920-166,305,792 | INT5 | Intron ENSE00003608010-ENSE00003584389 | 166,305,791-166,304,330 |
| EX6 | ENSE00003584389 | 166,304,329-166,304,238 | INT6 | Intron ENSE00003584389-ENSE00001129637 | 166,304,237-166,303,303 |
| EX7 | ENSE00001129637 | 166,303,302-166,303,090 | INT7 | Intron ENSE00001129637-ENSE00001128428 | 166,303,089-166,294,663 |
| EX8 | ENSE00001128428 | 166,294,662-166,294,599 | INT8 | Intron ENSE00001128428-ENSE00001128421 | 166,294,598-166,293,373 |
| EX9 | ENSE00001128421 | 166,293,372-166,293,231 | INT9 | Intron ENSE00001128421-ENSE00001128530 | 166,293,230-166,288,644 |
| EX10 | ENSE00001128530 | 166,288,643-166,288,437 | INT10 | Intron ENSE00001128530-ENSE00001128525 | 166,288,436-166,286,624 |
| EX11 | ENSE00001128525 | 166,286,623-166,286,336 | INT11 | Intron ENSE00001128525-ENSE00001585370 | 166,286,335-166,284,825 |
| EX12 | ENSE00001585370 | 166,284,824-166,284,486 | INT12 | Intron ENSE00001585370-ENSE00001128510 | 166,284,485-166,281,809 |
| EX13 | ENSE00001128510 | 166,281,808-166,281,679 | INT13 | Intron ENSE00001128510-ENSE00001128413 | 166,281,678-166,280,596 |
| EX14 | ENSE00001128413 | 166,280,595-166,280,357 | INT14 | Intron ENSE00001128413-ENSE00002474880 | 166,280,356-166,278,314 |
| EX15 | ENSE00002474880 | 166,278,313-166,278,140 | INT15 | Intron ENSE00002474880-ENSE00002495223 | 166,278,139-166,277,340 |
| EX16 | ENSE00002495223 | 166,277,339-166,276,983 | INT16 | Intron ENSE00002495223-ENSE00001128485 | 166,276,982-166,272,876 |
| EX17 | ENSE00001128485 | 166,272,875-166,272,399 | INT17 | Intron ENSE00001128485-ENSE00001128480 | 166,272,398-166,251,886 |
| EX18 | ENSE00001128480 | 166,251,885-166,251,765 | INT18 | Intron ENSE00001128480-ENSE00001128404 | 166,251,764-166,242,657 |
| EX19 | ENSE00001128404 | 166,242,656-166,242,502 | INT19 | Intron ENSE00001128404-ENSE00001128471 | 166,242,501-166,238,268 |
| EX20 | ENSE00001128471 | 166,238,267-166,238,094 | INT20 | Intron ENSE00001128471-ENSE00001128466 | 166,238,093-166,233,463 |
| EX21 | ENSE00001128466 | 166,233,462-166,233,340 | INT21 | Intron ENSE00001128466-ENSE00001128459 | 166,233,339-166,228,973 |
| EX22 | ENSE00001128459 | 166,228,972-166,228,691 | INT22 | Intron ENSE00001128459-ENSE00001128456 | 166,228,690-166,227,724 |
| EX23 | ENSE00001128456 | 166,227,723-166,227,670 | INT23 | Intron ENSE00001128456-ENSE00002481484 | 166,227,669-166,226,705 |
| EX24 | ENSE00002481484 | 166,226,704-166,226,567 | INT24 | Intron ENSE00002481484-ENSE00001128397 | 166,226,566-166,204,465 |
| EX25 | ENSE00001128397 | 166,204,464-166,204,360 | INT25 | Intron ENSE00001128397-ENSE00001128443 | 166,204,359-166,204,226 |
| EX26 | ENSE00001128443 | 166,204,225-166,203,955 | INT26 | Intron ENSE00001128443-ENSE00001128389 | 166,203,954-166,199,865 |
| EX27 | ENSE00001128389 | 166,199,864-166,195,185 | INT27 | Intron ENSE00001638161-ENSE00003608010 | 166,306,509-166,305,921 |
| EX28 | ENSE00001638161 | 166,306,571-166,306,510 | INT28 | Intron ENSE00003608010-ENSE00002527733 | 166,305,791-166,304,123 |
| EX29 | ENSE00002527733 | 166,304,122-166,304,031 | INT29 | Intron ENSE00002527733-ENSE00001129637 | 166,304,030-166,303,303 |
| EX30 | ENSE00001728682 | 166,281,808-166,281,760 | INT30 | Intron ENSE00001585370-ENSE00001728682 | 166,284,485-166,281,809 |
| EX31 | ENSE00001128517 | 166,284,824-166,284,453 | INT31 | Intron ENSE00001128525-ENSE00001128517 | 166,286,335-166,284,825 |
| EX32 | ENSE00001578080 | 166,311,756-166,311,499 | INT32 | Intron ENSE00001128517-ENSE00001728682 | 166,284,452-166,281,809 |
| EX33 | ENSE00001577861 | 166,199,864-166,198,672 | INT33 | Intron ENSE00001578080-ENSE00001585608 | 166,311,498-166,307,075 |
| EX34 | ENSE00003545902 | 166,305,920-166,305,792 | INT34 | Intron ENSE00001128517-ENSE00001128510 | 166,284,452-166,281,809 |

TABLE 3-continued

Introns and Exons for SCN9A

| Exon No. | Exon ID | Start/Stop | Intron No. | Intron based on Exon ID | Start/Stop |
|---|---|---|---|---|---|
| EX35 | ENSE00003645381 | 166,304,329-166,304,238 | INT35 | Intron ENSE00001128443-ENSE00001577861 | 166,203,954-166,199,865 |
| EX36 | ENSE00001934531 | 166,303,302-166,302,619 | INT36 | Intron ENSE00003545902-ENSE00003645381 | 166,305,791-166,304,330 |
| EX37 | ENSE00002257282 | 166,375,987-166,375,697 | INT37 | Intron ENSE00003645381-ENSE00001934531 | 166,304,237-166,303,303 |
| EX38 | ENSE00002232442 | 166,199,864-166,195,194 | INT38 | Intron ENSE00002257282-ENSE00001584414 | 166,375,696-166,311,807 |
|  |  |  | INT39 | Intron ENSE00001128443-ENSE00002232442 | 166,203,954-166,199,865 |

Table 4 provides information on all of the transcripts for the SCN9A gene based on the Ensembl database. Provided in Table 4 are the transcript ID from Ensembl and corresponding NCBI RefSeq ID for the transcript, the translation ID from Ensembl and the corresponding NCBI RefSeq ID for the protein, the biotype of the transcript sequence as classified by Ensembl and the exons and introns in the transcript based on the information in Table 3.

TABLE 4

Transcript Information for SCN9A

| Transcript ID | Transcript NCBI RefSeq ID | Translation ID | Protein NCBI RefSeq ID | Sequence Biotype | Exon ID from Table 3 | Intron ID from Table 3 |
|---|---|---|---|---|---|---|
| ENST00000409672.5 | NM_002977 | ENSP00000386306 | NP_002968 | Protein coding | EX1, EX2, EX3, EX4, EX5, EX6, EX7, EX8, EX9, EX10, EX11, EX12, EX13, EX14, EX15, EX16, EX17, EX18, EX19, EX20, EX21, EX22, EX23, EX24, EX25, EX26, EX27 | INT1, INT2, INT3, INT4, INT5, INT6, INT7, INT8, INT9, INT10, INT11, INT12, INT13, INT14, INT15, INT16, INT17, INT18, INT19, INT20, INT21, INT22, INT23, INT24, INT25, INT26 |
| ENST00000303354.10 | — | ENSP00000304748 | — | Protein coding | EX2, EX3, EX4, EX5, EX6, EX7, EX8, EX9, EX10, EX11, EX13, EX14, EX15, EX16, EX17, EX18, EX19, EX20, EX21, EX22, EX23, EX24, EX25, EX26, EX31, EX37, EX38 | INT2, INT3, INT4, INT5, INT6, INT7, INT8, INT9, INT10, INT13, INT14, INT15, INT16, INT17, INT18, INT19, INT20, INT21, INT22, INT23, INT24, INT25, INT31, INT34, INT38, INT39 |
| ENST00000409435.5 | — | ENSP00000386330 | — | Protein coding | EX3, EX4, EX5, EX6, EX7, EX8, EX9, EX10, EX11, EX13, EX14, EX15, EX16, EX17, EX18, EX19, EX20, EX21, EX22, EX23, EX24, EX25, EX26, EX31, EX32, EX33 | INT3, INT4, INT5, INT6, INT7, INT8, INT9, INT10, INT13, INT14, INT15, INT16, INT17, INT18, INT19, INT20, INT21, INT22, INT23, INT24, INT25, INT31, INT33, INT34, INT35 |
| ENST00000452182.1 | — | ENSP00000393141 | — | Protein coding | EX5, EX7, EX8, EX9, EX10, EX11, EX28, EX29, EX30, EX31 | INT7, INT8, INT9, INT10, INT27, INT28, INT29, INT31, INT32 |

TABLE 4-continued

Transcript Information for SCN9A

| Transcript ID | Transcript NCBI RefSeq ID | Translation ID | Protein NCBI RefSeq ID | Sequence Biotype | Exon ID from Table 3 | Intron ID from Table 3 |
|---|---|---|---|---|---|---|
| ENST00000454569.5 | — | ENSP00000413212 | — | Protein coding | EX5, EX7, EX8, EX9, EX10, EX11, EX12, EX28, EX29, EX30 | INT7, INT8, INT9, INT10, INT11, INT27, INT28, INT29, INT30 |
| ENST00000472119.1 | — | — | — | Retained intron | EX34, EX35, EX36 | INT36, INT37 |

SCN9A has 3906 SNPs and the NCBI rs number and/or UniProt VAR number for this SCN9A gene are VAR_019947, VAR_019948, VAR_019949, VAR_019950, VAR_030444, VAR_032014, VAR_032015, VAR_032016, VAR_032017, VAR_032018, VAR_032019, VAR_032020, VAR_032021, VAR_032022, VAR_032023, VAR_064595, VAR_064596, VAR_064597, VAR_064598, VAR_071428908, VAR_064600, VAR_064601, VAR_064602, VAR_064603, VAR_064604, VAR_064605, VAR_064606, VAR_064607, VAR_064608, VAR_064609, VAR_064610, VAR_064611, VAR_064612, VAR_064613, VAR_072279, VAR_072280, VAR_072280, VAR_072281, rs951510, rs952462, rs952463, rs1011778, rs1358532, rs1406272, rs1540870, rs1540871, rs1540875, rs1919177, rs1881436, rs1881437, rs1881438, rs1881439, rs1997291, rs1528481, rs1528483, rs1528484, rs1528487, rs2893013, rs4131159, rs4131160, rs4131632, rs4488677, rs4408747, rs4331519, rs4429487, rs4001001, rs4273234, rs4583483, rs4438497, rs4286289, rs4546021, rs4455168, rs4455169, rs4605385, rs4465779, rs4384809, rs4386335, rs4667512, rs5836099, rs6432898, rs6432899, rs6432900, rs6432901, rs6432902, rs6432903, rs6432904, rs6432905, rs6432906, rs6432907, rs6432910, rs6723900, rs6720769, rs6715214, rs6712015, rs6712019, rs6708450, rs6708715, rs6725355, rs6725732, rs6722807, rs6716736, rs6723160, rs6726575, rs6760472, rs6723789, rs6728885, rs6738419, rs6729030, rs6732627, rs6719276, rs6729980, rs6738102, rs6750593, rs6756635, rs6718922, rs6718791, rs6757555, rs6731773, rs6715367, rs7577446, rs6715470, rs6757555, rs6731773, rs6715367, rs7577446, rs6732135, rs6714902, rs6757862, rs6746587, rs6721003, rs7558866, rs6432909, rs7584766, rs7589477, rs7584892, rs7559171, rs6432908, rs7590179, rs7572553, rs7566965, rs7602898, rs6432897, rs6432896, rs7580299, rs7603335, rs7597876, rs4667883, rs4667882, rs7582061, rs9287866, rs5836096, rs10171225, rs4564789, rs7594979, rs4459751, rs7606521, rs4599137, rs9646771, rs4076255, rs4447616, rs4443015, rs10188002, rs3956542, rs4132348, rs4132347, rs4131162, rs4131161, rs1528486, rs1528485, rs1881440, rs1609311, rs1540876, rs1540874, rs10930216, rs10930217, rs10930218, rs10930219, rs1540873, rs1540872, rs6728894, rs11280107, rs11686478, rs7424841, rs12105034, rs13000874, rs6734919, rs11674528, rs12692794, rs12692795, rs6753017, rs6744871, rs6736291, rs11340941, rs12478446, rs6757314, rs13004059, rs11693091, rs6757502, rs6737120, rs6732242, rs12463992, rs12612992, rs12464575, rs13417859, rs13395456, rs12615462, rs6746615, rs7420705, rs13027418, rs12616699, rs12467272, rs11898284, rs7589743, rs16851931, rs7597083, rs7597178, rs16851958, rs16851960, rs7598695, rs7592978, rs16851968, rs9759544, rs7606196, rs16852023, rs16852031, rs16852043, rs16852048, rs16852054, rs16852069, rs13030011, rs11899120, rs13013237, rs12469343, rs7606274, rs13401294, rs12992260, rs10190952, rs9646772, rs7608288, rs10193767, rs10538478, rs12994338, rs13016545, rs12994880, rs13405544, rs13034090, rs13017469, rs10556841, rs13017637, rs11888456, rs10600584, rs13035164, rs10611611, rs10634344, rs12473416, rs13431341, rs13020056, rs10638743, rs13021236, rs12999243, rs13000233, rs13000683, rs10655845, rs13387119, rs11435802, rs35244507, rs10688081, rs10696005, rs10710576, rs11463044, rs35280187, rs10497283, rs34327610, rs13390803, rs34920657, rs10497284, rs34355606, rs35730267, rs34926643, rs35333199, rs34936668, rs36101458, rs12476306, rs12105169, rs58078583, rs12692796, rs58159440, rs41268677, rs11890824, rs58184464, rs35789805, rs56058874, rs35353363, rs34490209, rs35821032, rs35360495, rs34449821, rs35425598, rs56999748, rs11681893, rs35473199, rs11682860, rs11676630, rs11693152, rs13004690, rs12615972, rs34617014, rs13026637, rs56149857, rs16851928, rs35911982, rs16851935, rs16851943, rs55681559, rs16851964, rs16851966, rs35542360, rs16851974, rs16852010, rs11885693, rs17766038, rs17766243, rs17766561, rs17766807, rs11901118, rs13426370, rs57275972, rs12993435, rs13427940, rs12472033, rs12622435, rs12622743, rs35187227, rs13035599, rs36035794, rs12996068, rs13021074, rs34784693, rs60461278, rs59265133, rs56282252, rs36096260, rs59348143, rs56292816, rs16826112, rs35257630, rs34813283, rs55945526, rs13411967, rs60930703, rs67175205, rs73025509, rs73025522, rs73025523, rs73025528, rs28532836, rs73025590, rs35683510, rs13391197, rs62176964, rs62176965, rs55989063, rs62178525, rs35433129, rs33999505, rs34533574, rs71428911, rs71428912, rs71428915, rs71428916, rs71428917, rs71428918, rs71428919, rs60050530, rs71428910, rs34038642, rs72149794, rs35077026, rs35080467, rs34582751, rs57073619, rs57087440, rs34082367, rs73972306, rs73972316, rs73972318, rs74336612, rs75477543, rs56152529, rs76673713, rs71031239, rs34099849, rs34101964, rs35129718, rs76710665, rs76711511, rs79030107, rs74445522, rs79031716, rs74449889, rs75597232, rs76740831, rs75608447, rs34132334, rs34649195, rs35552412, rs77937563, rs72882854, rs72882859, rs72882882, rs72882899, rs72882901, rs72884703, rs17766014, rs17766982, rs72884732, rs72884741, rs72884745, rs72884753, rs72884762, rs72884775, rs72884780, rs72884785, rs72884786, rs35962214, rs72884797, rs72884798, rs17817307, rs72884802, rs75675344, rs72886606, rs72886608, rs17817547, rs79140856, rs79147031, rs17817679, rs80356466, rs35182375, rs80356469, rs35595054, rs55754250, rs75773428, rs60310134, rs60392208, rs36073771, rs71395218, rs115848509, rs66472972, rs79202357, rs75794168, rs57861261, rs71405933, rs73025538, rs112373468, rs62176960, rs75818857, rs62176961, rs67339035, rs62178526, rs115911128, rs75848558, rs60056351, rs71428914, rs115946138, rs74706664, rs113603623, rs111285706, rs111302354, rs77046324, rs60145586, rs113610968, rs72330491, rs112490413, rs73969684, rs112504933, rs111337704, rs74757084, rs116013127, rs73969685, rs74768783, rs73969700, rs116037918, rs73969701, rs72520704, rs74385849, rs71031240, rs79417925, rs74791755, rs71031242, rs74423851, rs75620229, rs79061212, rs75645300, rs113739900, rs72884720, rs113758466, rs72884726, rs72884789, rs72884800, rs78215125, rs75709114, rs77151034, rs77154470, rs111426485, rs80356465, rs80356468, rs114760918, rs80356470, rs114985967, rs79187718, rs74613934, rs112644902, rs76904702, rs111528010, rs78278362, rs115847294, rs112347596, rs115028579, rs113518536, rs78304745, rs79221441, rs79222523, rs112718465, rs115074698, rs113962992, rs111624869, rs75818591, rs115099720, rs74658674, rs75006765, rs115881388, rs113988866, rs114811473, rs111281728, rs111679051, rs75029843, rs112761603, rs78428931, rs112768548, rs113629537, rs111705022, rs111705421, rs75053746, rs78118515, rs79645790, rs115979359, rs113660887, rs114893976, rs78162977, rs114048544, rs115193623, rs75093813, rs78510947, rs77373314, rs76244722, rs112835924, rs76247525, rs113698317, rs78552930, rs74778123, rs116048770, rs116373723, rs75949647, rs114920745, rs116069340, rs112869318, rs114923155, rs114926041, rs115322950, rs113737673, rs112561342, rs77143068, rs79446427, rs111404258, rs112919255, rs111415017, rs75225428, rs111458233, rs112945476, rs111470787, rs79493055, rs116451742, rs111899000, rs77487847, rs113850984, rs77192374, rs76448913, rs78250271, rs116188445, rs112675405, rs111948101, rs111953170, rs77231154, rs114267271, rs115435826, rs79853207, rs77579497, rs113911089, rs78334485, rs79876905, rs76510000, rs76102017, rs116547783, rs115473061, rs111643968, rs115489522, rs77639503, rs116268225, rs111654843, rs113989468, rs114344033, rs77682648, rs115119378, rs77328118, rs112779076, rs78452939, rs113173376, rs76571042, rs115522370, rs114032727, rs78863850, rs113195803, rs78454756, rs116653005, rs77784194, rs77797040, rs78906046, rs75468572, rs80095598, rs138982989, rs138989210, rs114358903, rs113283978, rs113182934, rs114525222, rs115555277, rs75069209, rs79684957, rs115244856, rs113309940, rs113311364, rs80160529, rs115251943, rs115274753, rs112867239, rs114118902, rs139080215, rs114143095, rs116773598, rs148713442, rs142480223, rs77432282, rs140701967, rs148765803, rs145478117, rs79741845, rs142518463, rs139170417, rs77441037, rs75200610, rs148846057, rs145575900, rs116422705, rs111858722, rs116435828, rs116962683, rs75230883, rs148931877, rs112947029, rs121908920, rs121908921, rs140792426, rs115783892, rs113436493, rs111884740, rs139281380, rs139288692, rs112970706, rs115393048, rs112995109, rs75273355, rs77539813, rs115812636, rs142707672, rs78731163, rs184266839, rs140830160, rs111972606, rs149102734, rs78763917, rs116547537, rs114319629, rs145811912, rs184317901, rs77642761, rs149157378, rs115495114, rs79918973, rs142779717, rs149194222, rs112047115, rs181405366, rs76564908, rs78843438, rs181423521, rs184404793, rs80126387, rs149285180, rs137950241, rs184447464, rs149297295, rs78947176, rs117581394, rs187270227, rs139017042, rs116710246, rs149301325, rs142909834, rs140574148, rs137962506, rs190380742, rs137966449, rs116713443, rs149350025, rs112222195, rs184515932, rs116748713, rs142952951, rs139064023, rs181563231, rs181572301, rs181577442, rs78998616, rs145366755, rs113361139, rs115726491, rs184560681, rs184561606, rs148819190, rs190457189, rs142559100, rs149429956, rs143007711, rs142585699, rs114681048, rs140761356, rs145608272, rs121908916, rs142666506, rs187410330, rs115802383, rs187428818, rs149490896, rs149507189, rs113450348, rs149034908, rs146213117, rs145737444, rs184675901, rs146234445, rs181717210, rs184685668, rs181276399, rs187500785, rs145769973, rs190597640, rs181734340, rs184275120, rs143161505, rs146267489, rs149592596, rs190625704, rs115823295, rs141042794, rs138081618, rs190666356, rs190668591, rs184760546, rs149648597, rs145798468, rs184289118, rs142753783, rs187145433, rs181814822, rs146333890, rs187164514, rs187187436, rs181818571, rs181414054, rs184784994, rs181414423, rs181840211, rs187627632, rs145969336, rs187630476, rs187638933, rs181864169, rs117600380, rs143281561, rs149739106, rs187660096, rs184471275, rs139433712, rs143307775, rs187686954, rs143323637, rs146453073, rs184491945, rs184503606, rs149812467, rs187735078, rs181543382, rs187739615, rs149846122, rs181976860, rs181544216, rs184525265, rs187760599, rs190446880, rs137993592, rs184557454, rs182005122, rs184956974, rs184558307, rs184973913, rs184975345, rs190455017, rs146114242, rs182041228, rs149440243, rs190971448, rs139677117, rs138238059, rs143020225, rs187396655, rs149989224, rs191004585, rs187404611, rs150021077, rs146148893, rs182164896, rs182169962, rs149458240, rs187420437, rs187457184, rs141218614, rs146210131, rs146758972, rs185134458, rs187483230, rs187499307, rs138051487, rs139537793, rs190630868, rs150115235, rs149656478, rs191129855, rs187982120, rs182221863, rs184769972, rs181809487, rs141258921, rs146330125, rs184777485, rs139562000, rs188023656, rs150184169, rs139564447, rs191220059, rs146882468, rs184798240, rs187628994, rs143699917, rs143713899, rs184829398, rs143292594, rs188117229, rs143733438, rs141345692, rs188123311, rs188145250, rs146953750, rs141083667, rs143769263, rs181942663, rs146963548, rs149811195, rs190856490, rs191334405, rs190873215, rs191343221, rs139815430, rs181981693, rs191359321, rs149865252, rs150371036, rs143829355, rs191372613, rs138452077, rs138452908, rs185386849, rs143842609, rs188237643, rs150393847, rs187773100, rs187775085, rs184966574, rs184977393, rs191427726, rs188275827, rs182035257, rs184996404, rs141453198, rs188284141, rs190995816, rs138488726, rs139848912, rs182512669, rs191445085, rs146642805, rs191006637, rs182521362, rs188309132, rs150023650, rs191085791, rs185460522, rs185466137, rs182175100, rs191091185, rs191109954, rs185493398, rs146761679, rs182203285, rs185502977, rs150107947, rs191122461, rs139722857, rs141521157, rs185512688, rs188369589, rs191126523, rs139884364, rs139732025, rs143623645, rs138334413, rs185538321, rs182251259, rs138341036, rs182626281, rs191206839, rs182313512, rs141315817, rs147236226, rs144030757, rs141338230, rs182655507, rs191614297, rs150639101, rs143731425, rs188153399, rs144066296, rs141603539, rs150324876, rs141375532, rs185622259, rs191640401, rs146970406, rs188513575, rs141629021, rs150341781, rs191351429, rs141401072, rs188532495, rs188248808, rs147057677, rs188544520, rs191692191, rs144131152, rs147074129, rs182496397, rs191429109, rs182500442, rs141673661, rs139846473, rs150446261, rs150785198, rs182820808, rs182520122, rs182835951, rs182529061, rs188657481, rs182852687, rs138621998, rs182529589, rs185798678, rs150473901, rs141757967, rs182553426, rs185815125, rs143943780, rs185496131, rs150902480, rs185498433, rs191884045, rs185502994, rs185503388, rs188365371, rs188776686, rs185517165, rs141530060, rs188383084, rs191914888, rs191918328, rs191918870, rs150560390, rs191920350, rs144365987, rs144372216, rs191935835, rs188403481, rs188811649, rs185898649, rs147221067, rs182626458, rs150991753, rs144016113, rs191958942, rs150590478, rs183013605, rs182641899, rs183026897, rs139927718, rs144435180, rs144435267, rs140119151, rs188473580, rs147697530, rs139930314, rs151064878, rs150652684, rs185979948, rs185640009, rs140151023, rs188519035, rs183095706, rs188522328, rs150690124, rs191679645, rs183115017, rs183125824, rs183133746, rs186044551, rs141940569, rs151168288, rs138746989, rs191681855, rs144136503, rs150725477, rs191708188, rs191711647, rs182806094, rs144573884, rs147831105, rs147833108, rs147430160, rs185756419, rs188657198, rs141742493, rs144270467, rs138636241, rs186110761, rs186125436, rs151258913, rs150885548, rs192222550, rs192233893, rs147939855, rs183284329, rs147539362, rs185839773, rs188756672, rs138823585, rs188769302, rs140057840, rs183353183, rs188780390, rs183367774, rs188784746, rs185874593, rs188790411, rs192366053, rs188810319, rs188814235, rs189287946, rs182991290, rs144392389, rs147640034, rs151008517, rs192402484, rs183036253, rs138700080, rs138700579, rs183064984, rs185993526, rs189320567, rs183090065, rs192417863, rs142157838, rs180836507, rs186006161, rs148149379, rs144500679, rs151120735, rs180884797, rs180886733, rs186060853, rs144552092, rs189017951, rs189022051, rs186460536, rs140492487, rs186461495, rs189023255, rs186466472, rs141954437, rs189522976, rs189523541, rs189049999, rs148313223, rs151210240, rs189054543, rs147849719, rs189539871, rs189064184, rs189068219, rs192210846, rs147956569, rs186209759, rs189569164, rs192674981, rs144747253, rs186238424, rs183351491, rs183367424, rs192699758, rs183370069, rs189262728, rs192363212, rs183403867, rs192726587, rs142134626, rs183711149, rs142138406, rs181081805, rs192738555, rs142140153, rs200131264, rs140380560, rs181094108, rs200134765, rs144841509, rs183732115, rs192406551, rs142150794, rs148096531, rs200162971, rs186321392, rs370110583, rs148456006, rs192433693, rs186364672, rs186633344, rs180802944, rs200178927, rs200194515, rs375200578, rs200182914, rs145193907, rs183502133, rs140445008, rs180893354, rs138915544, rs145244774, rs148241180, rs186442256, rs200240989, rs186465363, rs148278257, rs145257168, rs189524843, rs148315085, rs183628282, rs189533865, rs183640056, rs148556202, rs200292819, rs192655074, rs192658579, rs189564784, rs138962140, rs148362057, rs142347131, rs189586446, rs200341902, rs200063079, rs370018897, rs200099565, rs192906198, rs183704773, rs192723631, rs181075520, rs186767700, rs181079869, rs370059723, rs186771296, rs529190860, rs370067909, rs529209086, rs186784826, rs200394559, rs200399998, rs183730817, rs538838362, rs370082676, rs200408344, rs142400656, rs200411606, rs145182185, rs145187060, rs186806270, rs200172456, rs192975309, rs375204316, rs370455867, rs200449501, rs186648437, rs534019932, rs529286738, rs375210239, rs370472054, rs192801395, rs370474533, rs186654635, rs200213811, rs186674692, rs538940239, rs375250531, rs200482081, rs375566600, rs181175263, rs200486515, rs370211696, rs181183562, rs181186118, rs193052322, rs200518320, rs200258203, rs186875141, rs181200412, rs375314088, rs184015802, rs375635737, rs186886737, rs529393841, rs375684756, rs539081952, rs200296022, rs189773617, rs375344768, rs375717078, rs189783847, rs193147774, rs189793333, rs189802138, rs375383262, rs200341995, rs148603098, rs370331208, rs183883370, rs190038995, rs190041054, rs200356611, rs192916635, rs148622242, rs539165024, rs534237861, rs189833651, rs200381002, rs539201442, rs529545926, rs190079309, rs529224329, rs538840251, rs200677133, rs538845547, rs370750101, rs534286923, rs375828071, rs200417967, rs539238807, rs184127871, rs375484262, rs190100237, rs200702592, rs538865759, rs200441726, rs370458490, rs375873835, rs370471482, rs370474188, rs534038802, rs534350762, rs534357040, rs200464271, rs184169321, rs193007084, rs529641451, rs529320212, rs375570049, rs529339341, rs538978492, rs193043836, rs200774110, rs189961043, rs200780217, rs534113220, rs370879581, rs534409097, rs534414126, rs534415144, rs370562444, rs200579922, rs199528742, rs200815709, rs534171106, rs539098927, rs539117115, rs200830395, rs186937907, rs370939400, rs539140140, rs200617539, rs200619065, rs184228905, rs200835066, rs376036522, rs539143083, rs200849406, rs539479843, rs376051261, rs529755984, rs534486080, rs534488673, rs193152357, rs375749001, rs375763051, rs193166864, rs539520802, rs529783271, rs200878465, rs534232221, rs375776919, rs200884318, rs190061595, rs534278901, rs190082049, rs545837483, rs375825189, rs187135957, rs375828938, rs193224590, rs376111502, rs553880123, rs193232467, rs375856563, rs553890257, rs534545311, rs200709311, rs539583140, rs200720228, rs199625995, rs539285858, rs375886661, rs539314440, rs529638862, rs200757990, rs193290821, rs200764978, rs370859545, rs193298128, rs190162179, rs529872397, rs554016514, rs370874132, rs539661794, rs375980172, rs200809157, rs545964402, rs539677853, rs200826539, rs200972952, rs554071139, rs534656457, rs529727269, rs184226889, rs554100480, rs376022705, rs200831251, rs200999865, rs201000497, rs529730407, rs200843960, rs184246546, rs190358218, rs554163756, rs554165274, rs199576878, rs539500156, rs376288233, rs199589622, rs184260785, rs371207844, rs200882280, rs199599557, rs199756028, rs529983093, rs200885240, rs187133567, rs563464573, rs201061055, rs539547053, rs554273987, rs529802379, rs199609865, rs553889410, rs546154866, rs553889944, rs534551405, rs553911796, rs371042731, rs554309833, rs554312712, rs199784484, rs201087484, rs371264016, rs199791955, rs563543796, rs554341821, rs546194264, rs371271639, rs545893207, rs539907191, rs546211175, rs539907650, rs554376047, rs534785673, rs200925482, rs201111027, rs546225573, rs190283527, rs553954986, rs199824489, rs200939963, rs199828294, rs539633485, rs534590465, rs530084774, rs199836776, rs553992440, rs200946565, rs376437229, rs534834256, rs545955340, rs529878459, rs534839750, rs539669267, rs563692075, rs546307681, rs199679924, rs554081720, rs534850887, rs554088921, rs540043962, rs554092522, rs190336684, rs199879584, rs530137975, rs200995410, rs530143022, rs371164212, rs190349718, rs546362979, rs199717009, rs371397880, rs540082625, rs201198963, rs201021546, rs563799556, rs199737519, rs371414170, rs554199061, rs199746311, rs546391192, rs190379146, rs199753578, rs201051190, rs199757256, rs199915769, rs546428044, rs554663323, rs199924841, rs540148616, rs563477777, rs199933920, rs546146748, rs563898086, rs201243874, rs546456054, rs199940586, rs530215503, rs563913729, rs530218681, rs376579866, rs199948709, rs540192719, rs540198060, rs554750370, rs563492226, rs554287627, rs546498422, rs546158464, rs540216332, rs554299241, rs199968973, rs546516362, rs563983733, rs199780289, rs199780984, rs371286659, rs371523166, rs530267604, rs199987389, rs540258346, rs534786295, rs546227682, rs535009588, rs371537833, rs546570808, rs546572548, rs534792758, rs554861011, rs530289862, rs539955067, rs199832245, rs199832681, rs199841742, rs554463637, rs535055981, rs564125461, rs200028908, rs546625033, rs199848155, rs376692400, rs564139470, rs199850424, rs201155458, rs554499889, rs535082824, rs554501599, rs371367087, rs563737735, rs200056934, rs564203583, rs546340639, rs371630270, rs540400302, rs376746720, rs201185327, rs546352773, rs575423992, rs376493135, rs546717270, rs371397187, rs540431428, rs534892966, rs201205411, rs199903431, rs376515297, rs563817371, rs563824187, rs546746556, rs555098627, rs575492002, rs201217172, rs376529993, rs554686400, rs546760948, rs534939379, rs563953797, rs540206408, rs546500427, rs540485824, rs376608116, rs554799633, rs540505612, rs201445594, rs546799753, rs540240449, rs534999520, rs540519101, rs564030716, rs376835362, rs530454237, rs564030746, rs199998975, rs200004737, rs564394299, rs540551673, rs575674513, rs564399141, rs564446433, rs200011236, rs575695879, rs530483113, rs530485751, rs575707171, rs564466723, rs376885423, rs535039496, rs546880794, rs371565974, rs546882633, rs371773562, rs535234661, rs540598706, rs564107843, rs201343843, rs201354058, rs201503351, rs530342843, rs546907614, rs376908183, rs201510411, rs554978785, rs201511761, rs200048101, rs546921591, rs530350892, rs376922975, rs564200680, rs200060978, rs201533181, rs575403459, rs564241971, rs564580989, rs546961299, rs201544671, rs201545926, rs371836327, rs540688834, rs201398365, rs575434258, rs564263518, rs564274418, rs376775745, rs575466805, rs555444508, rs201414746, rs546745027, rs564310081, rs376792891, rs564315036, rs547017479, rs530416775, rs564331757, rs547021107, rs564332268, rs564662103, rs540733381, rs555135086, rs555471824, rs576009530, rs530597787, rs576019908, rs555139503, rs201589695, rs546790645, rs576055160, rs564376709, rs564714000, rs201599943, rs530619739, rs547065965, rs575600523, rs540522467, rs540547244, rs547082685, rs564445595, rs540567098, rs540796514, rs371731981, rs564769026, rs546879622, rs377073478, rs540589456, rs555621992, rs371916205, rs371958712, rs530634413, rs575756239, rs376897349, rs371780831, rs376904842, rs535249716, rs575804340, rs555336411, rs540652005, rs530685640, rs376937738, rs555659985, rs201659566, rs530547787, rs575882807, rs201664439, rs564870320, rs376965890, rs564871823, rs546993077, rs575943952, rs201560701, rs540907392, rs564896638, rs564896690, rs547000677, rs564899870, rs201563763, rs576373898, rs564640008, rs555445641, rs575973973, rs372028184, rs371863491, rs555773796, rs564960625, rs547253736, rs576455029, rs540974086, rs564986496, rs564993510, rs201726729, rs371864190, rs565010528, rs540730019, rs201574893, rs376994924, rs530783315, rs201577842, rs201741634, rs201743233, rs547309884, rs371884028, rs372088334, rs377222716, rs576572380, rs576041557, rs547054615, rs201761066, rs377231210, rs576600072, rs576089157, rs530626933, rs541061398, rs530815395, rs576098220, rs565110303, rs540810897, rs555612139, rs541084553, rs576662260, rs547128261, rs540853945, rs555633602, rs377085474, rs547403854, rs565167501, rs530849811, rs576712624, rs547415198, rs201649913, rs201651716, rs377093160, rs535596388, rs576773731, rs576676610, rs535558092, rs565234556, rs377328308, rs555955176, rs565256471, rs556091995, rs372131207, rs201845924, rs555645605, rs541215463, rs564833136, rs565311283, rs565318120, rs540868515, rs576946641, rs556156424, rs547539536, rs201883775, rs535414368, rs372262107, rs530959005, rs540871938, rs577021824, rs535419397, rs201895529, rs540879571, rs372269123, rs377116511, rs547186293, rs565405762, rs547588654, rs201905108, rs556236282, rs201905758, rs547191791, rs540903705, rs547201834, rs530979178, rs372002155, rs576377214, rs555741423, rs577086434, rs201915876, rs530989045, rs540941092, rs556278477, rs535735811, rs201707595, rs576479846, rs541356065, rs541358959, rs535499788, rs541362812, rs565031158, rs535511711, rs577214491, rs372339994, rs377206205, rs576544612, rs377226193, rs576585621, rs541054278, rs577266682, rs565097315, rs565571242, rs577289107, rs556405965, rs576629767, rs535795174, rs530825627, rs565155125, rs565186443, rs201992546, rs541131401, rs377540035, rs377540898, rs541131406, rs565224250, rs201821518, rs541464325, rs577369845, rs565254553, rs577404457, rs372203675, rs565602281, rs202014643, rs576881042, rs577440102, rs547742253, rs577443766, rs531116715, rs377543079, rs565709853, rs201999985, rs377592540, rs541216093, rs201867764, rs565371438, rs372263773, rs547573283, rs201896555, rs535696383, rs201899627, rs530977363, rs577068583, rs201908866, rs547600407, rs547600820, rs535712483, rs556270749, rs541350117, rs577567218, rs577154533, rs565779439, rs541577543, rs577175836, rs531022872, rs565800474, rs565519424, rs541591158, rs547675018, rs541594618, rs565809092, rs372495273, rs541395767, rs202083986, rs556650900, rs565547663, rs577251799, rs556665730, rs556373614, rs531050542, rs565585913, rs531203453, rs565871418, rs535797353, rs202109432, rs577720248, rs201987450, rs531083937, rs577393911, rs531100303, rs556716582, rs577747466, rs556487424, rs372559804, rs556713829, rs531103846, rs565682322, rs372563835, rs577815172, rs377588911, rs565947211, rs547813798, rs531250791, rs556789899, rs531125112, rs541713728, rs556819410, rs377754745, rs556713324, rs547819277, rs536000213, rs377597385, rs202165845, rs556543920, rs535860380, rs556549617, rs577508369, rs556552102, rs548057554, rs565736915, rs202180059, rs556878947, rs547836679, rs202051580, rs577538470, rs577539276, rs531148427, rs556584085, rs531302114, rs202061011, rs535883810, rs556612694, rs531317317, rs202071016, rs372490157, rs372654175, rs556940143, rs372655989, rs541594525, rs578059299, rs541831570, rs577625085, rs547898574, rs372511122, rs202219028, rs531188532, rs547913013, rs541630786, rs547938227, rs578134604, rs541870309, rs556706372, rs202110802, rs372557663, rs547975937, rs566204756, rs566207903, rs577796497, rs556764057, rs557048933, rs202241586, rs531379120, rs557050535, rs541923828, rs556774205, rs578243189, rs541702079, rs535980549, rs531270141, rs535997775, rs566269762, rs556841303, rs557109946, rs745311902, rs548256739, rs556848020, rs548043362, rs536155895, rs566022284, rs577936356, rs541985091, rs548053319, rs556871781, rs536168223, rs566049151, rs577967498, rs566340038, rs386391721, rs386391722, rs557188530, rs367584747, rs386391723, rs566366442, rs536028182, rs542030965, rs578005069, rs566085715, rs566086387, rs578024455, rs367621683, rs548346140, rs372833423, rs548105826, rs202211195, rs745531940, rs202215137, rs578072210, rs372665054, rs531338785, rs536243045, rs566133697, rs578090160, rs367666265, rs578114636, rs548158077, rs566180671, rs397765197, rs536089884, rs557356456, rs397767714, rs367683945, rs566528668, rs745659906, rs267598976, rs557071588, rs267598977, rs367701477, rs566564807, rs536281976, rs578242489, rs566583346, rs548214486, rs548476797, rs536129992, rs548482202, rs566262563, rs566594213, rs267607030, rs372744611, rs557461504, rs745754029, rs566617243, rs566617297, rs548258391, rs566310144, rs548519839, rs745338187, rs536158076, rs548274093, rs745823712, rs536163412, rs397868358, rs548542674, rs536168659, rs745839147, rs566338405, rs566348964, rs557535791, rs548558816, rs548565032, rs745383244, rs397870091, rs548565940, rs542287393, rs566709971, rs372990045, rs557204387, rs745418676, rs566409045, rs566730224, rs566752170, rs566753733, rs372818817, rs397722222, rs745983399, rs367830408, rs745480989, rs566793485, rs397734324, rs548645786, rs557669888, rs745516750, rs548657650, rs548381702, rs745552432, rs536425753, rs397973279, rs746070730, rs548387911, rs557708733, rs372854250, rs745569838, rs548698515, rs566482323, rs557734401, rs746118213, rs542420738, rs367667669, rs397986566, rs566902157, rs531528009, rs548736753, rs566500747, rs542456172, rs746187360, rs367671512, rs566932278, rs745660727, rs367697326, rs548464529, rs531756169, rs542471936, rs566573122, rs566962886, rs542498214, rs566982218, rs542504451, rs557806739, rs398090827, rs746306232, rs536489917, rs531803128, rs745714010, rs367720972, rs557918693, rs746350953, rs745725339, rs367991453, rs527241020, rs531579666, rs746381295, rs542208653, rs397818828, rs746391927, rs557954773, rs531600512, rs566644132, rs548866946, rs536555587, rs566656331, rs372959324, rs548538509, rs567102431, rs745838757, rs397868838, rs746437505, rs397868962, rs548885146, rs531845059, rs536570765, rs372983721, rs557571631, rs566719571, rs536584686, rs566723075, rs542325703, rs542643487, rs368055368, rs373019820, rs567192923, rs548936551, rs542349880, rs558065104, rs542355012, rs368062692, rs536415135, rs397963856, rs746552388, rs557690548, rs542394071, rs746083843, rs548693261, rs557732835, rs746143575, rs542699414, rs558122779, rs567298923, rs536465674, rs558134318, rs531746406, rs527346644, rs548743673, rs368107300, rs367917548, rs746198188, rs557871766, rs567022998, rs567363028, rs373168195, rs567043047, rs567054046, rs558207456, rs542763237, rs746378441, rs536545503, rs542568822, rs548865256, rs368147111, rs542580556, rs558228752, rs536555646, rs746772302, rs536557590, rs531975462, rs746796860, rs527408032, rs746420496, rs536564089, rs368176642, rs558272974, rs746431232, rs531844054, rs527275962, rs746843910, rs567526414, rs542614723, rs549120414, rs549124141, rs536578689, rs549140206, rs567586614, rs536744845, rs558044120, rs746516190, rs558055629, rs746920567, rs558060550, rs368061706, rs527461217, rs567208316, rs531886773, rs746554596, rs567220976, rs542895321, rs746974389, rs567222661, rs549185419, rs567237436, rs527336026, rs527483460, rs558121403, rs548993925, rs567691347, rs747002615, rs548995543, rs746650412, rs368271911, rs567723777, rs747040934, rs747050192, rs746670993, rs567347819, rs527512680, rs531938194, rs549242146, rs549032856, rs567373871, rs567394422, rs368307024, rs542980503, rs558508221, rs536676061, rs536681562, rs558516052, rs549052565, rs368145556, rs532090630, rs527554992, rs532120905, rs558490145, rs747176695, rs542991566, rs542774236, rs368150079, rs373340022, rs558242385, rs549357789, rs531980410, rs368389084, rs746808580, rs549368350, rs567506427, rs531991551, rs536910845, rs549105394, rs746848184, rs373384143, rs549407905, rs558344252, rs527453833, rs549417854, rs746919102, rs746928276, rs527655882, rs368229380, rs558364672, rs549168229, rs368463219, rs568161057, rs558762757, rs532232329, rs549168547, rs747470520, rs549464271, rs543190810, rs543192154, rs368241422, rs536968067, rs747507965, rs558804203, rs542903509, rs747524681, rs567666371, rs558400652, rs549194158, rs527487277, rs368267915, rs536991033, rs568290255, rs558428181, rs567744716, rs527721202, rs568321346, rs568324171, rs568330046, rs567746937, rs568347691, rs747644321, rs747646048, rs567759326, rs747078793, rs536831479, rs568368464, rs558924666, rs543302057, rs543307320, rs747708818, rs558953446, rs568439076, rs532106809, rs558517679, rs558548847, rs747224561, rs568476272, rs567841142, rs549626904, rs373748468, rs747772882, rs747777569, rs559008851, rs549332923, rs373735201, rs747760347, rs568467648, rs568540915, rs568478645, rs568552353, rs368374445, rs747265095, rs567978316, rs559065366, rs527824027, rs537109464, rs747287657, rs747918167, rs536895056, rs373815330, rs536905377, rs537128261, rs558672062, rs568679804, rs537140055, rs747362082, rs543122161, rs558701088, rs747382624, rs373841126, rs532429751, rs568724063, rs543132278, rs747426187, rs543154656, rs373616597, rs747448727, rs558755199, rs543176875, rs558793028, rs549483878, rs559205579, rs549801876, rs748064481, rs549805500, rs568786830, rs368724653, rs368741155, rs558812967, rs373650798, rs558827971, rs527935102, rs549505744, rs532266308, rs568910791, rs543588977, rs568921105, rs543252094, rs568938831, rs568308434, rs748230779, rs558889724, rs543276363, rs532518466, rs549553842, rs558900091, rs568478922, rs373953968, rs549933491, rs559388880, rs569021337, rs748301976, rs527792590, rs748304870, rs537274423, rs527797934, rs549957716, rs559020013, rs747831682, rs747839515, rs537094901, rs568565984, rs549993366, rs373786499, rs568616456, rs528024377, rs569138531, rs373808223, rs748419478, rs568648416, rs747947163, rs543458934, rs527866121, rs748000776, rs748452908, rs543474534, rs559511141, rs532596683, rs528051938, rs748032198, rs559524225, rs559189600, rs748504526, rs537164960, rs569247301, rs748039029, rs549789421, rs559564579, rs543501994, rs748048145, rs748564719, rs368926174, rs532635443, rs373862049, rs559205490, rs532651681, rs368949323, rs374099497, rs543549351, rs537201581, rs550141100, rs537202219, rs532674344, rs543574164, rs748190208, rs559321177, rs559677369, rs569424535, rs748690640, rs748695381, rs527959809, rs748236906, rs537243887, rs568970879, rs559373028, rs373953011, rs569027161, rs543882002, rs559723934, rs549952543, rs528001989, rs748754609, rs569502538, rs532712684, rs374154008, rs369022060, rs569525422, rs543668808, rs550218083, rs369031999, rs532562751, rs537295453, rs543930117, rs537468875, rs550244319, rs569098216, rs550247150, rs569123332, rs748398622, rs569610503, rs569138600, rs559826745, rs559831361, rs537315654, rs374011315, rs569152152, rs559871284, rs550298627, rs550018415, rs374021078, rs748455811, rs369107141, rs569197685, rs569789352, rs544062895, rs550041205, rs749055063, rs544064839, rs569814685, rs532613900, rs537352949, rs550065962, rs569844606, rs559995442, rs569277903, rs550412301, rs569291008, rs368934346, rs569896484, rs550421090, rs748602707, rs374102129, rs560036890, rs528121884, rs537409772, rs569406301, rs749187435, rs560050695, rs374116302, rs749215366, rs560073328, rs749217434, rs569413716, rs569435862, rs537425379, rs559701154, rs550504055, rs537429508, rs537648288, rs528365663, rs748720721, rs559707544, rs748725716, rs570053547, rs748745862, rs528373215, rs537657709, rs749311576, rs569486858, rs544215781, rs374387803, rs748789887, rs369261656, rs544222244, rs559774900, rs369037062, rs528392678, rs569589072, rs569594721, rs537484448, rs560194858, rs532943697, rs528207220, rs550610763, rs570175462, rs543970760, rs532756083, rs749422762, rs537706167, rs550630579, rs528430659, rs569673848, rs570223084, rs544008440, rs748956951, rs532972999, rs560270291, rs749479220, rs560277925, rs559882854, rs749000031, rs544323417, rs570287651, rs749525560, rs528461391, rs537558317, rs749079120, rs374481593, rs550724860, rs560344389, rs559975872, rs374497861, rs569835399, rs749602473, rs749608721, rs570379112, rs749616223, rs570383918, rs560388069, rs550404028, rs550788771, rs532851603, rs532852070, rs528314905, rs570419018, rs528315588, rs374522881, rs569919976, rs550435904, rs570456628, rs569926252, rs550450442, rs749695781, rs749701713, rs374544338, rs528533074, rs537818590, rs570492575, rs570495057, rs544454714, rs374350913, rs570000771, rs570005998, rs570551342, rs369229821, rs749284610, rs570558380, rs528366547, rs550901951, rs550527209, rs570048995, rs550533340, rs570063206, rs369464511, rs528383682, rs374397762, rs550927757, rs550923680, rs560539816, rs533107673, rs374594002, rs369476119, rs749864558, rs570646108, rs550966261, rs749881351, rs749897918, rs550925375, rs544544030, rs544231457, rs560608042, rs560181527, rs544551194, rs369520775, rs533153225, rs528632986, rs749364100, rs544577577, rs369534920, rs570119696, rs570782066, rs528411030, rs550621249, rs551063575, rs750002442, rs750005785, rs528650251, rs369296369, rs560255202, rs374670592, rs551081825, rs570227654, rs570232101, rs550676640, rs560705198, rs551103406, rs570060579, rs570253110, rs570861231, rs551126930, rs560742915, rs532994198, rs537750141, rs528481236, rs374500828, rs528693904, rs544387925, rs528695618, rs544671979, rs749640667, rs528701463, rs570957540, rs528504065, rs528504422, rs560405294, rs570985462, rs560819326, rs560408978, rs533248873, rs544410928, rs570467358, rs571031386, rs544422821, rs571046788, rs550875084, rs544456517, rs533083149, rs528558257, rs570555980, rs749782980, rs571112937, rs533289922, rs560511642, rs533297953, rs528567800, rs544487770, rs750377110, rs369709511, rs750395605, rs560523856, rs570685646, rs560602815, rs533104605, rs571201597, rs369722062, rs538095397, rs537898453, rs560644731, rs533167279, rs560669576, rs551401679, rs369545306, rs561042263, rs551429062, rs750017693, rs369556343, rs551090369, rs538124443, rs750042378, rs537945859, rs374872804, rs571350458, rs561086455, rs571361273, rs570859811, rs570896555, rs570898206, rs544911099, rs561103484, rs750110593, rs544921736, rs528872305, rs571410824, rs571416933, rs369592808, rs528882230, rs551531848, rs551164285, rs528891024, rs533405417, rs750148529, rs571464240, rs750175883, rs551569090, rs560811710, rs544697883, rs571001720, rs544980017, rs571007860, rs551236739, rs551249244, rs528924602, rs571065554, rs528745212, rs750724319, rs538210953, rs528933846, rs571071311, rs750755032, rs528942614, rs538036504, rs538040234, rs544760124, rs560927301, rs544802212, rs538235148, rs528956488, rs551342807, rs533481144, rs369899370, rs551359194, rs369900308, rs750399158, rs538259887, rs528795367, rs750864433, rs750411662, rs533498494, rs560998810, rs571707506, rs561331700, rs375028919, rs545103329, rs571703952, rs544837618, rs528807734, rs551400406, rs571269005, rs544875089, rs529020508, rs533357560, rs750951154, rs551440261, rs750514774, rs544886311, rs551792787, rs561404804, rs571366310, rs528855590, rs751001567, rs375069289, rs533379792, rs571842712, rs533382711, rs561137186, rs571879284, rs750631806, rs529077450, rs561470191, rs750638359, rs529093387, rs551558117, rs551573774, rs551579214, rs571500446, rs561525428, rs545229175, rs751136819, rs551581886, rs750707641, rs571528077, rs755813688, rs561214522, rs572015044, rs571536730, rs369860008, rs528947505, rs551963416, rs538225517, rs545277826, rs533634090, rs561260903, rs571600152, rs369874176, rs571638665, rs552017588, rs571666279, rs571668997, rs369907063, rs769057914, rs552049341, rs769065818, rs751325083, rs561669214, rs552061128, rs572187861, rs756005334, rs538475444, rs756013985, rs545099670, rs552106230, rs545375585, rs572237867, rs561726025, rs769150127, rs529011948, rs538288286, rs571755014, rs571757393, rs538515826, rs545115612, rs533712836, rs545115642, rs750944314, rs529029702, rs571778387, rs529035618, rs552177570, rs571826748, rs751000526, rs369968332, rs571851662, rs545431594, rs561799159, rs561460464, rs571880265, rs769270578, rs533571445, rs571940318, rs756189754, rs545217019, rs571959447, rs751128080, rs538381958, rs755804903, rs751159961, rs751175785, rs572018867, rs756228072, rs751582483, rs561574977, rs561576248, rs572437382, rs755851030, rs561611663, rs552286628, rs545506688, rs768991354, rs769402083, rs769406063, rs572087546, rs538428981, rs769026589, rs755939083, rs572579811, rs769491361, rs561982435, rs769046166, rs751371429, rs572259896, rs545578378, rs756446498, rs751798524, rs572656276, rs756457749, rs769554090, rs538674345, rs751813574, rs552419780, rs756076130, rs552432031, rs769194199, rs533853260, rs572717577, rs769195919, rs572295505, rs533714676, rs538700995, rs545631150, rs538526606, rs572321690, rs572759437, rs538715990, rs562093903, rs552491193, rs552493086, rs751920813, rs572323525, rs552522135, rs769705492, rs751482341, rs572334430, rs751492391, rs545682563, rs751495665, rs538752299, rs545696456, rs538535248, rs572354221, rs751523153, rs545446264, rs572377516, rs533919054, rs572892333, rs769771450, rs769774967, rs572382379, rs572388571, rs756700849, rs756704425, rs769807240, rs769295468, rs572950216, rs562222303, rs751550702, rs752097894, rs769296900, rs572978709, rs572982359, rs561835001, rs552229556, rs552242552, rs533760063, rs552650520, rs752133481, rs561858372, rs756247571, rs769912734, rs756277853, rs545508686, rs561928325, rs572544925, rs561951163, rs756369671, rs752191138, rs769511874, rs751770785, rs769520412, rs756476767, rs545617350, rs573120275, rs552452362, rs552743787, rs552722759, rs573125010, rs572720574, rs752267943, rs572723257, rs562364859, rs769633498, rs752289745, rs770063371, rs756983343, rs552799307, rs756541837, rs756588238, rs752355486, rs770120624, rs572827353, rs751960880, rs552847137, rs573278742, rs769713298, rs752418228, rs573311661, rs533903238, rs552555197, rs562163326, rs573336871, rs770205263, rs562492571, rs552901035, rs573360915, rs770226861, rs552927404, rs752501530, rs752008244, rs756662298, rs752010591, rs752027589, rs562558634, rs573456983, rs769784952, rs752598240, rs572946713, rs756749599, rs756758706, rs752107556, rs769861427, rs562628042, rs573532135, rs752123654, rs573539819, rs752651234, rs757322465, rs545769534, rs757324658, rs573014318, rs752159218, rs752669367, rs545789688, rs562288190, rs573583431, rs752694131, rs553077185, rs752705175, rs562290070, rs573057895, rs756846139, rs752187308, rs757406912, rs573077799, rs552710847, rs757431594, rs573668899, rs553131814, rs562733566, rs562322012, rs573698013, rs770570377, rs769977143, rs752262387, rs752842135, rs553198489, rs562795927, rs573769337, rs752265531, rs770014639, rs757542280, rs573778414, rs573160530, rs573173020, rs756996519, rs757574398, rs573226807, rs573830638, rs573832648, rs770130183, rs770143495, rs770714259, rs752395219, rs757620158, rs562472371, rs757091887, rs757651862, rs573329574, rs552932842, rs757678036, rs562906731, rs573398771, rs573931855, rs757698701, rs573423419, rs757196334, rs573956248, rs562590653, rs770844073, rs753073195, rs757264923, rs770368521, rs562966673, rs553375250, rs572286231, rs562624182, rs553028786, rs562631637, rs553396451, rs757816346, rs752659859, rs770424435, rs753158893, rs753161012, rs553429432, rs757326234, rs562658586, rs757848676, rs563030100, rs757851276, rs770440360, rs553444080, rs562685659, rs770998439, rs757903328, rs752715463, rs753243305, rs574158047, rs753248999, rs573615359, rs771049218, rs553520048, rs574218458, rs574218497, rs770484072, rs770507859, rs757415695, rs573692993, rs771127117, rs753348681, rs770572267, rs574279980, rs573729847, rs553217886, rs752874223, rs574313437, rs770646119, rs753375127, rs553594673, rs753413529, rs563204921, rs563204956, rs573793230, rs553615720, rs770669377, rs752915464, rs752935458, rs771254688, rs563250976, rs752936829, rs573845641, rs758171359, rs553671701, rs757627939, rs770755089, rs770761836, rs573905888, rs758213818, rs574458879, rs758231448, rs770785487, rs563313026, rs758251421, rs758252419, rs573944942, rs753048798, rs771377765, rs563340232, rs553350853, rs758286245, rs562957866, rs553362365, rs757786023, rs574020661, rs753630953, rs562989702, rs574575080, rs753648561, rs753119257, rs753668162, rs753149666, rs563015753, rs753169837, rs553433381, rs770963601, rs574621082, rs753732662, rs758421005, rs574670231, rs757870156, rs771562041, rs574145206, rs574724729, rs757927255, rs553537463, rs771111770, rs574251637, rs553550103, rs563161459, rs758527549, rs574771040, rs753843081, rs553570026, rs771649415, rs574292008, rs771662229, rs574805977, rs574854330, rs771738593, rs563201986, rs758651382, rs574315059, rs758656020, rs574340577, rs758660161, rs771774637, rs758691949, rs758107372, rs754017346, rs771227297, rs563235099, rs553661695, rs754045274, rs563260674, rs754055297, rs563269397, rs553682936, rs574438316, rs771304275, rs758800428, rs753559306, rs771919739, rs753582578, rs754141945, rs575081551, rs563336388, rs575092590, rs753600502, rs575125159, rs771392468, rs563351273, rs758888190, rs563353671, rs758905037, rs771413333, rs553772622, rs574587211, rs753682189, rs758373659, rs772039702, rs772039784, rs772048626, rs754275081, rs771477905, rs753690596, rs553815137, rs575278958, rs574681748, rs575303100, rs771582810, rs758485743, rs759087854, rs575348590, rs753812341, rs759111100, rs772225059, rs758499442, rs754462186, rs754476252, rs574742878, rs754490813, rs772285262, rs753828829, rs574761563,
rs772336893, rs754543076, rs759290654, rs772395366, rs753849639, rs754638250, rs758555473, rs759384662, rs574887579, rs754694440, rs772505511, rs754710057, rs753978827, rs771768782, rs772542224, rs772565872, rs574947376, rs759493094, rs771816020, rs574962188, rs758720517, rs754046765, rs772538411, rs754056327, rs759582553, rs754072901, rs759604608, rs759618021, rs759618971, rs772713563, rs754073647, rs754934055, rs754977237, rs772800001, rs758784984, rs754113212, rs575064964, rs575092333, rs771950039, rs575127361, rs771984656, rs771998562, rs772005602, rs759809047, rs772905789, rs575158631, rs755129606, rs754241027, rs755139637, rs754241912, rs759868988, rs575188566, rs755204073, rs773012423, rs773015695, rs773030286, rs575222561, rs759000378, rs575270437, rs772133229, rs759054169, rs760019571, rs575323599, rs772196281, rs755344662, rs755345735, rs759150088, rs773161532, rs755360952, rs755361509, rs772283807, rs760088897, rs773197006, rs773259205, rs760189302, rs755471441, rs755501706, rs754512913, rs760244093, rs755553046, rs772335325, rs759300259, rs772449743, rs773425925, rs772489586, rs754719129, rs755653914, rs755666694, rs760410743, rs759482720, rs759520309, rs754870625, rs760471093, rs759523063, rs754822550, rs773686703, rs754840578, rs760600919, rs760603637, rs772672495, rs754892941, rs760523838, rs760451171, rs755736948, rs760557658, rs760816228, rs772714587, rs755000613, rs772804611, rs755017523, rs759736603, rs759736945, rs760912489, rs774006498, rs772843217, rs759766086, rs755067851, rs759784688, rs761013330, rs772909429, rs772930184, rs761116601, rs761152276, rs774249327, rs774251259, rs774274995, rs772944744, rs761216742, rs774309167, rs772964132, rs761267824, rs761373885, rs759949565, rs755275181, rs774519927, rs774522732, rs761441210, rs761463732, rs773084045, rs773099131, rs773104432, rs760030368, rs774666634, rs761564783, rs761565126, rs755324498, rs773159916, rs761601211, rs755370020, rs761671328, rs774795813, rs774799502, rs760228901, rs774812992, rs774858304, rs761769631, rs755586452, rs761781232, rs774899950, rs773396301, rs760333909, rs755619723, rs774976082, rs761920258, rs761927300, rs761950663, rs773446299, rs761963623, rs775079409, rs755705775, rs773689919, rs760624162, rs760699862, rs762086202, rs775205757, rs762111294, rs762125145, rs760733738, rs773860024, rs775323392, rs762225419, rs775369857, rs775376322, rs773919023, rs773782386, rs760694869, rs775387692, rs773967655, rs760882331, rs762340832, rs762148321, rs762202141, rs775464792, rs775131844, rs762435356, rs775544399, rs762034007, rs762510204, rs775614853, rs775627209, rs773976748, rs760891383, rs760906241, rs774029965, rs775822699, rs762720619, rs774047193, rs774053322, rs762804252, rs774058465, rs774129861, rs761104208, rs762966087, rs762968069, rs776089462, rs761185751, rs774332033, rs774469859, rs776158237, rs774482073, rs774589810, rs761511663, rs763179120, rs761511750, rs774646303, rs761588559, rs774694132, rs774728176, rs761697288, rs774886139, rs774922349, rs761826946, rs761845760, rs775063793, rs762003012, rs776637872, rs776654464, rs763546628, rs775110547, rs762276860, rs775383881, rs775461240, rs762422181, rs776740578, rs763649134, rs775386066, rs762309744, rs762328054, rs762349561, rs763826888, rs776958522, rs763851219, rs763608389, rs776992703, rs763887905, rs776685090, rs763905132, rs763962939, rs763974094, rs777096875, rs764029915, rs763580952, rs775580427, rs762627922, rs777288188, rs762666941, rs762675794, rs775794317, rs762726532, rs762730738, rs762889511, rs762892329, rs762959657, rs763002281, rs763002290, rs763012243, rs776218442, rs777563631, rs776244370, rs777622383, rs776251366, rs776332292, rs763230781, rs776360258, rs776427552, rs764653324, rs776476300, rs763360058, rs763363216, rs776553236, rs763457677, rs777864926, rs763480814, rs763480911, rs776628475, rs763552752, rs763566743, rs778010014, rs778022974, rs778036245, rs763698303, rs776874241, rs777012344, rs763688323, rs778143440, rs777215702, rs778289549, rs778300575, rs764096123, rs776939122, rs776981873, rs778119782, rs778380666, rs778267601, rs765112370, rs778321318, rs778494297, rs765311513, rs764145516, rs777290815, rs765318979, rs765320933, rs764873930, rs764888631, rs778333649, rs778374010, rs764194425, rs778674007, rs777339467, rs777382966, rs777418612, rs777478358, rs765540232, rs764346157, rs764347894, rs778800909, rs764349631, rs764377819, rs764399440, rs778929063, rs779079123, rs777546243, rs764445619, rs765838143, rs779164966, rs777646023, rs779192695, rs764496311, rs777703989, rs777740982, rs777812604, rs777829093, rs764661916, rs777840632, rs779461736, rs777844017, rs777855721, rs766045094, rs766058889, rs764699511, rs764719051, rs764746314, rs764794225, rs779681069, rs777969265, rs779840641, rs779874157, rs778055850, rs778396766, rs779957394, rs766239824, rs780023870, rs780043145, rs766263796, rs766274346, rs778441261, rs765258572, rs780109322, rs778501127, rs765316534, rs766324084, rs778543495, rs765369653, rs778602129, rs766393434, rs780316047, rs765423637, rs778611965, rs780347157, rs765492974, rs765497371, rs778714853, rs780447105, rs765533323, rs766481843, rs780503041, rs780639638, rs765541870, rs780693341, rs778736307, rs765643844, rs765653200, rs765673912, rs765800389, rs766622658, rs780798844, rs779132370, rs766649583, rs779175706, rs779230028, rs779282960, rs779344629, rs779375751, rs765948436, rs779425422, rs781124123, rs779450397, rs765993652, rs766010851, rs766066655, rs766071038, rs779649545, rs779679057, rs779738791, rs766206300, rs766879944, rs779928230, rs766901141, rs766933679, rs780083168, rs766940667, rs766287305, rs766299085, rs766300702, rs781535786, rs781539021, rs781551678, rs780193488, rs780222163, rs780296350, rs766400518, rs796125137, rs767194024, rs780344643, rs767261742, rs780357335, rs766453651, rs766456874, rs780494441, rs766560176, rs796454833, rs767330330, rs766575026, rs780717433, rs796834572, rs780751522, rs796879015, rs796895878, rs796908878, rs796943897, rs780779741, rs767568953, rs767585211, rs767665163, rs780791041, rs780805821, rs767821897, rs767874262, rs780879054, rs767995767, rs768064437, rs766687711, rs766688014, rs766704428, rs768290765, rs781060177, rs781072045, rs768466223, rs781072572, rs781158522, rs781159679, rs768587771, rs768603693, rs768623038, rs768653386, rs768702122, rs768711176, rs768744959, rs768781393, rs781188766, rs768844255, rs781231699, rs768884828, rs768886558, rs781253062, rs781284676, rs766863424, rs781317195, rs781327688, rs781361862, rs781448754, rs781467412, rs766956430, rs781531817, rs767039336, rs767055311, rs781777533, rs767184929, rs796249942, rs796309254, rs767265990, rs796349008, rs796352290, rs796380704, rs796730002, rs796797940, rs796870168, rs796981058, rs767788312, rs767804500, rs767905631, rs768152740, rs768239772, rs768260693, rs768385834, rs768416620, rs768531332, rs768574136, rs768585281, rs768804885, and rs768853312.

In one example, the guide RNA used in the present disclosure may comprise at least one 20 nucleotide (nt) target nucleic acid sequence listed in Table 5. Provided in Table 5 are the gene symbol and the sequence identifier of the gene (Gene SEQ ID NO), the gene sequence including 1-5 kilobase pairs upstream and/or downstream of the target gene (Extended Gene SEQ ID NO), and the 20 nt target nucleic acid sequence (20 nt Target Sequence SEQ ID NO). In the sequence listing the respective target gene, the strand for targeting the gene (noted by a (+) strand or (−) strand in the sequence listing), the associated PAM type and the PAM sequence are described for each of the 20 nt target nucleic acid sequences (SEQ ID NO: 5305-125469). It is understood in the art that the spacer sequence, where "T" is "U," may be an RNA sequence corresponding to the 20 nt sequences listed in Table 5.

TABLE 5

Nucleic Acid Sequences

| Gene Symbol | Gene SEQ ID NO | Extended Gene SEQ ID NO | 20 nt Target Sequence SEQ ID NO |
|---|---|---|---|
| SCN9A | 5303 | 5304 | 5305-125469 |

In one example the guide RNA used in the present disclosure may comprise at least one spacer sequence that, where "T" is "U," may be an RNA sequence corresponding to a 20 nucleotide (nt) target sequence such as, but not limited to, any of SEQ ID NO: 5305-125469.

In one example, the guide RNA used in the present disclosure may comprise at least one spacer sequence which, where "T" is "U," is an RNA sequence corresponding to the 20 nt sequences such as, but not limited to, any of SEQ ID NO: 5305-125469.

In one example, a guide RNA may comprise a 20 nucleotide (nt) target nucleic acid sequence associated with the PAM type such as, but not limited to, NAAAAC, NNA-GAAW, NNGRRT, NNNNGHTT, NRG, or YTN. As a non-limiting example, the 20 nt target nucleic acid sequence for a specific target gene and a specific PAM type may be, where "T" is "U," the RNA sequence corresponding to any one of the 20 nt nucleic acid sequences in Table 6.

TABLE 6

Nucleic Acid Sequences by PAM Type

| Gene Symbol | PAM: NAAAAC 20 nt Target Nucleic Acid SEQ ID NO | PAM: NNAGAAW 20 nt Target Nucleic Acid SEQ ID NO | PAM: NNGRRT 20 nt Target Nucleic Acid SEQ ID NO | PAM: NNNNGHTT 20 nt Target Nucleic Acid SEQ ID NO | PAM: NRG 20 nt Target Nucleic Acid SEQ ID NO | PAM: YTN 20 nt Target Nucleic Acid SEQ ID NO |
|---|---|---|---|---|---|---|
| SCN9A | 5305-6250 | 6251-8561 | 8562-13614 | 13615-18988 | 18989-56863 | 56864-125469 |

In one example, a guide RNA may comprise a 20 nucleotide (nt) target nucleic acid sequence associated with the YTN PAM type. As a non-limiting example, the 20 nt target nucleic acid sequence for a specific target gene may comprise a 20 nt core sequence where the 20 nt core sequence, where "T" is "U," may be the RNA sequence corresponding to SEQ ID NO: 56864-125469. As another non-limiting example, the 20 nt target nucleic acid sequence for a specific target gene may comprise a core sequence where the core sequence, where "T" is "U," may be a fragment, segment or region of the RNA sequence corresponding to any of SEQ ID NO: 56864-125469.

VI. Other Therapeutic Approaches

Gene editing can be conducted using nucleases engineered to target specific sequences. To date there are four major types of nucleases: meganucleases and their derivatives, zinc finger nucleases (ZFNs), transcription activator like effector nucleases (TALENs), and CRISPR-Cas9 nuclease systems. The nuclease platforms vary in difficulty of design, targeting density and mode of action, particularly as the specificity of ZFNs and TALENs is through protein-DNA interactions, while RNA-DNA interactions primarily guide Cas9.

CRISPR endonucleases, such as Cas9, can be used in the methods of the present disclosure. However, the teachings described herein, such as therapeutic target sites, could be applied to other forms of endonucleases, such as ZFNs, TALENs, HEs, or MegaTALs, or using combinations of nucleases. However, in order to apply the teachings of the present disclosure to such endonucleases, one would need to, among other things, engineer proteins directed to the specific target sites.

Additional binding domains can be fused to the Cas9 protein to increase specificity. The target sites of these constructs would map to the identified gRNA specified site, but would require additional binding motifs, such as for a zinc finger domain. In the case of Mega-TAL, a meganuclease can be fused to a TALE DNA-binding domain. The meganuclease domain can increase specificity and provide the cleavage. Similarly, inactivated or dead Cas9 (dCas9) can be fused to a cleavage domain and require the sgRNA/Cas9 target site and adjacent binding site for the fused DNA-binding domain. This likely would require some protein engineering of the dCas9, in addition to the catalytic inactivation, to decrease binding without the additional binding site.

Zinc Finger Nucleases

Zinc finger nucleases (ZFNs) are modular proteins comprised of an engineered zinc finger DNA binding domain linked to the catalytic domain of the type II endonuclease FokI. Because FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN is typically comprised of 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect of ZFNs is that they can be readily re-targeted to almost any genomic address simply by modifying individual fingers, although considerable expertise is required to do this well. In most applications of ZFNs, proteins of 4-6 fingers are used, recognizing 12-18 bp respectively. Hence, a pair of ZFNs will typically recognize a combined target sequence of 24-36 bp, not including the typical 5-7 bp spacer between half-sites. The binding sites can be separated further with larger spacers, including 15-17 bp. A target sequence of this length is likely to be unique in the human genome, assuming repetitive sequences or gene homologs are excluded during the design process. Nevertheless, the ZFN protein-DNA interactions are not absolute in their specificity so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other, and not with themselves. Forcing the obligate heterodimer prevents formation of the homodimer. This has greatly enhanced specificity of ZFNs, as well as any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., Proc Natl Acad Sci USA 96(6):2758-63 (1999); Dreier B et al., J Mol Biol. 303(4):489-502 (2000); Liu Q et al., J Biol Chem. 277(6):3850-6 (2002); Dreier et al., J Biol Chem 280(42): 35588-97 (2005); and Dreier et al., J Biol Chem. 276(31): 29466-78 (2001).

Transcription Activator-Like Effector Nucleases (TALENs)

TALENs represent another format of modular nucleases whereby, as with ZFNs, an engineered DNA binding domain is linked to the FokI nuclease domain, and a pair of TALENs operate in tandem to achieve targeted DNA cleavage. The major difference from ZFNs is the nature of the DNA binding domain and the associated target DNA sequence recognition properties. The TALEN DNA binding domain derives from TALE proteins, which were originally described in the plant bacterial pathogen *Xanthomonas* sp. TALEs are comprised of tandem arrays of 33-35 amino acid repeats, with each repeat recognizing a single base pair in the target DNA sequence that is typically up to 20 bp in length, giving a total target sequence length of up to 40 bp. Nucleotide specificity of each repeat is determined by the repeat variable diresidue (RVD), which includes just two amino acids at positions 12 and 13. The bases guanine, adenine, cytosine and thymine are predominantly recognized by the four RVDs: Asn-Asn, Asn-Ile, His-Asp and Asn-Gly, respectively. This constitutes a much simpler recognition code than for zinc fingers, and thus represents an advantage over the latter for nuclease design. Nevertheless, as with ZFNs, the protein-DNA interactions of TALENs are not absolute in their specificity, and TALENs have also benefitted from the use of obligate heterodimer variants of the FokI domain to reduce off-target activity.

Additional variants of the FokI domain have been created that are deactivated in their catalytic function. If one half of either a TALEN or a ZFN pair contains an inactive FokI domain, then only single-strand DNA cleavage (nicking) will occur at the target site, rather than a DSB. The outcome is comparable to the use of CRISPR/Cas9 or CRISPR/Cpf1 "nickase" in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB, which is prone to NHEJ-mediated mis-repair.

A variety of TALEN-based systems have been described in the art, and modifications thereof are regularly reported; see, e.g., Boch, Science 326(5959):1509-12 (2009); Mak et al., Science 335(6069):716-9 (2012); and Moscou et al., Science 326(5959):1501 (2009). The use of TALENs based on the "Golden Gate" platform, or cloning scheme, has been described by multiple groups; see, e.g., Cermak et al., Nucleic Acids Res. 39(12):e82 (2011); Li et al., Nucleic Acids Res. 39(14):6315-25 (2011); Weber et al., PLoS One. 6(2):e16765 (2011); Wang et al., J Genet Genomics 41(6): 339-47, Epub 2014 May 17 (2014); and Cermak T et al., Methods Mol Biol. 1239:133-59 (2015).

Homing Endonucleases

Homing endonucleases (HEs) are sequence-specific endonucleases that have long recognition sequences (14-44 base pairs) and cleave DNA with high specificity—often at sites unique in the genome. There are at least six known families of HEs as classified by their structure, including GIY-YIG, His-Cis box, H—N—H, PD-(D/E)xK, and Vsr-like that are derived from a broad range of hosts, including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of DNA, thereby functioning as site-specific nickases. The large target sequence of HEs and the specificity that they offer have made them attractive candidates to create site-specific DSBs.

A variety of HE-based systems have been described in the art, and modifications thereof are regularly reported; see, e.g., the reviews by Steentoft et al., Glycobiology 24(8): 663-80 (2014); Belfort and Bonocora, Methods Mol Biol. 1123:1-26 (2014); Hafez and Hausner, Genome 55(8):553-69 (2012); and references cited therein.

MegaTAL/Tev-mTALEN/MegaTev

As further examples of hybrid nucleases, the MegaTAL platform and Tev-mTALEN platform use a fusion of TALE DNA binding domains and catalytically active HEs, taking advantage of both the tunable DNA binding and specificity of the TALE, as well as the cleavage sequence specificity of the HE; see, e.g., Boissel et al., NAR 42: 2591-2601 (2014); Kleinstiver et al., G3 4:1155-65 (2014); and Boissel and Scharenberg, Methods Mol. Biol. 1239: 171-96 (2015).

In a further variation, the MegaTev architecture is the fusion of a meganuclease (Mega) with the nuclease domain derived from the GIY-YIG homing endonuclease I-TevI (Tev). The two active sites are positioned ~30 bp apart on a DNA substrate and generate two DSBs with non-compatible cohesive ends; see, e.g., Wolfs et al., NAR 42, 8816-29 (2014). It is anticipated that other combinations of existing nuclease-based approaches will evolve and be useful in achieving the targeted genome modifications described herein.

dCas9-FokI or dCpf1-Fok1 and Other Nucleases

Combining the structural and functional properties of the nuclease platforms described above offers a further approach to genome editing that can potentially overcome some of the inherent deficiencies. As an example, the CRISPR genome editing system typically uses a single Cas9 endonuclease to create a DSB. The specificity of targeting is driven by a 20 or 24 nucleotide sequence in the guide RNA that undergoes Watson-Crick base-pairing with the target DNA (plus an additional 2 bases in the adjacent NAG or NGG PAM sequence in the case of Cas9 from *S. pyogenes*). Such a sequence is long enough to be unique in the human genome, however, the specificity of the RNA/DNA interaction is not absolute, with significant promiscuity sometimes tolerated, particularly in the 5' half of the target sequence, effectively reducing the number of bases that drive specificity. One solution to this has been to completely deactivate the Cas9 or Cpf1 catalytic function—retaining only the RNA-guided DNA binding function—and instead fusing a FokI domain to the deactivated Cas9; see, e.g., Tsai et al., Nature Biotech 32: 569-76 (2014); and Guilinger et al., Nature Biotech. 32: 577-82 (2014). Because FokI must dimerize to become catalytically active, two guide RNAs are required to tether two FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE, as well as the cleavage sequence specificity of I-TevI, with the expectation that off-target cleavage can be further reduced.

VII. Kits

The present disclosure provides kits for carrying out the methods described herein. A kit can include one or more of a genome-targeting nucleic acid, a polynucleotide encoding a genome-targeting nucleic acid, a site-directed polypeptide, a polynucleotide encoding a site-directed polypeptide, and/or any nucleic acid or proteinaceous molecule necessary to carry out the aspects of the methods described herein, or any combination thereof.

A kit can comprise: (1) a vector comprising a nucleotide sequence encoding a genome-targeting nucleic acid, (2) the site-directed polypeptide or a vector comprising a nucleotide sequence encoding the site-directed polypeptide, and (3) a reagent for reconstitution and/or dilution of the vector(s) and or polypeptide.

A kit can comprise: (1) a vector comprising (i) a nucleotide sequence encoding a genome-targeting nucleic acid, and (ii) a nucleotide sequence encoding the site-directed polypeptide; and (2) a reagent for reconstitution and/or dilution of the vector.

In any of the above kits, the kit can comprise a single-molecule guide genome-targeting nucleic acid. In any of the above kits, the kit can comprise a double-molecule genome-targeting nucleic acid. In any of the above kits, the kit can comprise two or more double-molecule guides or single-molecule guides. The kits can comprise a vector that encodes the nucleic acid targeting nucleic acid.

In any of the above kits, the kit can further comprise a polynucleotide to be inserted to effect the desired genetic modification.

Components of a kit can be in separate containers, or combined in a single container.

Any kit described above can further comprise one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, a diluting buffer, or the like. A kit can also comprise one or more components that can be used to facilitate or enhance the on-target binding or the cleavage of DNA by the endonuclease, or improve the specificity of targeting.

In addition to the above-mentioned components, a kit can further comprise instructions for using the components of the kit to practice the methods. The instructions for practicing the methods can be recorded on a suitable recording medium. For example, the instructions can be printed on a substrate, such as paper or plastic, etc. The instructions can be present in the kits as a package insert, in the labeling of the container of the kit or components thereof (i.e., associated with the packaging or subpackaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this case is a kit that comprises a web address where the instructions can be viewed and/or from which the instructions can be downloaded. As with the instructions, this means for obtaining the instructions can be recorded on a suitable substrate.

VIII. Specific Methods and Compositions of the Invention

Accordingly, the present disclosure relates in particular to the following non-limiting methods according to the present disclosure: In a first method, Method 1, the present disclosure provides a method for editing a Sodium Voltage-Gated Channel Alpha Subunit 9 (SCN9A) gene in a cell by genome editing comprising: introducing into the cell one or more deoxyribonucleic acid (DNA) endonucleases to effect one or more single-strand breaks (SSBs) or double-strand breaks (DSBs) within or near the SCN9A gene or SCN9A regulatory elements that results in one or more permanent insertions, deletions or mutations of at least one nucleotide within or near the SCN9A gene, thereby reducing or eliminating the expression or function of SCN9A gene products.

In another method, Method 2, the present disclosure provides an ex vivo method for treating a patient having an SCN9A related condition or disorder comprising: editing a patient specific induced pluripotent stem cell (iPSC) within or near a Sodium Voltage-Gated Channel Alpha Subunit 9 (SCN9A) gene or other DNA sequences that encode regulatory elements of the SCN9A gene; differentiating the edited iPSC into a neuron of the peripheral nervous system; and administering the neuron of the peripheral nervous system to the patient.

In another method, Method 3, the present disclosure provides an ex vivo method for treating a patient having an SCN9A related condition or disorder comprising: obtaining a patient specific induced pluripotent stem cell (iPSC); editing the iPSC within or near a Sodium Voltage-Gated Channel Alpha Subunit 9 (SCN9A) gene or other DNA sequences that encode regulatory elements of the SCN9A gene; differentiating the edited iPSC into a neuron of the peripheral nervous system; and administering the neuron of the peripheral nervous system to the patient.

In another method, Method 4, the present disclosure provides the method of Methods 2 or 3, wherein the editing step comprises: introducing into the iPSC one or more deoxyribonucleic acid (DNA) endonucleases to effect one or more single-strand breaks (SSBs) or double-strand breaks (DSBs) within or near the SCN9A gene or SCN9A regulatory elements that results in one or more permanent insertions, deletions or mutations of at least one nucleotide within or near the SCN9A gene, thereby reducing or eliminating the expression or function of SCN9A gene products.

In another method, Method 5, the present disclosure provides an ex vivo method for treating a patient having an SCN9A related condition or disorder comprising: editing a mesenchymal stem cell within or near a Sodium Voltage-Gated Channel Alpha Subunit 9 (SCN9A) gene or other DNA sequences that encode regulatory elements of the SCN9A gene; differentiating the edited mesenchymal stem cell into a neuron of the peripheral nervous system; and administering the neuron of the peripheral nervous system to the patient.

In another method, Method 6, the present disclosure provides an ex vivo method for treating a patient having an SCN9A related condition or disorder comprising: obtaining a mesenchymal stem cell from the patient; editing a mesenchymal stem cell within or near a Sodium Voltage-Gated Channel Alpha Subunit 9 (SCN9A) gene or other DNA sequences that encode regulatory elements of the SCN9A gene; differentiating the edited mesenchymal stem cell into a neuron of the peripheral nervous system; and administering the neuron of the peripheral nervous system to the patient.

In another method, Method 7, the present disclosure provides the method of Methods 5 or 6, wherein the editing step comprises: introducing into the mesenchymal stem cell one or more deoxyribonucleic acid (DNA) endonucleases to effect one or more single-strand breaks (SSBs) or double-strand breaks (DSBs) within or near the SCN9A gene or SCN9A regulatory elements that results in one or more permanent insertions, deletions or mutations of at least one nucleotide within or near the SCN9A gene, thereby reducing or eliminating the expression or function of SCN9A gene products.

In another method, Method 8, the present disclosure provides an in vivo method for treating a patient with an SCN9A related disorder comprising: editing the Sodium Voltage-Gated Channel Alpha Subunit 9 (SCN9A) gene in a cell of the patient.

In another method, Method 9, the present disclosure provides the method of Method 8, wherein the editing step comprises: introducing into the cell one or more deoxyribonucleic acid (DNA) endonucleases to effect one or more single-strand breaks (SSBs) or double-strand breaks (DSBs) within or near the SCN9A gene or SCN9A regulatory elements that results in one or more permanent insertions, deletions or mutations of at least one nucleotide within or near the SCN9A gene, thereby reducing or eliminating the expression or function of SCN9A gene products.

In another method, Method 10, the present disclosure provides the method of any one of Methods 8-9, wherein the cell is a neuron of the peripheral nervous system.

In another method, Method 11, the present disclosure provides the method of Method 10, wherein the one or more deoxyribonucleic acid (DNA) endonuclease is delivered to the neuron of the peripheral nervous system via direct intraganglionic or intraspinal injection, or intrathecal delivery.

In another method, Method 12, the present disclosure provides a method of altering the contiguous genomic sequence of an SCN9A gene in a cell comprising: contacting the cell with one or more deoxyribonucleic acid (DNA)

endonuclease to effect one or more single-strand breaks (SSBs) or double-strand breaks (DSBs).

In another method, Method 13, the present disclosure provides the method of Method 12, wherein the alteration of the contiguous genomic sequence occurs in one or more exons of the SCN9A gene.

In another method, Method 14, the present disclosure provides the method of any one of Methods 1-13, wherein the one or more deoxyribonucleic acid (DNA) endonuclease is selected from any of those in SEQ ID NOs: 1-620, and variants having at least 90% homology to any of those listed in SEQ ID NOs: 1-620.

In another method, Method 15, the present disclosure provides the method of Method 14, wherein the one or more deoxyribonucleic acid (DNA) endonuclease is one or more protein or polypeptide.

In another method, Method 16, the present disclosure provides the method of Method 14, wherein the one or more deoxyribonucleic acid (DNA) endonuclease is one or more polynucleotide encoding the one or more DNA endonuclease.

In another method, Method 17, the present disclosure provides the method of Method 16, wherein the one or more deoxyribonucleic acid (DNA) endonuclease is one or more ribonucleic acid (RNA) encoding the one or more DNA endonuclease.

In another method, Method 18, the present disclosure provides the method of Method 17, wherein the one or more ribonucleic acid (RNA) is one or more chemically modified RNA.

In another method, Method 19, the present disclosure provides the method of Method 18, wherein the one or more ribonucleic acid (RNA) is chemically modified in the coding region.

In another method, Method 20, the present disclosure provides the method of any one of Methods 16-19, wherein the one or more polynucleotide or one or more ribonucleic acid (RNA) is codon optimized.

In another method, Method 21, the present disclosure provides the method of any one of Methods 1-20, wherein the method further comprises: introducing into the cell one or more gRNA or one or more sgRNA.

In another method, Method 22, the present disclosure provides the method of Method 21, wherein the one or more gRNA or one or more sgRNA comprises a spacer sequence that is complementary to a DNA sequence within or near the SCN9A gene.

In another method, Method 23, the present disclosure provides the method of any one of Methods 21-22, wherein the one or more gRNA or one or more sgRNA is chemically modified.

In another method, Method 24, the present disclosure provides the method of any one of Methods 21-23, wherein the one or more gRNA or one or more sgRNA is pre-complexed with the one or more deoxyribonucleic acid (DNA) endonuclease.

In another method, Method 25, the present disclosure provides the method of Method 24, wherein the pre-complexing involves a covalent attachment of the one or more gRNA or one or more sgRNA to the one or more deoxyribonucleic acid (DNA) endonuclease.

In another method, Method 26, the present disclosure provides the method of any one of Methods 14-25, wherein the one or more deoxyribonucleic acid (DNA) endonuclease is formulated in a liposome or lipid nanoparticle.

In another method, Method 27, the present disclosure provides the method of any one of Methods 21-25, wherein the one or more deoxyribonucleic acid (DNA) endonuclease is formulated in a liposome or lipid nanoparticle which also comprises the one or more gRNA or one or more sgRNA.

In another method, Method 28, the present disclosure provides the method of any one of Methods 12, or 21-22, wherein the one or more deoxyribonucleic acid (DNA) endonuclease is encoded in an AAV vector particle.

In another method, Method 29, the present disclosure provides the method of any one of Methods 21-22, wherein the one or more gRNA or one or more sgRNA is encoded in an AAV vector particle.

In another method, Method 30, the present disclosure provides the method of any one of Methods 21-22, wherein the one or more deoxyribonucleic acid (DNA) endonuclease is encoded in an AAV vector particle which also encodes the one or more gRNA or one or more sgRNA.

In another method, Method 31, the present disclosure provides the method of any of the Methods 28-30, where the AAV vector particle is selected from the group consisting of any of those disclosed in SEQ ID NOs: 4734-5302 and Table 2.

The present disclosure also provides a composition, Composition 1, comprising a single-molecule guide RNA comprising: at least a spacer sequence that is an RNA sequence corresponding to any of SEQ ID NOs: 5305-125469.

In another composition, Composition 2, the present disclosure provides the single-molecule guide RNA of Composition 1, wherein the single-molecule guide RNA further comprises a spacer extension region.

In another composition, Composition 3, the present disclosure provides the single-molecule guide RNA of Composition 1, wherein the single-molecule guide RNA further comprises a tracrRNA extension region.

In another composition, Composition 4, the present disclosure provides the single-molecule guide RNA of Compositions 1-3, wherein the single-molecule guide RNA is chemically modified.

In another composition, Composition 5, the present disclosure provides a single-molecule guide RNA of Compositions 1-4 pre-complexed with a site-directed polypeptide.

In another composition, Composition 6, the present disclosure provides a single-molecule guide RNA of Compositions 1-5 pre-complexed with a DNA endonuclease.

In another composition, Composition 7, the present disclosure provides the composition of Composition 6, wherein the DNA endonuclease is a Cas9 or Cpf1 endonuclease.

In another composition, Composition 8, the present disclosure provides the composition of Composition 7, wherein the Cas9 or Cpf1 endonuclease is selected from the group consisting of: *S. pyogenes* Cas9, *S. aureus* Cas9, *N. meningitides* Cas9, *S. thermophilus* CRISPR1 Cas9, *S. thermophilus* CRISPR 3 Cas9, *T. denticola* Cas9, *L. bacterium* ND2006 Cpf1 and *Acidaminococcus* sp. BV3L6 Cpf1, and variants having at least 90% homology to the endonucleases.

In another composition, Composition 9, the present disclosure provides the composition of Composition 8, wherein the Cas9 or Cpf1 endonuclease comprises one or more nuclear localization signals (NLSs).

In another composition, Composition 10, the present disclosure provides the composition of Composition 9, wherein at least one NLS is at or within 50 amino acids of the amino-terminus of the Cas9 or Cpf1 endonuclease and/or at least one NLS is at or within 50 amino acids of the carboxy-terminus of the Cas9 or Cpf1 endonuclease.

In another composition, Composition 11, the present disclosure provides a DNA encoding the single-molecule guide RNA of any of Compositions 1-4.

In another composition, Composition 12, the present disclosure provides a non-naturally occurring CRISPR/Cas system comprising a polynucleotide encoding a Cas9 or Cpf1 endonuclease and at least one single-molecule guide RNA of Compositions 1-4.

In another composition, Composition 13, the present disclosure provides the CRISPR/Cas system of Composition 11, wherein the polynucleotide encoding a Cas9 or Cpf1 endonuclease is selected from the group consisting of: *S. pyogenes* Cas9, *S. aureus* Cas9, *N. meningitides* Cas9, *S. thermophilus* CRISPR1 Cas9, *S. thermophilus* CRISPR 3 Cas9, *T. denticola* Cas9, *L. bacterium* ND2006 Cpf1 and *Acidaminococcus* sp. BV3L6 Cpf1, and variants having at least 90% homology to the endonucleases.

In another composition, Composition 14, the present disclosure provides the CRISPR/Cas system of Composition 13, wherein the polynucleotide encoding a Cas9 or Cpf1 endonuclease comprises one or more nuclear localization signals (NLSs).

In another composition, Composition 15, the present disclosure provides the CRISPR/Cas system of Composition 14, wherein at least one NLS is at or within 50 amino acids of the amino-terminus of the polynucleotide encoding a Cas9 or Cpf1 endonuclease and/or at least one NLS is at or within 50 amino acids of the carboxy-terminus of the polynucleotide encoding a Cas9 or Cpf1 endonuclease.

In another composition, Composition 16, the present disclosure provides the CRISPR/Cas system of Composition 15, wherein the polynucleotide encoding a Cas9 or Cpf1 endonuclease is codon optimized for expression in a eukaryotic cell.

In another composition, Composition 17, the present disclosure provides a DNA encoding the CRISPR/Cas system of any one of Compositions 12-16.

In another composition, Composition 18, the present disclosure provides a vector comprising the DNA of any one of Compositions 12-17.

In another composition, Composition 19, the present disclosure provides the vector of Composition 18, wherein the vector is a plasmid.

In another composition, Composition 20, the present disclosure provides the vector of Composition 18, wherein the vector is an AAV vector particle, and the AAV vector serotype is selected from the group consisting of those disclosed in SEQ ID NOs: 4734-5302 and Table 2.

IX. Definitions

The term "comprising" or "comprises" is used in reference to compositions, methods, and respective component(s) thereof, that are essential to the present disclosure, yet open to the inclusion of unspecified elements, whether essential or not.

The term "consisting essentially of" refers to those elements required for a given aspect. The term permits the presence of additional elements that do not materially affect the basic and novel or functional characteristic(s) of that aspect of the present disclosure.

The term "consisting of" refers to compositions, methods, and respective components thereof as described herein, which are exclusive of any element not recited in that description of the aspect.

The singular forms "a," "an," and "the" include plural references, unless the context clearly dictates otherwise.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with written description, sufficiency of description, and added matter requirements, including the requirements under 35 U.S.C. § 112(a) and Article 123(2) EPC. Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameter.

The details of one or more examples of the present disclosure are set forth in the accompanying description below. Although any materials and methods similar or equivalent to those described herein can be used in the practice or testing of the present disclosure, the preferred materials and methods are now described. Other features, objects and advantages of the present disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this present disclosure belongs. In the case of conflict, the present description will control.

The present disclosure is further illustrated by the following non-limiting examples.

X. Examples

The present disclosure will be more fully understood by reference to the following examples, which provide illustrative non-limiting aspects of the invention.

The examples describe the use of the CRISPR system as an illustrative genome editing technique to create defined therapeutic genomic deletions, insertions, or replacements, termed "genomic modifications" herein, in the SCN9A gene that lead to permanent deletion or mutation of the SCN9A gene, that reduce or eliminate the SCN9A protein activity. Introduction of the defined therapeutic modifications represents a novel therapeutic strategy for the potential amelioration of Pain, as described and illustrated herein.

Various Cas orthologs are evaluated for cutting. gRNAs are delivered as RNA and expressed from the U6 promoter in plasmids. The corresponding Cas protein is either knocked into the cell line of interest and constitutively expressed, delivered as mRNA, or delivered as protein. The gRNA activity in all formats is evaluated using TIDE analysis in HEK293T cells.

Introduction of the defined therapeutic modifications described above represents a novel therapeutic strategy for the potential amelioration of Pain and related disorders, as described and illustrated herein.

Example 1

CRISPR/SpCas9 Target Sites for the SCN9A Gene

Regions of the SCN9A gene were scanned for target sites. Each area was scanned for a protospacer adjacent motif (PAM) having the sequence NRG. gRNA 20 bp spacer sequences corresponding to the PAM were then identified, as shown in SEQ ID NOs: 18989-56863 of the Sequence Listing.

Example 2

CRISPR/SaCas9 Target Sites for the SCN9A Gene

Regions of the SCN9A gene were scanned for target sites. Each area was scanned for a protospacer adjacent motif (PAM) having the sequence NNGRRT. gRNA 20 bp spacer sequences corresponding to the PAM were then identified, as shown in SEQ ID NOs: 8562-13614 of the Sequence Listing.

Example 3

CRISPR/StCas9 Target Sites for the SCN9A Gene

Regions of the SCN9A gene were scanned for target sites. Each area was scanned for a protospacer adjacent motif (PAM) having the sequence NNAGAAW. gRNA 20 bp spacer sequences corresponding to the PAM were then identified, as shown in SEQ ID NOs: 6251-8561 of the Sequence Listing.

Example 4

CRISPR/TdCas9 Target Sites for the SCN9A Gene

Regions of the SCN9A gene were scanned for target sites. Each area was scanned for a protospacer adjacent motif (PAM) having the sequence NAAAAC. gRNA 20 bp spacer sequences corresponding to the PAM were then identified, as shown in SEQ ID NOs: 5305-6250 of the Sequence Listing.

Example 5

CRISPR/NmCas9 Target Sites for the SCN9A Gene

Regions of the SCN9A gene were scanned for target sites. Each area was scanned for a protospacer adjacent motif (PAM) having the sequence NNNNGHTT. gRNA 20 bp spacer sequences corresponding to the PAM were then identified, as shown in SEQ ID NOs: 13615-18988 of the Sequence Listing.

Example 6

CRISPR/Cpf1 Target Sites for the SCN9A Gene

Regions of the SCN9A gene were scanned for target sites. Each area was scanned for a protospacer adjacent motif (PAM) having the sequence YTN. gRNA 20 bp spacer sequences corresponding to the PAM were then identified, as shown in SEQ ID NOs: 56864-125469 of the Sequence Listing.

Example 7

Bioinformatics Analysis of the Guide Strands

Candidate guides will then screened and selected in a single process or multi-step process that involves both theoretical binding and experimentally assessed activity at both on-target and off-target sites. By way of illustration, candidate guides having sequences that match a particular on-target site, such as a site within the SCN9A gene, with adjacent PAM can be assessed for their potential to cleave at off-target sites having similar sequences, using one or more of a variety of bioinformatics tools available for assessing off-target binding, as described and illustrated in more detail below, in order to assess the likelihood of effects at chromosomal positions other than those intended.

Candidates predicted to have relatively lower potential for off-target activity can then be assessed experimentally to measure their on-target activity, and then off-target activities at various sites. Preferred guides have sufficiently high on-target activity to achieve desired levels of gene editing at the selected locus, and relatively lower off-target activity to reduce the likelihood of alterations at other chromosomal loci. The ratio of on-target to off-target activity is often referred to as the "specificity" of a guide.

For initial screening of predicted off-target activities, there are a number of bioinformatics tools known and publicly available that can be used to predict the most likely off-target sites; and since binding to target sites in the CRISPR/Cas9 or CRISPR/Cpf1 nuclease system is driven by Watson-Crick base pairing between complementary sequences, the degree of dissimilarity (and therefore reduced potential for off-target binding) is essentially related to primary sequence differences: mismatches and bulges, i.e. bases that are changed to a non-complementary base, and insertions or deletions of bases in the potential off-target site relative to the target site. An exemplary bioinformatics tool called COSMID (CRISPR Off-target Sites with Mismatches, Insertions and Deletions) (available on the web at crispr.b-me.gatech.edu) compiles such similarities. Other bioinformatics tools include, but are not limited to, autoCOSMID and CCTop.

Bioinformatics were used to minimize off-target cleavage in order to reduce the detrimental effects of mutations and chromosomal rearrangements. Studies on CRISPR/Cas9 systems suggested the possibility of off-target activity due to non-specific hybridization of the guide strand to DNA sequences with base pair mismatches and/or bulges, particularly at positions distal from the PAM region. Therefore, it is important to have a bioinformatics tool that can identify potential off-target sites that have insertions and/or deletions between the RNA guide strand and genomic sequences, in addition to base-pair mismatches. Bioinformatics tools based upon the off-target algorithm CCTop were used to search genomes for potential CRISPR off-target sites (CCTop is available on the web at crispr.cos.uni-heidelberg.de/). The output ranked lists of the potential off-target sites based on the number and location of mismatches, allowing more informed choice of target sites, and avoiding the use of sites with more likely off-target cleavage.

Additional bioinformatics pipelines are employed that weigh the estimated on- and/or off-target activity of gRNA targeting sites in a region. Other features that may be used to predict activity include information about the cell type in question, DNA accessibility, chromatin state, transcription factor binding sites, transcription factor binding data, and other CHIP-seq data. Additional factors are weighed that predict editing efficiency, such as relative positions and directions of pairs of gRNAs, local sequence features and micro-homologies.

Initial evaluation and screening of CRISPR/Cas9 target sites focused on Exons 2-17 of the SCN9A gene and 100-300 bp of sequences from Introns 2-16 that flank these exons. These gRNAs can also be used to edit one or more nucleotides, exonic sequences and/or intronic sequences.

Initial bioinformatics analysis identified, 602 gRNAs targeting Exons 2-17, Introns 2-16, and 100-300 bp sequences flanking the intronic sequences. Further analysis of predicted off-target sites and evaluation of the gRNA target site within the SCN9A gene resulted in 192 gRNAs selected for screening. The prioritized list of 192 single gRNAs targeting the SCN9A gene was tested for cutting efficiencies using spCas9 (Table 7).

TABLE 7

| SEQ ID NO. | Name | Sequence |
| --- | --- | --- |
| 46832 | SCN9A_Int13_Int14_T4 | TGTGCAAATCTGTACCACCA |
| 49122 | SCN9A_Int5_Int6_T10 | CAAATAGTTGGAGTTATGAG |
| 49431 | SCN9A_Int2_Int5_T31 | CAGCAGTTTACCTTTCTACA |
| 47474 | SCN9A_Int10_Int11_T22 | CACCTATTAGCATAACAACA |
| 47446 | SCN9A_Int10_Int11_T6 | TATGCCCTTCGACACCAAGG |
| 28779 | SCN9A_Int8_Int9_T21 | GAGCTTTGACACTTTCAGCT |
| 29821 | SCN9A_Int6_Int7_T3 | CAGGCCTGAAGACAATTGTA |
| 28146 | SCN9A_Int10_Int11_T17 | GTGAAAGATGTCCTGTCCTA |
| 49436 | SCN9A_Int2_Int5_T35 | GCCATCAGACTCCAGCAATG |
| 47224 | SCN9A_Int11_Int12_T26 | CTGGCAGAAGCTGTCCATTG |
| 47462 | SCN9A_Int10_Int11_T12 | CCGCTGCCGCTGCAATTGCC |
| 47240 | SCN9A_Int11_Int12_T3 | CGTTCACCGGCAGCATTGGT |
| 27323 | SCN9A_Int14_Int15_T1 | AGTTCTGCGATCATTCAGAC |
| 27522 | SCN9A_Int13_Int14_T2 | GGAACACCACCCAATGACTG |
| 27893 | SCN9A_Int11_Int12_T20 | TAGGTCCCCACCAATGCTGC |
| 47261 | SCN9A_Int11_Int12_T28 | AAGGAGCCACGAATGCTGAG |
| 28137 | SCN9A_Int10_Int11_T21 | GCCCAACCAGGCAATTGCAG |
| 49367 | SCN9A_Int2_Int5_T8 | CCAGTCCGGTGGGTTATTCA |
| 47232 | SCN9A_Int11_Int12_T8 | GGCTGAGCGTCCATCAACCA |
| 47445 | SCN9A_Int10_Int11_T7 | GCCTATGCCCTTCGACACCA |
| 49313 | SCN9A_Int2_Int5_T38 | TATATTGGAGGATGGCTGTT |
| 47267 | SCN9A_Int11_Int12_T24 | ATAAATACCACTGAACCCAC |
| 30622 | SCN9A_Int1_Int2_T9 | CCATCCAGGCCTCTTATGTG |
| 47231 | SCN9A_Int11_Int12_T5 | GGGCTGAGCGTCCATCAACC |
| 26766 | SCN9A_Int16_Int17_T10 | TGACAGTGCCAATTGCACCT |
| 28139 | SCN9A_Int10_Int11_T4 | GTTAACGTCTTGGCCCAACC |
| 46079 | SCN9A_Int16_Int17_T9 | TAGGTTTAGGACCTATATCA |
| 48091 | SCN9A_Int8_Int9_T18 | CTCAAGGTTTCTTCTATAGG |

TABLE 7-continued

| SEQ ID NO. | Name | Sequence |
| --- | --- | --- |
| 46833 | SCN9A_Int13_Int14_T1 | GCAAATCTGTACCACCAAGG |
| 26765 | SCN9A_Int16_Int17_T16 | GACAGTGCCAATTGCACCTG |
| 27876 | SCN9A_Int11_Int12_T27 | GCCAGAGGTGATAATAGATA |
| 47241 | SCN9A_Int11_Int12_T18 | GTTCACCGGCAGCATTGGTG |
| 47248 | SCN9A_Int11_Int12_T22 | GCGTCGCTCCTGGGGTCTGT |
| 30051 | SCN9A_Int2_Int5_T34 | CCCAATGGAATCTTGTGTTT |
| 30111 | SCN9A_Int2_Int5_T18 | TATGACCATGAATAACCCAC |
| 28760 | SCN9A_Int8_Int9_T16 | TGTTAAGAGCCTGTATTAGG |
| 28085 | SCN9A_Int10_Int11_T23 | ATAGGCGAGCACATGAAAAG |
| 27254 | SCN9A_Int15_Int16_T19 | AAGATCATTGGTAACTCAGT |
| 30163 | SCN9A_Int2_Int5_T9 | GATAGATGCGTTGATGACAT |
| 49303 | SCN9A_Int2_Int5_T44 | CCTAAACACAAGATTCCATT |
| 28083 | SCN9A_Int10_Int11_T2 | GAGGTTGTCTACCCCCAATC |
| 49344 | SCN9A_Int2_Int5_T30 | GCAGGTTAATATCATAGAGG |
| 47245 | SCN9A_Int11_Int12_T2 | GTTACTGCTGCGTCGCTCCT |
| 48090 | SCN9A_Int8_Int9_T22 | ACTCAAGGTTTCTTCTATAG |
| 28132 | SCN9A_Int10_Int11_T16 | CGGCTGAATATACAAGTATT |
| 27328 | SCN9A_Int14_Int15_T2 | GGAGCTCTTTCTAGCAGATG |
| 46078 | SCN9A_Int16_Int17_T8 | ATAGGTTTAGGACCTATATC |
| 28773 | SCN9A_Int8_Int9_T7 | GCTAATGACCCAAGATTACT |
| 46496 | SCN9A_Int15_Int16_T12 | ACATCTGGTTACATACCACC |
| 27885 | SCN9A_Int11_Int12_T23 | GGTGTGGTCTCCCTGGTTGA |
| 29928 | SCN9A_Int5_Int6_T2 | AATACCTTGACTAAAGGCTC |
| 27933 | SCN9A_Int11_Int12_T7 | CAGTCACCACTCAGCATTCG |
| 46039 | SCN9A_Int16_Int17_T2 | TTTTCCAAATCGGATTCCCC |
| 47439 | SCN9A_Int10_Int11_T10 | CAATTTGGGTGGTACCTGAT |
| 28774 | SCN9A_Int8_Int9_T1 | GGCTAATGACCCAAGATTAC |
| 47455 | SCN9A_Int10_Int11_T24 | AGCACTTTTAGAGCTCAGTT |
| 30020 | SCN9A_Int2_Int5_T24 | TATGAAAGCTAGTCATTGAT |
| 47236 | SCN9A_Int11_Int12_T15 | CTGTGCATTTTCCCGTTCAC |
| 28089 | SCN9A_Int10_Int11_T3 | ACCTTGGTGTCGAAGGGCAT |
| 26813 | SCN9A_Int16_Int17_T14 | ATAGGTCCTAAACCTATTTC |
| 47464 | SCN9A_Int10_Int11_T9 | GCCGCTGCAATTGCCTGGTT |
| 28091 | SCN9A_Int10_Int11_T8 | GTTTCCACCTTGGTGTCGAA |
| 29908 | SCN9A_Int5_Int6_T11 | AGTAATTGGTGTGAAGCATT |
| 27892 | SCN9A_Int11_Int12_T12 | CCACCAATGCTGCCGGTGAA |
| 28776 | SCN9A_Int8_Int9_T15 | GGGCCTTCTTAGCCTTGTTT |
| 28783 | SCN9A_Int8_Int9_T17 | ATTGGCAGAAACCCTGATTA |
| 27252 | SCN9A_Int15_Int16_T13 | GATCATTGGTAACTCAGTAG |

TABLE 7-continued

| SEQ ID NO. | Name | Sequence |
|---|---|---|
| 29930 | SCN9A_Int5_Int6_T12 | GTAGAAAATACCTTGACTAA |
| 47625 | SCN9A_Int9_Int10_T1 | CCAGCAGCACGCAGCGTCTA |
| 49945 | SCN9A_Int1_Int2_T16 | AGCAATGCGTTGTTCAATGA |
| 30106 | SCN9A_Int2_Int5_T10 | ACCAAAAATGTCGAGTAAGT |
| 48060 | SCN9A_Int8_Int9_T12 | TTGGGTCATTAGCCTAAACA |
| 29831 | SCN9A_Int6_Int7_T8 | GATATAATGCATGACTTTCT |
| 47239 | SCN9A_Int11_Int12_T10 | CCGTTCACCGGCAGCATTGG |
| 49355 | SCN9A_Int2_Int5_T41 | TCATAAATGCAGTAACTTCC |
| 26774 | SCN9A_Int16_Int17_T7 | CAGCGTGGACAAACACTTGA |
| 30050 | SCN9A_Int2_Int5_T15 | GTGTTTAGGTACACTTTTAC |
| 47246 | SCN9A_Int11_Int12_T9 | TTACTGCTGCGTCGCTCCTG |
| 27250 | SCN9A_Int15_Int16_T16 | GGTAACTCAGTAGGGGCTCT |
| 49124 | SCN9A_Int5_Int6_T9 | ACACCAATTACTTCTTACCT |
| 30053 | SCN9A_Int2_Int5_T22 | TTTCACATCTAGTATCCCAA |
| 49362 | SCN9A_Int2_Int5_T11 | ACCCACTTACTCGACATTTT |
| 47238 | SCN9A_Int11_Int12_T11 | TTCCCGTTCACCGGCAGCAT |
| 49418 | SCN9A_Int2_Int5_T45 | AAGCAGGTGTGGCATTGAAA |
| 27544 | SCN9A_Int13_Int14_T3 | ATGCCTGACTGATTTGTATC |
| 46080 | SCN9A_Int16_Int17_T5 | GTTTAGGACCTATATCAGGG |
| 26775 | SCN9A_Int16_Int17_T15 | CAGTGGTTTTGGAAGCAGCG |
| 30079 | SCN9A_Int2_Int5_T4 | ATTTTTGATAGAAGCAATGT |
| 48052 | SCN9A_Int8_Int9_T8 | TTCTCTTGGTACTCACCTGT |
| 46081 | SCN9A_Int16_Int17_T6 | TTTAGGACCTATATCAGGGT |
| 49424 | SCN9A_Int2_Int5_T40 | ATACTATGAAAGTCTGCAGG |
| 47440 | SCN9A_Int10_Int11_T14 | AATTTGGGTGGTACCTGATT |
| 49331 | SCN9A_Int2_Int5_T36 | TGTGTAACATGTCTAAGAAC |
| 30612 | SCN9A_Int1_Int2_T5 | ATGGCAATGTTGCCTCCCCC |
| 47441 | SCN9A_Int10_Int11_T18 | ATTTGGGTGGTACCTGATTG |
| 47626 | SCN9A_Int9_Int10_T7 | ACGCAGCGTCTAGGGAAAAA |
| 49314 | SCN9A_Int2_Int5_T23 | GGAGGATGGCTGTTGGGTTA |
| 27530 | SCN9A_Int13_Int14_T5 | TCTGGAATTGCTCTCCATAT |
| 48081 | SCN9A_Int8_Int9_T14 | TTATAGGTGAGAGTGTCTTC |
| 30065 | SCN9A_Int2_Int5_T42 | TAGACCTATTGTAGTTTAAT |
| 46040 | SCN9A_Int16_Int17_T4 | TCGGATTCCCCAGGTGCAAT |
| 49962 | SCN9A_Int1_Int2_T24 | AGCTCCTCACATAAGAGGCC |
| 49976 | SCN9A_Int1_Int2_T14 | CTAGAATTATCAGCTTGTTA |
| 27248 | SCN9A_Int_15_Int16_T15 | AGGTAACCTCACCTTAGTGT |
| 29814 | SCN9A_Int6_Int7_T2 | CTGAGTGTGTTTGCACTAAT |
| 30162 | SCN9A_Int2_Int5_T25 | TGACATTGGAACCACATTGC |
| 49302 | SCN9A_Int2_Int5_T33 | ACCTAAACACAAGATTCCAT |
| 49366 | SCN9A_Int2_Int5_T1 | CATTTTTGGTCCAGTCCGGT |
| 26764 | SCN9A_Int16_Int17_T1 | TGCACCTGGGGAATCCGATT |
| 46082 | SCN9A_Int16_Int17_T11 | TTAGGACCTATATCAGGGTG |
| 49048 | SCN9A_Int6_Int7_T1 | AAGCCCCTACAATTGTCTTC |
| 28788 | SCN9A_Int8_Int9_T11 | CGTGTGTAGTCAGTGTCCAG |
| 47633 | SCN9A_Int9_Int10_T10 | CATGAGCAAATCTGACAGTT |
| 49290 | SCN9A_Int2_Int5_T28 | CAAAATCCAGCCAGTTCCAC |
| 27222 | SCN9A_Int15_Int16_T17 | TACATGATGGTCATGGTCAT |
| 30107 | SCN9A_Int2_Int5_T14 | GACCAAAAATGTCGAGTAAG |
| 27336 | SCN9A_Int14_Int15_T3 | ATGAGTATTTCCAAGTAGGC |
| 49142 | SCN9A_Int5_Int6_T3 | CTTACCTGAGCCTTTAGTCA |
| 48073 | SCN9A_Int8_Int9_T4 | TTCACACAGGTGTACCCCTC |
| 28305 | SCN9A_Int9_Int10_T9 | CTTTGTCGTAGTGATTTTCC |
| 49145 | SCN9A_Int5_Int6_T4 | CAAGGTATTTTCTACGTTTG |
| 30061 | SCN9A_Int2_Int5_T32 | CTCCAATATATGTCTTCCAG |
| 47463 | SCN9A_Int10_Int11_T11 | TGCCGCTGCAATTGCCTGGT |
| 48054 | SCN9A_Int8_Int9_T5 | TGGTACTCACCTGTTGGTAA |
| 49365 | SCN9A_Int2_Int5_T6 | ACATTTTTGGTCCAGTCCGG |
| 27253 | SCN9A_Int15_Int16_T18 | AGATCATTGGTAACTCAGTA |
| 49352 | SCN9A_Int2_Int5_T37 | AGCAAGCATATAACATGGGA |
| 30110 | SCN9A_Int2_Int5_T2 | CCATGAATAACCCACCGGAC |
| 27887 | SCN9A_Int11_Int12_T14 | TGCTGTGGACTGCAACGGTG |
| 47243 | SCN9A_Int11_Int12_T17 | TTGGTGGGACCTACTGGCT |
| 27868 | SCN9A_Int11_Int12_125 | TTACATAGCTCAGGCATGGC |
| 27891 | SCN9A_Int11_Int12_T6 | CACCAATGCTGCCGGTGAAC |
| 46834 | SCN9A_Int13_Int14_T7 | CCAAGGTGGACATTTTTGTC |
| 30043 | SCN9A_Int2_Int5_T5 | TCACTTTTCTTCGTGACCCG |
| 49944 | SCN9A_Int1_Int2_T2 | CAGCAATGCGTTGTTCAATG |
| 49316 | SCN9A_Int2_Int5_T29 | ACACCCTATTAAACTACAAT |
| 26767 | SCN9A_Int16_Int17_T3 | GTGACAGTGCCAATTGCACC |
| 28273 | SCN9A_Int9_Int10_T3 | GAGGCTCTGCGGTATATGCT |
| 47242 | SCN9A_Int11_Int12_T13 | CAGCATTGGTGGGACCTAC |
| 47624 | SCN9A_Int9_Int10_T2 | GCCAGCAGCACGCAGCGTCT |
| 29811 | SCN9A_Int6_Int7_T6 | ATTGGACTACAGCTGTTCAT |
| 49422 | SCN9A_Int2_Int5_T27 | TCAATACTATGAAAGTCTGC |
| 28081 | SCN9A_Int10_Int11_T1 | TGCTAAATGTGTATCACCCG |
| 46050 | SCN9A_Int16_Int17_T17 | TGCTCATTTCAGCAAGTGTA |

TABLE 7-continued

| SEQ ID NO. | Name | Sequence |
|---|---|---|
| 27870 | SCN9A_Int11_Int12_T16 | AAGGACGTTTTACATAGCTC |
| 47472 | SCN9A_Int10_Int11_T15 | ATCCTAGGAAACCCTAGGAC |
| 49952 | SCN9A_Int1_Int2_T27 | TGGACAAAGCTCTGAGGTCC |
| 28780 | SCN9A_Int8_Int9_T9 | CGAGCTTTGACACTTTCAGC |
| 46099 | SCN9A_Int16_Int17_T13 | AAGTACACTTTTCCGAATAT |
| 49143 | SCN9A_Int5_Int6_T1 | GTCAAGGTATTTTCTACGTT |
| 28150 | SCN9A_Int10_Int11_T19 | CACCATGTTGTTATGCTAAT |
| 27873 | SCN9A_Int11_Int12_T4 | CAACTTCTGATGACAGCGTA |
| 47244 | SCN9A_Int11_Int12_T1 | TGTTACTGCTGCGTCGCTCC |
| 30041 | SCN9A_Int2_Int5_T7 | TCGTGACCCGTGGAACTGGC |
| 47604 | SCN9A_Int9_Int10_T8 | TAGCTTCTTCAATGTTTGCC |
| 49357 | SCN9A_Int2_Int5_T43 | AAATGCAGTAACTTCCTGGC |
| 28275 | SCN9A_Int9_Int10_T5 | AATGCAAACGGTTACAACAG |
| 28092 | SCN9A_Int10_Int11_T5 | AGTTTCCACCTTGGTGTCGA |
| 49283 | SCN9A_Int2_Int5_T19 | CCCCAGAGGTTTGCTGTTAT |
| 28141 | SCN9A_Int10_Int11_T13 | TCATTTAAGTGTTAACGTCT |
| 30628 | SCN9A_Int1_Int2_T20 | TTTAATGGGCCTTTCTTGGC |
| 46066 | SCN9A_Int16_Int17_T12 | ATCTGGAGGTTGTTTGCATC |
| 49364 | SCN9A_Int2_Int5_T12 | TCGACATTTTTGGTCCAGTC |
| 28307 | SCN9A_Int9_Int10_T4 | CCCTAGACGCTGCGTGCTGC |
| 28143 | SCN9A_Int10_Int11_T20 | TCCTAGGGTTTCCTAGGATT |

Note that the SEQ ID NOs represent the DNA sequence of the genomic target, while the gRNA or sgRNA spacer sequence will be the RNA version of the DNA sequence.

Example 8

Testing of Preferred Guides in In Vitro Transcribed (IVT) gRNA Screen

To identify a large spectrum of pairs of gRNAs able to edit the cognate DNA target region, an in vitro transcribed (IVT) gRNA screen was conducted. The relevant genomic sequence was submitted for analysis using a gRNA design software. The resulting list of gRNAs were narrowed to a select list of gRNAs as described above based on uniqueness of sequence (only gRNAs without a perfect match somewhere else in the genome were screened) and minimal predicted off targets. This set of gRNAs was in vitro transcribed, and transfected using Lipofectamine MessengerMAX into HEK293T cells that constitutively express Cas9. Cells were harvested 48 hours post transfection, the genomic DNA was isolated, and cutting efficiency was evaluated using TIDE analysis. (FIGS. 2A-G; FIGS. 3A-C).

The gRNA or pairs of gRNA with significant activity can then be followed up in cultured cells to measure SCN9A protein expression. Off-target events can be followed again. A variety of cells can be transfected and the level of gene correction and possible off-target events measured. These experiments allow optimization of nuclease and donor design and delivery.

Example 9

Testing of Preferred Guides in Cells for Off-Target Activity

The gRNAs having the best on-target activity from the IVT screen in the above example are tested for off-target activity using Hybrid capture assays, GUIDE Seq. and whole genome sequencing in addition to other methods.

Example 10

In Vivo Testing in Relevant Animal Model

After the CRISPR-Cas9/guide combinations have been re-assessed, the lead formulations will be tested in vivo in an animal model.

Culture in human cells allows direct testing on the human target and the background human genome, as described above.

Preclinical efficacy and safety evaluations can be observed through engraftment of modified mouse or human neurons of the peripheral nervous system in a mouse model. The modified cells can be observed in the months after engraftment.

XI. EQUIVALENTS AND SCOPE

Those skilled in the art will recognize, or be able to ascertain using no more than routine experimentation, many equivalents to the specific examples in accordance with the invention described herein. The scope of the present disclosure is not intended to be limited to the above Description, but rather is as set forth in the appended claims.

Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes examples in which exactly one member of the group is present in, employed in, or otherwise relevant to a given product or process. The present disclosure includes examples in which more than one, or the entire group members are present in, employed in, or otherwise relevant to a given product or process.

In addition, it is to be understood that any particular example of the present disclosure that falls within the prior art may be explicitly excluded from any one or more of the claims. Since such examples are deemed to be known to one of ordinary skill in the art, they may be excluded even if the exclusion is not set forth explicitly herein. Any particular example of the compositions of the present disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the present disclosure in its broader aspects.

While the present invention has been described at some length and with some particularity with respect to the several described examples, it is not intended that it should be limited to any such particulars or examples or any particular example, but it is to be construed with references to the appended claims so as to provide the broadest possible interpretation of such claims in view of the prior art and, therefore, to effectively encompass the intended scope of the invention.

NOTE REGARDING ILLUSTRATIVE EXAMPLES

While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

Any patent, publication, or other disclosure material identified herein is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11459587B2). An electronic copy of the "Sequence Listing" will also be available from the USPTO upon request and payment of the fee set forth in 37 CFR 1.19(b)(3).

The invention claimed is:

1. A method for editing a Sodium Voltage-Gated Channel Alpha Subunit 9 (SCN9A) gene in a cell by genome editing comprising: introducing into the cell (a) one or more *S. pyogenes* Cas9 (spCas9) endonuclease or one or more polynucleotide encoding the one or more spCas9 endonuclease and (b) one or more gRNA or sgRNA or one or more nucleic acid encoding the one or more gRNA or sgRNA, wherein the one or more gRNA or sgRNA comprises a spacer sequence that targets a sequence within or near the SCN9A gene to effect one or more single-strand breaks (SSBs) or double-strand breaks (DSBs) within or near the SCN9A gene or SCN9A regulatory elements that results in one or more permanent insertions, deletions or mutations of at least one nucleotide within or near the SCN9A gene, thereby reducing or eliminating the expression or function of SCN9A gene products, wherein the spacer sequence of the one or more gRNA or sgRNA consists of an RNA sequence corresponding to any one of SEQ ID NO: 46832, 49122, 49431, 47474, 47446, 28779, 29821, 28146, 49436, 47224, 47462, 47240, 27323, 27522, 27893, 47261, 28137, 49367, 47232, 47445, 49313, 47267, 30622, 47231, 26766, 28139, 46079, 48091, 46833, 26765, 27876, 47241, 47248, 30051, 30111, 28760, 28085, 27254, 30163, 49303, 28083, 49344, 47245, 48090, 28132, 27328, 46078, 28773, 46496, 27885, 29928, 27933, 46039, 47439, 28774, 47455, 30020, 47236, 28089, 26813, 47464, 28091, 29908, 27892, 28776, 28783, 27252, 29930, or 47625.

2. An in vivo method for treating a patient with an SCN9A related disorder comprising: editing the Sodium Voltage-Gated Channel Alpha Subunit 9 (SCN9A) gene in a cell of the patient according to the method of claim 1, optionally wherein the cell is a neuron of the peripheral nervous system.

3. The method of claim 1, wherein the one or more spCas9 endonuclease comprises one or more nuclear localization signal (NLS) or the one or more polynucleotide encoding the one or more spCas9 endonuclease further encodes one or more NLS.

4. The method of claim 3, wherein the one or more NLS is at or within 50 amino acids of the amino-terminus of the spCas9 endonuclease and/or the one or more NLS is at or within 50 amino acids of the carboxy-terminus of the spCas9 endonuclease.

5. The method of claim 1, wherein the one or more spCas9 endonuclease is one or more protein or polypeptide.

6. The method of claim 1, wherein the one or more polynucleotide encoding the one or more spCas9 endonuclease is codon optimized.

7. The method of claim 1, wherein the one or more polynucleotide encoding the one or more spCas9 endonuclease is one or more DNA.

8. The method of claim 1, wherein the one or more polynucleotide encoding the one or more spCas9 endonuclease is one or more RNA.

9. The method of claim 8, wherein the one or more RNA is chemically modified.

10. The method of claim 1, wherein said one or more gRNA or sgRNA is pre-complexed with the one or more spCas9 endonuclease.

11. The method of claim 1, wherein the one or more spCas9 endonuclease or the one or more polynucleotide encoding the one or more spCas9 endonuclease and/or the one or more gRNA or sgRNA or the one or more nucleic acid encoding the one or more gRNA or sgRNA is formulated in a liposome or lipid nanoparticle.

12. The method of claim 1, wherein the one or more polynucleotide encoding the one or more Cas9 endonuclease and/or the one or more nucleic acid encoding the one or more gRNA or sgRNA is provided by an AAV vector particle.

13. The method of claim 12, wherein the AAV vector particle is selected from the group consisting of AAV1, AAV2, AAV3, AAV4, AAV5, AAV6, AAV7, AAV8, and AAV9 particle.

14. The method of claim 1, wherein the cell is a stem cell.

15. The method of claim 14, wherein the stem cell is a pluripotent stem cell, an induced pluripotent stem cell (iPSC), a mesenchymal stem cell, an adult stem cell, or a somatic stem cell.

16. The method of claim 1, wherein the cell is a somatic cell.

17. The method of claim 16, wherein the somatic cell is a neuron of the peripheral nervous system.

* * * * *